US012345711B2

(12) United States Patent
Geiger et al.

(10) Patent No.: US 12,345,711 B2
(45) Date of Patent: Jul. 1, 2025

(54) METHODS TO DETERMINE ANTIBODY ACTIVITY IN TUMOR SAMPLES

(71) Applicant: Hoffmann-La Roche Inc., Little Falls, NJ (US)

(72) Inventors: Martina Geiger, Schlieren (CH); Christian Klein, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 935 days.

(21) Appl. No.: 16/439,669

(22) Filed: Jun. 12, 2019

(65) Prior Publication Data
US 2020/0116727 A1    Apr. 16, 2020

Related U.S. Application Data

(63) Continuation of application No. PCT/EP2017/082112, filed on Dec. 11, 2017.

(30) Foreign Application Priority Data

Dec. 13, 2016 (EP) .................................. 16203724

(51) Int. Cl.
G01N 33/00       (2006.01)
C07K 16/28       (2006.01)
C07K 16/30       (2006.01)
C12Q 1/6897      (2018.01)
G01N 33/574      (2006.01)

(52) U.S. Cl.
CPC ... G01N 33/57484 (2013.01); C07K 16/2809 (2013.01); C07K 16/30 (2013.01); C12Q 1/6897 (2013.01); C07K 2317/31 (2013.01); C07K 2317/622 (2013.01)

(58) Field of Classification Search
CPC ......... G01N 33/57484; G01N 33/6845; C07K 16/2809; C07K 16/30; C07K 2317/31; C07K 2317/622; C12Q 1/6897
See application file for complete search history.

(56) References Cited

U.S. PATENT DOCUMENTS

| 4,676,980 | A | 6/1987 | Segal et al. |
| 5,571,894 | A | 11/1996 | Wels et al. |
| 5,587,458 | A | 12/1996 | King et al. |
| 5,731,168 | A | 3/1998 | Carter et al. |
| 5,869,046 | A | 2/1999 | Presta et al. |
| 6,248,516 | B1 | 6/2001 | Winter et al. |
| 7,695,936 | B2 | 4/2010 | Carter et al. |
| 2006/0025576 | A1 | 2/2006 | Miller et al. |
| 2008/0069820 | A1 | 3/2008 | Fuh et al. |
| 2019/0119383 | A1* | 4/2019 | Bruenker ........... C07K 16/2863 |

FOREIGN PATENT DOCUMENTS

| EP | 0404097 B1 | 12/1990 |
| JP | 2016-525551 A | 4/2010 |
| WO | 93/01161 A1 | 1/1993 |
| WO | 93/08829 A1 | 5/1993 |
| WO | 93/16185 A2 | 8/1993 |
| WO | 2009/089004 A1 | 7/2009 |
| WO | 2015/013671 A1 | 1/2015 |
| WO | 2016/014974 A2 | 1/2016 |
| WO | 2016/079050 A1 | 5/2016 |
| WO | 2016/079076 A1 | 5/2016 |
| WO | 2016/191750 A1 | 12/2016 |

OTHER PUBLICATIONS

Promega Technical Manual (Nov. 2016)—T cell activation bioassay (NFAT) (Year: 2016).*
Stecha et al (Cancer Res 75: (15-supplement): 5439, Aug. 2015) (Year: 2015).*
Stecha et al (Post, Promega.com, published Aug. 2016). (Year: 2016).*
Almagro et al., "Humanization of antibodies" Front Biosci 13:1619-1633 (Jan. 1, 2008).
Brennan et al., "Preparation of Biospecific Antibodies By Chemical Recombination of Monoclonal Immunoglobulin G1 Fragments" Science 229(4708):81-83 (Jul. 5, 1985).
Carter, "Bispecific human IgG by design" J Immunol Methods 248(1-2):7-15 (Feb. 1, 2001).
Cheng, Z., et al., "Development of a Robust Reporter-based T cell Activation Assay for Therapeutic Biologics in Immunotherapy" Poster Development of a Robust Reporter-based T cell Activation Assay for Therapeutic Biologics in Immunotherapy, Promega, ( May 2, 2014).
Cheng, Z., et al., "Development of a robust reporter-based ADCC assay with frozen, thaw-and-use cells to measure Fc effector function of therapeutic antibodies" J Immunol Methods 414:69-81 (Jul. 31, 2014).
Cheng, Z., "Reporter Gene Immunotherapy Bioassays" Poster BEBPA 2016, ( Sep. 30, 2016).
Chothia et al., "Canonical structures for the hypervariable regions of immunoglobulins" J Mol Biol 196(4):901-917 (Apr. 23, 1987).
Clackson et al., "Making antibody fragments using phage display libraries" Nature 352(6336):624-628 (Aug. 15, 1991).
Cui, H. et al., "Chemically Programmed Bispecific Antibodies That Recruit and Activate T Cells" J Biochem 287(34):28206-28214 (Jul. 3, 2012).
Fingl et al. Basis of Therapeutics, "Ch. 1—General Principles" Fifth edition, New York: Macmillan Publishing Co., Inc.,:1-46 (1975).
Flatman et al., "Process analytics for purification of monoclonal antibodies" J Chromatogr 848(1):79-87 (Mar. 15, 2007).

(Continued)

Primary Examiner — Lei Yao
(74) Attorney, Agent, or Firm — GENENTECH, INC.

(57) ABSTRACT

The present invention relates to a new cell-based assay for determining antigen expression in primary tumor samples. The method further relates to the determination of antigen and protease expression in primary tumor samples. The method allows robust determination of antigen and/or protease expression without the need to digest the tumor samples. The method further allows for selection of antibodies and for selection of protease-cleavable linkers for the treatment of tumors.

17 Claims, 16 Drawing Sheets
Specification includes a Sequence Listing.

(56) References Cited

OTHER PUBLICATIONS

Gruber et al., "Efficient tumor cell lysis mediated by a bispecific single chain antibody expressed in *Escherichia coli*" J Immunol 152(11):5368-5374 (Mar. 17, 1994).
Holliger, P., et al., "'Diabodies': Small bivalent and bispecific antibody fragments" PNAS 90(14):6444-6448 (Jul. 15, 1993).
Hudson et al., "Engineered antibodies" Nat Med 9(1):129-134 (Jan. 1, 2003).
"International Preliminary Report on Patentability—PCT/EP2017/082112": pp. 1-9 (Jun. 27, 2019).
"International Search Report—PCT/EP2017/082112": pp. 1-10 (Mar. 19, 2018).
Kabat et al. et al., "Sequences of Proteins of Immunological Interest" NIH Publication NIH 91-3242 (Fifth Edition), I:647-669 ( 1991).
Kabat et al. U.S. Dept. of Health and Human Services, Public Health Services, NIH Publ. No. 91-3242:3 "Sequences of Proteins of Immunological Interest" ( 1983).
Kindt et al. Kuby Immunol Sixth edition, New York:W. H. Freeman and Company,:91 ( 2007).
Kostelny, S., et al., "Formation of a bispecific antibody by the use of leucine zippers" J Immunol 148(5):1547-1553 (Mar. 1, 1992).
Ma, Pan, et al., "Anti-CD3 x EGFR bispecific antibody redirects cytokine-induced killer cells to glioblastoma in vitro and in vivo" Oncol Rep 34:2567-2575 (May 14, 2015).
Milstein et al., "Hybrid hybridomas and their use in immunohistochemistry" Nature 305:537-540 (Oct. 6, 1983).
Morrison et al., "Chimeric human antibody molecules: Mouse antigen-binding domains with human constant region domains" PNAS 81(21):6851-6855 (Nov. 1, 1984).
Parekh, Bhavin S., et al., "Development and validation of an antibody-dependent cell-mediated cytotoxicity-reporter gene assay" MABS 4(3):310-318 (May 1, 2012).
Pluckthun et al. The Pharmacology of Monoclonal Antibodies Rosenburg and Moore (eds.), New York: Springer-Verlag, vol. 113:269-315 ( 1994).

Polu, Krishna, et al., "Probody therapeutics for targeting antibodies to diseased tissue" Expert Opin Biol Th 14(8):1049-1053 (Aug. 1, 2014).
Portolano, S., et al., "Lack of promiscuity in autoantigen-specific H and L chain combinations as revealed by human H and L chain 'Roulette'" J Immunol 150(3):880-887 (Feb. 1, 1993).
Ridgway, J., et al., "'Knobs-into-holes' engineering of antibody CH3 domains for heavy chain heterodimerization" Protein Eng 9(7):617-621 (Jul. 1, 1996).
Schroten, C., et al., "T cell activation upon exposure to patient-derived tumor tissue: A functional assay to select patients for adoptive T cell therapy" J Immunol Methods 359(1-2):11-20 (Jul. 31, 2010).
Stel, Alja J., et al., "The Role of B Cell-Mediated T Cell Costimulation in the Efficacy of the T Cell Retargeting Bispecific Antibody Bis" J Immunol 173(10):6009-6016 (Nov. 1, 2004).
Stubenrauch et al., "Impact of molecular processing in the hinge region of therapeutic IgG4 antibodies on disposition profiles in cynomolgus monkeys" Drug Metab Dispos 38(1):84-91 (Jan. 1, 2010).
Sun, L., et al., "Anti-CD20/CD3 T cell-dependent bispecific antibody for the treatment of B cell malignancies" Sci Trans Med 7(287 SUPPL 287ra70):1-10 (May 13, 2015).
Technical Manual, pp. 3 (T Cell Activation Bioassay (NFAT) Nov. 7, 2016).
Traunecker, A., et al., "Bispecific Single Chain Molecules (Janusins) Target Cytotoxic Lymphocytes on HIV Infected Cells" EMBO J 10(12):3655-3659 (Aug. 19, 1991).
Tutt et al., "Trispecific F(ab') 3 derivatives that use cooperative signalling via the TCR/CD3 complex and CD2 to activate and redirect resting cytotoxic T cells" J Immunol 147(1):60-69 (Jul. 1, 1991).
Withoff, S., et al., "Characterization of BIS20x3, a bi-specific antibody activating and retargeting T-cells to CD20-positive B-cells" Brit J Cancer 84(8):1115-1121 (Jan 1, 2001).
Schreiner, J., et al., "Expression of inhibitory receptors on intratumoral T cells modulates the activity of a T cell-bispecific antibody targeting folate receptor" Oncoimmunology 5(2 Suppl e1062969):1-11 (Jun. 24, 2015).

\* cited by examiner

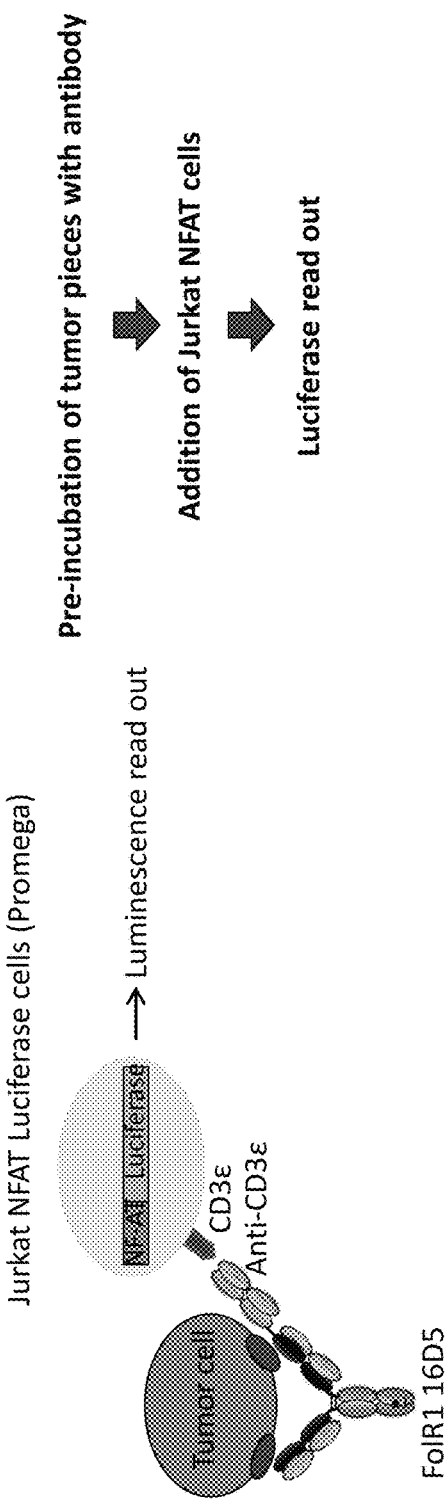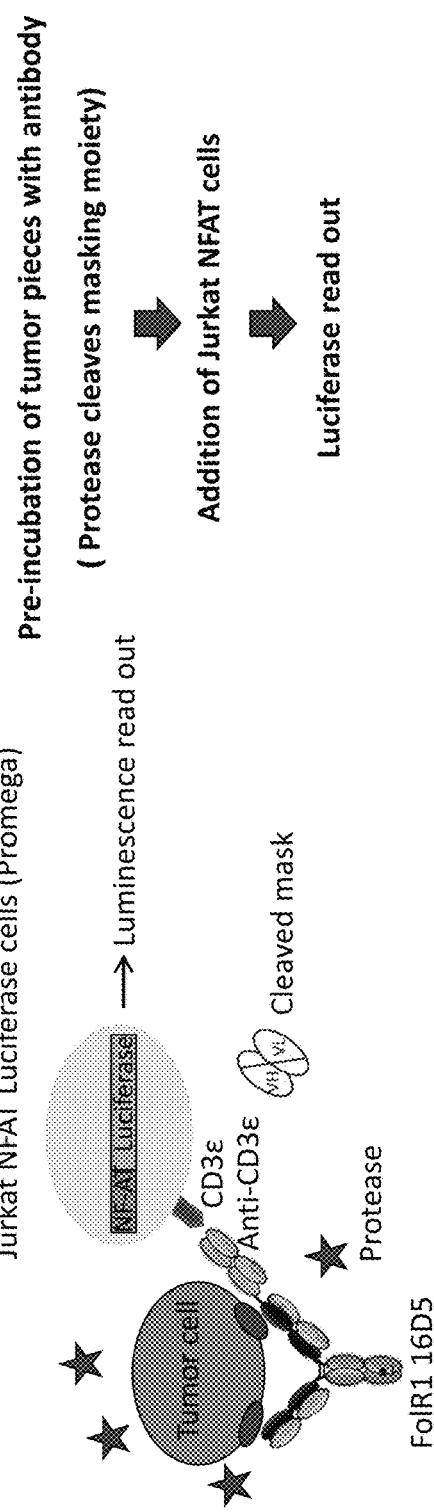
Figure 1A
Figure 1B

METHODS TO DETERMINE ANTIBODY ACTIVITY IN TUMOR SAMPLES

CROSS REFERENCE TO RELATED APPLICATIONS

This application is a continuation of International Patent Application No. PCT/EP2017/082112 filed Dec. 11, 2017, which claims priority to European Patent Application No. 16203724.6, filed Dec. 13, 2016, the disclosure of which are incorporated hereby reference in their entirety.

SEQUENCE LISTING

The instant application contains a Sequence Listing submitted via EFS-Web and hereby incorporated by reference in its entirety. Said ASCII copy, created on May 30, 2019 is named P34016-US-SequenceListing.txt, and is 114,688 bytes in size.

FIELD OF THE INVENTION

The present invention relates to a new cell-based assay for determining antigen expression in primary tumor samples. The method further relates to the determination of antigen and protease expression in primary tumor samples. The method allows robust determination of antigen and/or protease expression without the need to digest the tumor samples. The method further allows for selection of antibodies and for selection of protease-cleavable linkers for the treatment of tumors.

BACKGROUND

Chemotherapy is until now still one of the most commonly used treatments for cancer. Additionally, antibody based therapies have evolved over the last 15 years and represent now a valuable combination or alternative to chemotherapeutic approaches in the treatment of tumors. Unlike chemotherapy, antibody therapies target specific antigens on cancer cells thus allowing a more side directed treatment thereby reducing the side effects on healthy tissue. In the process of developing an antibody-based therapeutic reagent, various assays are required to identify the best candidates to bring into clinical trials and eventually to the market. In a first early preclinical phase, the antibodies have to be generated and analyzed for their target-specificity, as well as their affinity to the target and functionality. Binding properties can be analyzed using various protein-protein interaction assays, such as FRET-based methods, Surface Plasmon Resonance (SPR), fluorescence-activated cell sorting (FACS) or Alpha Screen™. Functionality is generally tested in various cell-based assays designed to mimic the physiological situation as close as possible to identify the best candidates to be tested in animal models before entering clinical trials. These functional assays are commonly carried out using primary cells, tumor cell lines or reporter cells that are designed to express a reporter upon activation of a specific pathway.

However, cell lines or primary cells in culture may not be a comprehensive model of tumor tissue which usually is a more complex three dimensional assembly of cells. On the other hand functional assays are robust and straight-forward on cells in culture since the measurement of test parameters can be done on single cells such as antibody binding or function, e.g., killing of target cells. Tumor samples are much more difficult to assess directly because of several obstacles. Tumors contain, besides the tumor cells, also a complex extracellular matrix environment, partially or completely generated by excretion of extracellular matrix components by cells in the tumor. Extracellular matrix may restrain penetration of antibodies into the tumor tissue but may also interfere with accessability of cell surface targets on the tumor cells. However, extracellular components may also contain additional antigenic or functional elements which may be valuable for targeted immunotherapy.

In conclusion, there is a need for more comprehensible and robust assays for direct determination of antibody binding and functionality on tumor samples, in particular derived from biopsies of tumors.

Recently, targeted immunotherapy, the activation of autologous elements of the immune system to attack tumor cells, is becoming a sharp sword in the battle to overcome tumor immune tolerance. Bispecific constructs comprising a binding moiety capable of recognizing the tumor cells and an effector moiety activating immune cells have shown promising results. However, in some instances it might be necessary to conceil the effector moiety until delivery of the bispecific molecules to the tumor to reduce unspecific systemic side effects. One approach to accomplish this is to conceal the effector moiety with an anti-idiotypic binding moiety capable of reversible binding the effector moiety and connecting the concaling moiety to the bispecific immunotherapeutic antibody using protease cleavable linkers. Tumors, especially malignant tumors, are well known to comprise proteases not expressed or not present in their active form in healthy adult tissue. Constructs with protease-cleavable linkers can therefore be used to target the activity of novel classes of bispecific antibodies to the tumor tissue.

With increasing complexity of constructs for immunotherapy, the requirements to assays for measuring binding and functionality of antibodies in a comprehensive setup increase as well. Binding assays on cells in culture may not be sufficient to model the complex environment in tumor tissue.

The inventors of the present invention developed a novel assay which combines the assessment of binding and functionality of antibodies and antibody like constructs directly on tumor samples, such as e.g., tumor biopsies. This novel assay is useful for example for screening or characterization purposes in early development of new antibody constructs as well as for selecting suitable antibodies for treatment of cancer.

This new assay represents a valuable tool for screening binding and targeted functionality in tumor samples which will allow identifying the best constructs at an early stage in the development of the drug candidate and to identify suitable treatments for patients.

SUMMARY

Provided is an in vitro method for determining the presence of a target antigen in a tumor sample comprising the steps of:
i) providing a tumor sample;
ii) providing reporter cells comprising a reporter gene under the control of a signal transducing cell surface receptor;
iii) adding to the tumor sample a bispecific antibody comprising:
 a) a first antigen binding moiety capable of specific binding to a target antigen; and b) a second antigen binding moiety capable of specific binding to the signal transducing cell surface receptor;

iv) adding the reporter cells to the tumor sample; and v) determining the presence of the target antigen by determining the expression of the reporter gene.

In one embodiment, the target antigen is expressed by the tumor cells.

In one embodiment, the expression of the reporter gene is indicative for binding of the first antigen binding moiety to the target antigen.

In one embodiment, the bispecific antibody of step iii) additionally comprises c) a masking moiety covalently attached to the second antigen binding moiety through a protease-cleavable linker, wherein the masking moiety is capable of specific binding to the idiotype of the second antigen binding moiety thereby reversibly concealing the second antigen binding moiety.

In one embodiment, a protease cleaves the protease-cleavable linker, wherein the second antigen binding moiety is unconcealed.

In one embodiment, the protease is expressed by the tumor cells.

In one embodiment, the expression of the reporter gene is indicative for protease expression in the tumor sample.

In one embodiment, the tumor sample is a tumor tissue sample, in particular a biopsy from a patient.

In one embodiment, the tumor sample is not digested.

In one embodiment, the tumor sample is digested, in particular by in particular by collagenase or hyaluronidase.

In one embodiment, the tumor sample contains dead cells, in particular more than 10% of dead cells.

In one embodiment, protease expression is indicative for a malignant tumor.

In one embodiment, the signal transducing cell surface receptor is functionally linked to a response element.

In one embodiment, the response element controls the expression of the reporter gene.

In one embodiment, the response element is part of the NF-κB pathway.

In one embodiment, the response element comprises at least one DNA repeat with a DNA sequence of SEQ ID NO: 68, 69, 70, 71 or 72.

In one embodiment, the response element comprises a DNA sequence of SEQ ID NO 73, 74, 75 or 76.

In one embodiment, the reporter gene is coding for a fluorescent or a luminescent protein.

In one embodiment, the reporter gene is coding for green fluorescent protein (GFP) or luciferase.

In one embodiment, the reporter cells comprise the DNA sequence coding for the reporter gene under the control of the response element, and the DNA sequence coding for signal transducing cell surface receptor.

In one embodiment, the reporter cells comprise at least one DNA repeat with a DNA sequence of SEQ ID NO: 68, 69, 70, 71 or 72, wherein the DNA repeat is operatively linked to the reporter gene and wherein the reporter gene is expressed upon binding of the second antigen binding moiety to the signal transducing cell surface receptor.

In one embodiment, the second antigen binding moiety is capable of specific binding to CD3.

In one embodiment, the protease-cleavable linker comprises a protease recognition sequence.

In one embodiment, the protease recognition sequence is selected from the group consisting of:

a)
(SEQ ID NO: 45)
RQARVVNG;

b)
(SEQ ID NO: 46)
VHMPLGFLGPGRSRGSFP;

c)
(SEQ ID NO: 47)
RQARVVNGXXXXXVPLSLYSG;

d)
(SEQ ID NO 48)
RQARVVNGVPLSLYSG;

e)
(SEQ ID NO: 49)
PLGLWSQ;

f)
(SEQ ID NO: 50)
VHMPLGFLGPRQARVVNG;

g)
(SEQ ID NO: 51)
FVGGTG;

h)
(SEQ ID NO: 52)
KKAAPVNG;

i)
(SEQ ID NO: 53)
PMAKKVNG;

j)
(SEQ ID NO: 54)
QARAKVNG;

k)
(SEQ ID NO: 55)
VHMPLGFLGP;

l)
(SEQ ID NO: 56)
QARAK;

m)
(SEQ ID NO: 57)
VHMPLGFLGPPMAKK;

n)
(SEQ ID NO: 58)
KKAAP;
and o)
(SEQ ID NO: 59)
PMAKK, wherein X is any amino acid.

In one embodiment, the protease is selected from the group consisting of metalloproteinase, serine protease, cysteine protease, aspartic proteases, and cathepsin protease.

In one embodiment, the metalloproteinase is a matrix metalloproteinase (MMP), particularly MMP9 or MMP2.

In one embodiment, the serine protease is Matriptase.

In one embodiment, the masking moiety is covalently attached to the heavy chain variable region of the second antigen binding moiety.

In one embodiment, the masking moiety is covalently attached to the light chain variable region of the second antigen binding moiety.

In one embodiment, the masking moiety is an anti-idiotypic scFv.

In one embodiment, the first and the second antigen binding moiety are fused to each other, optionally via a peptide linker.

In one embodiment, the first and the second antigen binding moieties are conventional Fab molecules comprising a common light chain.

In one embodiment, the second antigen binding moiety is fused at the C-terminus of the Fab heavy chain to the N-terminus of the Fab heavy chain of the first antigen binding moiety, optionally via a peptide linker.

In one embodiment, the Fab light chain of the first antigen binding moiety and the Fab light chain of the second antigen binding moiety are fused to each other, optionally via a peptide linker.

In one embodiment, the bispecific antibody comprises a third antigen binding moiety capable of specific binding a tumor antigen.

In one embodiment, the third antigen binding moiety is a conventional Fab molecule, or a crossover Fab molecule wherein either the variable or the constant regions of the Fab light chain and the Fab heavy chain are exchanged.

In one embodiment, the third antigen binding moiety is identical to the first antigen binding moiety.

In one embodiment, the bispecific antibody additionally comprises an Fc domain composed of a first and a second subunit capable of stable association.

In one embodiment, the Fc domain is an IgG, specifically an IgG1 or IgG4. Fc domain.

In one embodiment, the Fc domain is a human Fc domain.

In one embodiment, the target antigen is a cell surface receptor.

In one embodiment, the target antigen is FolR1.

In one embodiment, the target antigen is a peptide bound to a molecule of the human major histocompatibility complex (MHC).

In one embodiment, the peptide has an overall length of between 8 and 100, preferably between 8 and 30, and more preferred between 8 and 16 amino acids.

In one embodiment, the binding to the target antigen and the expression of the protease are determined in the same vial.

In one embodiment, provided is an in vitro method for selecting a bispecific antibody for the treatment of a tumor, wherein the bispecific antibody comprises:
  a. a first antigen binding moiety capable of specific binding to a target antigen; and
  b. a second antigen binding moiety capable of specific binding to a signal transducing cell surface receptor;
wherein the method comprises determining the presence of a target antigen in a tumor sample according to the method as described herein and wherein the bispecific antibody is selected for treatment of the tumor if expression of the reporter gene is detected.

In further embodiments, provided are methods essentially as herein described.

BRIEF DESCRIPTION OF THE FIGURES

FIG. 1 depicts the assay principle. FIG. 1A: Jurkat-NFAT reporter cell line (Promega) is a human acute lymphatic leukemia reporter cell line with a NFAT promoter, expressing human CD3ε. If the CD3 binder of the TCB binds the tumor target and the CD3 (crosslinkage is necessary) binds CD3ε the Luciferase expression can be measured in Luminescence after addition of One-Glo substrate (Promega). FIG. 1B: Masking the CD3 binder with a protease-cleavable linker only induces Jurkat-NFAT reporter gene activation if the protease expressed by the tumor can cleave the linker.

FIG. 2 depicts schematics of different bispecific CD3 binders with and without masking moieties.

FIG. 3 depicts CE-SDS analysis of different bispecific CD3 binders.

FIG. 7 depicts the Jurkat-NFAT activation assay with patient-derived xenografts.

Figure 2A:
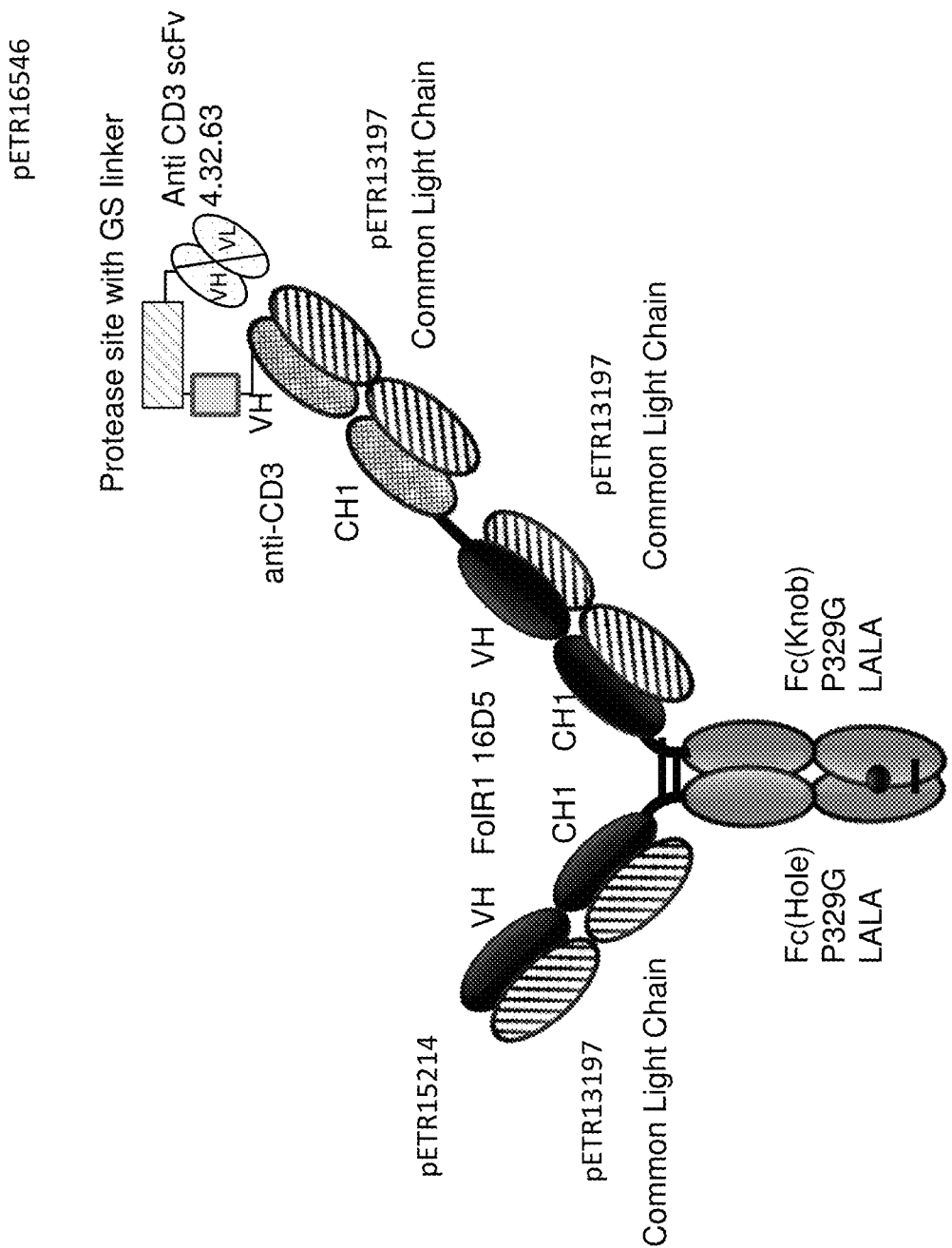
FIG. 2A: ID 8364. 16D5 TCB, classic format, anti ID CH2527 scFv 4.32.63 MMP9-MK062 Matriptase site N-terminally fused to CD3.
Figure 2B:
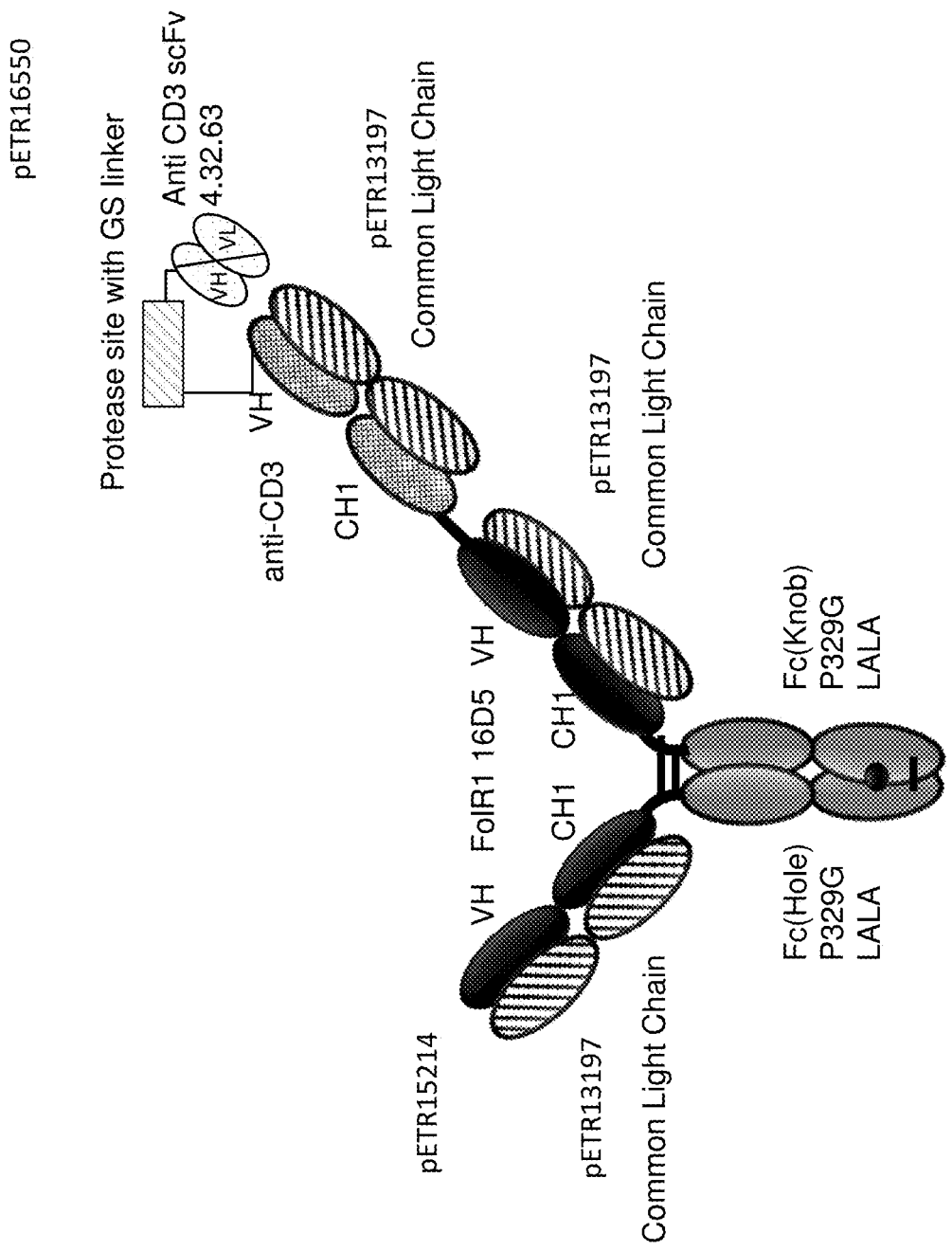
FIG. 2B: ID 8363. 16D5 TCB, classic format, anti ID CH2527 scFv 4.32.63 Cathepsin S/B site N-terminally fused to CD3.
Figure 2C:
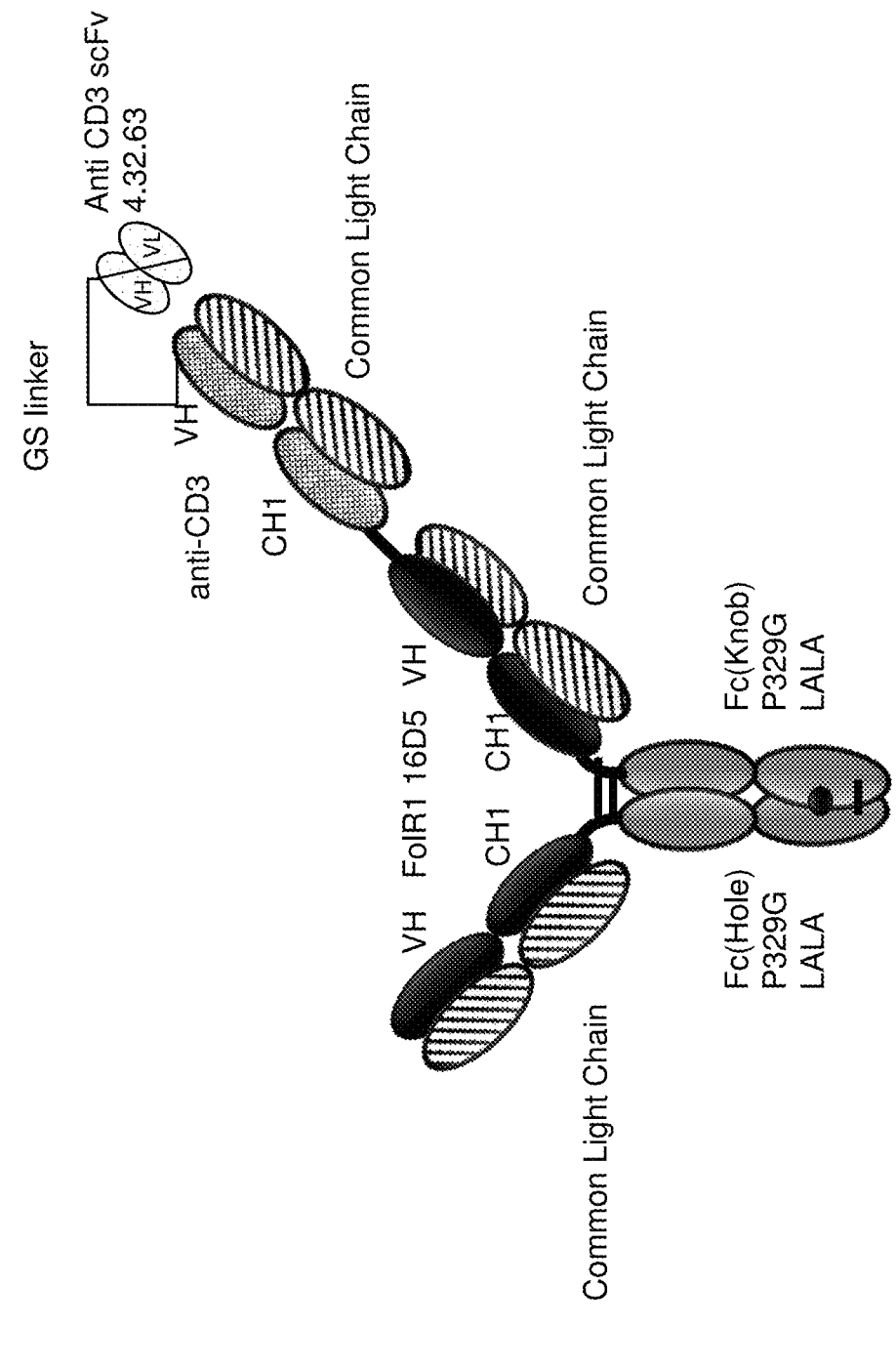
FIG. 2C: ID 8409, anti ID CH2527 scFv 4.32.63 non cleavable linker CD3 16D5 Fc.
Figure 2D:
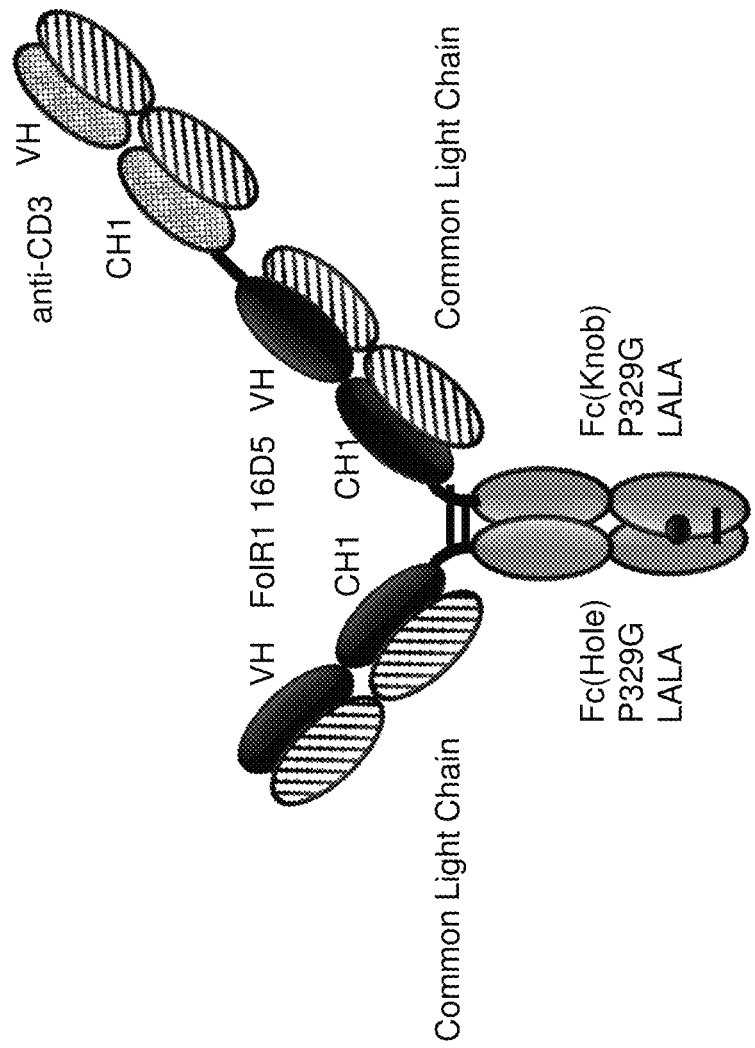
FIG. 2D: ID 6298. FolR1 16D5 classic 2+1 TCB with common light chain.
Figure 2E:
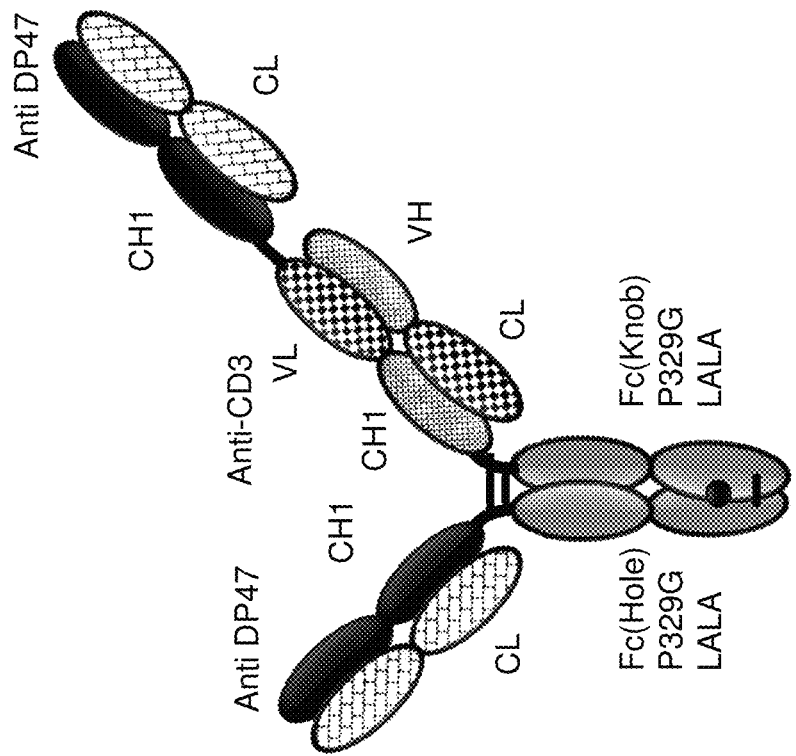
FIG. 2E: ID 6182 and 7235. DP47GS TCB sf CHO W(9a). DP47 inverted 2+1 TCB.

Observed is a positive correlation between the activation measured using the Jurkat NFAT activation assay and the levels of p95HER2 determined by the quantitative IHC-based assay.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody or ligand) and its binding partner (e.g., an antigen or a receptor). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense to a molecule that specifically binds an antigenic determinant and encompasses various antibody structures, including but not limited to monoclonal antibodies, polyclonal antibodies, multispecific antibodies (e.g., bispecific antibodies), and antibody fragments so long as they exhibit the desired antigen-binding activity.

"Antibody specificity" refers to selective recognition of the antibody for a particular epitope of an antigen. Natural antibodies, for example, are monospecific.

The term "antigen binding domain" refers to the part of an antibody that comprises the area which specifically binds to and is complementary to part or all of an antigen. Where an antigen is large, an antibody may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

As used herein, the term "antigen binding moiety" refers to a polypeptide molecule that specifically binds to an antigenic determinant. In one embodiment, an antigen binding moiety is able to direct the entity to which it is attached (e.g., a second antigen binding moiety) to a target site, for example to a specific type of tumor cell or tumor stroma bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

An "antigen binding site" refers to the site, i.e. one or more amino acid residues, of an antibody which provides interaction with the antigen. For example, the antigen binding site of an antibody comprises amino acid residues from the "complementarity determining regions" (CDRs). A native immunoglobulin molecule typically has two antigen binding sites, a Fab molecule typically has a single antigen binding site.

The term "antigen-binding site of an antibody" when used herein refer to the amino acid residues of an antibody which are responsible for antigen-binding. The antigen-binding portion of an antibody comprises amino acid residues from the CDRs. "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, MD (1991) and/or those residues from a "hypervariable loop".

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, cross-Fab fragments; linear antibodies; single-chain antibody molecules (e.g. scFv); and multispecific antibodies formed from antibody fragments. For a review of scFv fragments, see e.g., Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9. 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g., U.S. Pat. No. 6,248,516 B1). Antibody fragments can be made by various techniques, including but not limited to proteolytic digestion of an intact antibody as well as production by recombinant host cells (e.g., *E. coli* or phage).

As used herein, the term "antigenic determinant" is synonymous with "antigen" and "epitope", and refers to a site (e.g., a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g., FolR1 and CD3) can be any native form of the proteins from any vertebrate source, including mammals such as primates (e.g., humans) and rodents (e.g., mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g., splice variants or allelic variants. Exemplary human proteins useful as antigens include, but are not limited to: FolR1 and CD3, particularly the epsilon subunit of CD3 (see UniProt no. P07766 (version 130), NCBI RefSeq no. NP_000724.1, SEQ ID NO: 60 for the human sequence; or UniProt no. Q95LI5 (version 49). NCBI GenBank no. BAB71849.1 for the cynomolgus [*Macaca fascicularis*] sequence). In certain embodiments the bispecific molecule of the invention binds to an epitope of CD3 or a target cell antigen that is conserved among the CD3 or target antigen from different species. In certain embodiments the bispecific molecule of the invention binds to CD3 and FolR1.

The term "bispecific" antibody as used herein denotes an antibody that has at least two binding sites each of which bind to different epitopes of the same antigen or a different antigen. Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see. e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see. e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad Sci. USA, 90:6444-6448 (1993)); and using single-chain Fv (sFv) dimers (see. e.g. Gruber et al., J. Immunol., 152:5368 (1994)): and preparing trispecific antibodies as described. e.g., in Tutt et al. J. Immunol. 147: 60 (1991). A bispecific antibody is able to specifically bind to at least two distinct antigenic determinants. Typically, a bispecific antibody comprises two antigen binding sites, each of which is specific for a different antigenic determinant. In certain embodiments the bispecific antibody is capable of simultaneously binding two antigenic determinants, particularly two antigenic determinants expressed on two distinct cells.

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a rabbit variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

By a "crossover" Fab molecule (also termed "Crossfab") is meant a Fab molecule wherein either the variable regions or the constant regions of the Fab heavy and light chain are exchanged, i.e. the crossover Fab molecule comprises a peptide chain composed of the light chain variable region and the heavy chain constant region, and a peptide chain composed of the heavy chain variable region and the light chain constant region. For clarity, in a crossover Fab molecule wherein the variable regions of the Fab light chain and the Fab heavy chain are exchanged, the peptide chain comprising the heavy chain constant region is referred to herein as the "heavy chain" of the crossover Fab molecule. Conversely, in a crossover Fab molecule wherein the constant regions of the Fab light chain and the Fab heavy chain are exchanged, the peptide chain comprising the heavy chain variable region is referred to herein as the "heavy chain" of the crossover Fab molecule.

In contrast thereto, by a "conventional" Fab molecule is meant a Fab molecule in its natural format, i.e. comprising a heavy chain composed of the heavy chain variable and constant regions (VH-CH1), and a light chain composed of the light chain variable and constant regions (VL-CL).

An "effective amount" of an agent, e.g., a pharmaceutical formulation, refers to an amount effective, at dosages and for periods of time necessary, to achieve the desired therapeutic or prophylactic result.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. As used herein, the terms engineer, engineered, engineering, particularly with the prefix "glyco-", as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, "Fab fragment" refers to an antibody fragment comprising a light chain fragment comprising a VL domain and a constant domain of a light chain (CL), and a VH domain and a first constant domain (CH1) of a heavy chain.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health. Bethesda, MD, 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

As used herein, the terms "first" and "second" with respect to antigen binding moieties etc., are used for convenience of distinguishing when there is more than one of each type of moiety. Use of these terms is not intended to confer a specific order or orientation of the bispecific antibody unless explicitly so stated.

A "Fab molecule" refers to a protein consisting of the VH and CH1 domain of the heavy chain (the "Fab heavy chain") and the VL and CL domain of the light chain (the "Fab light chain") of an immunoglobulin.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

As used herein, the term "functionality of an antibody or ligand" refers to the biological activity of an antibody or ligand, e.g. the ability of an antibody or ligand to elicit a cellular response. For example through binding to a target antigen, the antibody activates or suppresses a cell signaling pathway, i.e. activates of inhibits the function of the target antigen. For example, the antibody to be tested binds to a receptor activating the NF-κB pathway and through this binding a response element in the cell nucleus is activated. When linking this response element to a reporter gene, the activation can be easily monitored in the assay of the invention. The term "functionality" also includes the effector functions of an antibody, e.g. C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation; as well as activation of T cells.

By "fused" is meant that the components (e.g., a Fab molecule and an Fc domain subunit) are linked by peptide bonds, either directly or via one or more peptide linkers.

"High-throughput screening" as used herein shall be understood to mean that a relatively large number of different antibody or ligand candidates can be analyzed for binding and functionality with the novel assay described therein. Typical such high-throughput screening is performed in multi-well microtiter plates, e.g. in a 96 well plate or a 384 well plate or a plates with 1536 or 3456 wells.

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, MD (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
| --- | --- | --- | --- |
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

An "idiotype-specific polypeptide" as used herein refers to a polypeptide that recognizes the idiotype of an antigen-binding moiety, e.g., an antigen-binding moiety specific for CD3. The idiotype-specific polypeptide is capable of specifically binding to the variable region of the antigen-binding moiety and thereby reducing or preventing specific binding of the antigen-binding moiety to its cognate antigen. When associated with a molecule that comprises the antigen-binding moiety, the idiotype-specific polypeptide can function as a masking moiety of the molecule. Specifically disclosed herein are anti-idiotype antibodies or anti-idiotype-binding antibody fragments specific for the idiotype of anti-CD3 binding molecules.

An "immunoconjugate" is an antibody conjugated to one or more heterologous molecule(s), including but not limited to a cytotoxic agent.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g., $\gamma_1$ (IgG1), γ2 (IgG2), γ3 (IgG3), γ4 (IgG4), α1 (IgA1) and α2 (IgA2). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

As used herein, the term "ligand" refers to any molecule that is able to bind to another molecule. Example of ligand molecules include, but are not limited to peptides, proteins, carbohydrates, lipids, or nucleic acids. Preferred ligands to be analysed with the assay described herein are peptides or proteins that are capable of binding to a target antigen. Usually such target antigen is a cell surface receptor.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "monospecific" antibody as used herein denotes an antibody that has one or more binding sites each of which bind to the same epitope of the same antigen.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

As used herein "NF-κB" refers to the "nuclear factor kappa-light-chain-enhancer of activated B cells" and is a transcription factor which is implicated in the regulation of many genes that code for mediators of apoptosis, viral replication, tumorigenesis, various autoimmune diseases and inflammatory responses. NFκB is present in almost all eukaryotic cells. Generally, it is located in the cytosol in an inactive state, since it forms a complex with inhibitory kappa B (IκB) proteins. Through the binding of ligands to integral membrane receptors (also referred to as "receptors of the NF-κB pathway", the IκB kinase (IKK) is activated. IKK is an enzyme complex which consists of two kinases and a regulatory subunit. This complex phosphorylates the IκB proteins, which leads to ubiquitination and therefore degradation of those proteins by the proteasome. Finally, the free NFκB is in an active state, translocates to the nucleus and binds to the κB DNA elements and induces transcription of target genes.

As used herein "NF-κB pathway" refers to the stimuli that lead to modulation of activity of NF-κB. For example activation of the Toll-like receptor signaling, TNF receptor signaling, T cell receptor and B cell receptor signaling through either binding of a ligand or an antibody result in activation of NF-κB. Subsequently, phosphorylated NF-κB dimers bind to KB DNA elements and induce transcription of target genes. Exemplary KB DNA elements useful herein are referred to as "response element of the NF-κB pathway". Hence, a "receptor of the NF-κB pathway" refers to a receptor which can trigger the modulation of activity of NF-κB. Examples of a "receptor of the NF-κB pathway" are Toll-like receptors, TNF receptors, T cell receptor and B cell receptor. Non-limiting examples of antibodies that upon binding to its target result in modulation of the activity of NF-κB are anti-CD3 antibodies, anti-CD40 antibodies, anti-DR5 antibodies, anti-DR4 antibodies, anti-41BB antibodies, anti-Ox40 antibodies and anti-GITR antibodies. Examples of ligands that upon binding to its target result in modulation of the activity of NF-κB are OX40 ligand, 4-1BB ligand or CD40 ligand.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

Engineered antibodies with three or more functional antigen binding sites, including "Octopus antibodies", are also included herein (see, e.g. US 2006/0025576A1).

The antibody or fragment herein also includes a "Dual Acting FAb" or "DAF" (see, US 2008/0069820, for example).

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST. BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

"Protease" or "proteolytic enzyme" as used herein refers to any proteolytic enzyme that cleaves the linker at a recognition site and that is expressed by a target cell, e.g. by a tumor cell. Such proteases might be secreted by the target cell or remain associated with the target cell, e.g., on the target cell surface. Examples of proteases include but are not limited to metalloproteinases, e.g., matrix metalloproteinase 1-28 and A Disintegrin And Metalloproteinase (ADAM) 2, 7-12, 15, 17-23, 28-30 and 33, serine proteases, e.g., urokinase-type plasminogen activator and Matriptase, cysteine protease, aspartic proteases, and members of the cathepsin family.

"Protease-activatable" as used herein, with respect to the T cell activating bispecific molecule, refers to a T cell activating bispecific molecule having reduced or abrogated ability to activate T cells due to a masking moiety that reduces or abrogates the T cell activating bispecific molecule's ability to bind to CD3. Upon dissociation of the masking moiety by proteolytic cleavage. e.g., by proteolytic cleavage of a linker connecting the masking moiety to the T cell activating bispecific molecule, binding to CD3 is restored and the T cell activating bispecific molecule is thereby activated.

The term "protein with intrinsic fluorescence" refers to a protein capable of forming a highly fluorescent, intrinsic chromophore either through the cyclization and oxidation of internal amino acids within the protein or via the enzymatic addition of a fluorescent co-factor. The term "protein with intrinsic fluorescence" includes wild-type fluorescent proteins and mutants that exhibit altered spectral or physical properties. The term does not include proteins that exhibit weak fluorescence by virtue only of the fluorescence contribution of non-modified tyrosine, tryptophan, histidine and phenylalanine groups within the protein. Proteins with intrinsic fluorescence are known in the art, e.g. green fluorescent protein (GFP),), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Ormo et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) and can be measured e.g. by live cell imaging (e.g. Incucyte) or fluorescent spectrophotometry.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, a "reporter gene" means a gene whose expression can be assayed. In one preferred embodiment a "reporter gene" is a gene that encodes a protein the production and detection of which is used as a surrogate to detect indirectly the activity of the antibody or ligand to be tested. The reporter protein is that protein encoded by the reporter gene. Preferably, the reporter gene encodes an enzyme whose catalytic activity can be detected by a simple assay method or a protein with a property such as intrinsic fluorescence or luminescence so that expression of the reporter gene can be detected in a simple and rapid assay requiring minimal sample preparation. Non-limiting examples of enzymes whose catalytic activity can be detected are Luciferase, beta Galactosidase, Alkaline Phosphatase. Luciferase is a monomeric enzyme with a molecular weight (MW) of 61 kDa. It acts as a catalysator and is able to convert D-luciferin in the presence of Adenosine triphosphate (ATP) and Mg2+ to luciferyl adenylate. In addition, pyrophosphate (PPi) and adenosine monophosphate (AMP) are generated as byproducts. The intermediate luciferyl adenylate is then oxidized to oxyluciferin, carbon dioxide ($CO_2$) and light. Oxyluciferin is a bioluminescent product which can be quantitatively measured in a luminometer by the light released from the reaction. Luciferase reporter assays are commercially available and known in the art, e.g. Luciferase 1000 Assay System and ONE-Glo™ Luciferase Assay System.

"Reversibly concealing" as used herein refers to the binding of a masking moiety or idiotype-specific polypeptide to an antigen-binding moiety or molecule such as to prevent the antigen-binding moiety or molecule from its antigen, e.g., CD3. This concealing is reversible in that the idiotype-specific polypeptide can be released from the antigen-binding moiety or molecule, e.g., by protease cleavage, and thereby freeing the antigen-binding moiety or molecule to bind to its antigen.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Some of the bispecific antibodies molecules as described herein are capable of inducing T cell activation. Suitable assays to measure T cell activation are known in the art and described herein.

A "target cell antigen" as used herein refers to an antigenic determinant presented on the surface of a target cell, for example a cell in a tumor such as a cancer cell or a cell of the tumor stroma.

As used herein "target antigen" refers to any cell surface antigen that can be targeted by an antibody or fragment thereof. It also refers to the receptor that can be targeted by a ligand.

A "response element" refers to a specific transcription factor binding element, or cis acting element which can be activated or silenced on binding of a certain transcription factor. In one embodiment the response element is a cis-acting enhancer element located upstream of a minimal promotor (e.g. a TATA box promotor) which drives expression of the reporter gene upon transcription factor binding.

A "signal transducing cell surface receptor" as used herein is a cell surface receptor localized on the surface of reporter cells as described herein capable of transducing an extracellular signal, e.g. binding of an antigen binding moiety to the signal transducing cell surface receptor, to an intracellular signaling cascade resulting with expression of a reporter gene. Non-limiting examples of signal transducing cell surface receptors are Toll-like receptors, TNF receptors, T cell receptor and B cell receptor or recombinant versions or fragments thereof.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "valent" as used herein denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

Antibodies used in the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

II. Novel Assay

The inventor developed a robust assay suitable for high-throughput format which enables determination of antigen expression in tumors and/or functional activity of bispecific antibodies in tumor cells, particularly in primary tumor samples. Functionality of the antibody (e.g. the biological activity of an antibody such as the ability of an antibody to elicit a cellular response) is evaluated by using reporter cell lines which have a reporter gene expressed upon activation of a response element. In certain embodiment said reporter gene is selected from a gene encoding for a fluorescent protein (e.g. green fluorescent protein, GFP) and/or a gene encoding for an enzyme whose catalytic activity can be detected (e.g. Luciferase). Further provided herein are methods for determining the presence of a target antigen and/or protease expression in tumor samples as well as methods for selection of bispecific antibodies and for selection of protease-cleavable linkers for the treatment of a proliferative disease, particularly cancer.

In one embodiment provided is an in vitro method for determining the presence of a target antigen in a tumor sample comprising the steps of:
  i) providing a tumor sample;
  ii) providing reporter cells comprising a reporter gene under the control of a signal transducing cell surface receptor;
  iii) adding to the tumor sample a bispecific antibody comprising:
    a) a first antigen binding moiety capable of specific binding to a target antigen; and
    b) a second antigen binding moiety capable of specific binding to the signal transducing cell surface receptor;
  iv) adding the reporter cells to the tumor sample; and
  v) determining the presence of the target antigen by determining the expression of the reporter gene.

The target antigen can be an antigen expressed by the tumor cells, and is usually located on the cell surface of the tumor cells. In one embodiment, the target antigen is expressed by the tumor cells. In one embodiment the tumor cells naturally express the target antigen. In one embodiment, the target antigen is located on the surface of the tumor cells. In one embodiment, the target antigen is a cell surface receptor. Accordingly, the bispecific antibody binds to the target antigen on the cell surface of the tumor cells. In one embodiment, the target antigen is selected from the group consisting of CEA, Her2, TYRP, EGFR, MCSP, STEAP1, WT1 and FolR1. In one embodiment, the target antigen is FolR1.

However, the target antigen is not limited to proteins located on the cell surface but may also derive from polypeptides or proteins which are temporarily or permanently located intracellularly. In such cases, the target antigen deriving from an intracellular polypeptide or protein is presented on the cell surface, in particular on the cell surface of the tumor cells. In one embodiment, the target antigen is a peptide bound to a molecule of the major histocompatibility complex (MHC). In one embodiment, the MHC is human MHC. In one embodiment, the peptide bound to a molecule of the MHC has an overall length of between 8 and 100, preferably between 8 and 30, and more preferred between 8 and 16 amino acids. In one embodiment, the target antigen derives from a protein which is exclusively or mainly expressed in tumor tissue. In one embodiment, the protein is an intracellular protein and the peptide is generated by the MHC-I or MHC-II pathway and presented by a MHC class I or MHC class II complex. In one embodiment, the peptide is generated by the MHC-I pathway and presented by a MHC class I complex.

In one embodiment the tumor cells are mammalian cells, preferably human or primate cells. In one embodiment, the tumor cells derive from a tumor sample, in particular from a biopsy from a patient. In one embodiment, the tumor sample is a biopsy from a human patient. In one embodiment, the tumor cells bear the target antigenic determinant. In one embodiment, the tumor cells derive from a patient suffering from a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. In one embodiment, the tumor cells derive from a biopsy of a human patient. In one embodiment, the tumor sample is a biopsy of a human patient. The tumor sample can be assessed without dissociation of the tumor sample or tumor tissue into single cells. In one embodiment, the tumor sample is not digested prior to determining the presence of a target antigen according to the method of the present invention. In one embodiment, the tumor sample is cut, in particular using a razor blade. In another embodiment, the tumor sample is digested prior to determining the presence of a target antigen according to the method of the present invention. In one embodiment, the tumor sample is digested, in particular by collagenase or hyaluronidase.

Upon or after binding of the first antigen binding moiety to the target antigen, the bispecific antibody binds to the signal transducing cell surface receptor on the reporter cells wherein the response element activates the expression of the reporter gene. Accordingly, the reporter gene in the reporter cells is expressed upon binding of the first antigen binding moiety to the target antigen and binding of the signal transducing cell surface receptor to the reporter cells. In one embodiment, the expression of the reporter gene is indicative for binding of the first antigen binding moiety to the target antigen. Surprisingly, no expression or only very low expression of the reporter gene occurs without binding of the first antigen binding moiety to the target antigen on the tumor cells. The binding of the bispecific antibody to the target antigen can be determined qualitatively, i.e. by the presence or absence of the expression of the reporter gene; with the absence of any fluorescence or luminescence being indicative of no binding. Usually the absence of reporter gene expression is defined by a certain threshold, i.e. after deduction of any background signal. The background signal is usually determined by performing the assay with all reagents but the antibody to be tested or in absence of the tumor cells. In further embodiments, the binding of the antibody or ligand to the target antigen can be determined quantitatively, i.e. the level or strength of binding can be determined with the method according to the invention. Towards this end the antibody is tested in different concentrations and the half maximal effective concentration (EC50) is determined. EC50 refers to the concentration of the antibody or ligand at which the antibody binds halfway between the baseline and maximum after a specified exposure time. The EC50 of the dose response curve therefore represents the concentration of the antibody where 50% of its maximal binding is observed. The KD (dissociation constant) can be calculated from the dose response curve by methods known in the art.

In one embodiment, the bispecific antibody binds to the signal transducing cell surface receptor. The binding of the antibody to the signal transducing cell surface receptor elicits a cellular response which results in a modulation of the activity of the response element, either directly or through a cascade of cell signalling. The response element is a DNA element which can be silenced or activated by transcription factors or the like. Response elements are known in the art and are commercially available, e.g. in reporter vectors. Usually the response element comprises DNA repeat elements and is a cis-acting enhancer element located upstream of a minimal promotor which drives expression of a reporter gene upon transcription factor binding. Examples for response elements and their transcription factors useful herein are mentioned in the below table:

| Transcription factor/Response element | Description |
| --- | --- |
| AP1(1) | Monitoring induction of the activator protein 1(AP) and the stress-activated protein kinase/Jun N-terminal kinase (SAPK/JNK) signal transduction pathway. |
| AP1(2) | Monitoring the induction of the protein kinase C (PKC) signal transduction pathway, as well as related pathways such as the MAPK pathway. |
| AP3 | Measuring transcriptional activity of activator protein 3. |
| AR | Measuring transcriptional activity of androgen receptor. The androgen receptor functions as a steroid-hormone activated transcription factor. Upon binding the hormone ligand, the receptor dissociates from accessory proteins, translocates into the nucleus, dimerizes, and then stimulates transcription of androgen responsive genes. |

-continued

| Transcription factor/Response element | Description |
|---|---|
| CRE(1) | Measuring transcriptional activity of cAMP binding protein (CREB). Several signal transduction pathways are associated with the cAMP response element (CRE), including Jun N-terminal kinase (JNK), p38, and protein kinase A (PKA). Induction of these pathways enables endogenous transcription factors, such as CREB or ATF, to bind CRE. |
| E2F(1) | Measuring transcriptional activity of E2F transcription factor family, including E2F1, E2F2, E2F3, E2F4, E2F5. The E2F protein family plays a crucial role in the control of cell cycle and action of tumor suppressor proteins and is also a target of the transforming proteins of small DNA tumor viruses. These proteins bind preferentially to retinoblastoma protein pRB and mediate both cell proliferation and p53-dependent/independent apoptosis. |
| ELK1 | Measuring transcriptional activity of ELK1. ELK1 is a member of the Ets family of transcription factors and of the ternary complex factor (TCF) subfamily. Proteins of the TCF subfamily form a ternary complex by binding to the serum response factor and the serum reponse element in the promoter of the c-fos proto-oncogene. ELK1is a nuclear target for the ras-raf-MAPK signaling cascade. |
| ER | Measuring the induction of the estrogen response element (ERE). Binding of the activated estrogen receptor to the cis-acting ERE enhancer element induces transcription and activates the luciferase reporter gene. |
| GAS (interferon-gamma activation sequence) | Monitoring the induction of STAT1, a component of JAK/STAT-mediated signal transduction pathways. Cytokines bind and induce receptor dimerization at the cell surface, causing the receptor itself to be phosphorylated. The phosphorylated receptor then acts as a docking site for STAT1. STAT1 is phosphorylated, dimerizes and translocates to the nucleus to regulate transcription. |
| GATA | Measuring transcriptional activity of globin transcription factor (GATA) family. The GATA family of transcription factors contains six zinc-finger binding proteins that regulate differentiation and cell proliferation. GATA family members are involved in hematopoietic, cardiac and gut development. |
| GR | Monitoring the induction of the glucocorticoid response element (GRE) and the glucocorticoid-mediated signaling transduction pathway. |
| HIF-1 | Measuring transcriptional activity of hypoxia inducible factor-1 (HIF-1). HIF-1 binds to the hypoxia-response element and activates genes involved in angiogenesis, glucose metabolis, cell proliferation/survival and invasion/metastasis. |
| HSE | Monitoring the activation of heat shock factor (HSF) and heat shock-mediated signal transduction pathways. |
| IRF-1 | Measuring transcriptional activity of interferon regulatory factor 1. IRF1 is a member of the interferon regulatory transcription factor (IRF) family. IRF1 serves as an activator of interferons alpha and beta transcription, and in mouse it has been shown to be required for double-stranded RNA induction of these genes. |
| ISRE | Monitoring the induction of the STAT1 and STAT2 components of Jak/STAT-mediated signal transduction pathways. Signaling molecules, including type I (IFN-a and -b) and type II (IFN-g) interferons, induce signaling by binding receptors and causing receptor dimerization at the cell surface. This dimerization causes the receptor itself to be phosphorylated and act as a docking site for transcription factors, including STAT1 and STAT2. The STAT proteins are then phosphorylated, dimerize and translocate to the nucleus, where the STAT1 and STAT2 heterodimer regulates transcription by binding to the IFN-stimulated response element (ISRE). |
| MEF-1 | Measuring transcriptional activity of myogenic factor 3 (MYOD1). |
| MEF-2 | Measuring transcriptional activity MADS box transcription enhancer factor 2A, 2B, 2C and 2D. |
| MEF-3 | Monitoring the activation of myelin gene expression factor 3. |
| NFAT | Monitoring the induction of nuclear factor of activated T-cells (NFAT)-mediated signal transduction pathways. Several pathways are associated with the NFAT enhancer element, including calcineurin and protein kinase C. |
| NFκB | Monitoring the activation of the nuclear factor of kappa light polypeptide gene enhancer in B-cells (NFκB) signal transduction pathway. NFκB is a transcription regulator that is activated by various intra- and extra-cellular stimuli such as cytokines, oxidant-free radicals, ultraviolet irradiation, and bacterial or viral products. Activated NFκB translocates into the nucleus and stimulates the expression of genes involved in a wide variety of biological functions. |
| p53 | Monitoring p53-mediated signal transduction pathways. p53 is a tumor suppressor that plays a crucial role in a number of cellular processes, including the suppression of cell proliferation after DNA damage. |
| PR | Monitoring the induction of progesterone receptor. |
| RAR | Monitoring the induction of the retinoic acid response element (RARE). |

| Transcription factor/Response element | Description |
|---|---|
| RXR | Monitoring the activation of retinoid X receptors (RXR) and RXR-mediated signal transduction pathway. Retinoid X receptors (RXRs) and retinoic acid receptors (RARs) are nuclear receptors that mediate the biological effects of retinoids by their involvement in retinoic acid-mediated gene activation. These receptors exert their action by binding, as homodimers or heterodimers, to specific sequences in the promoters of target genes and regulating their transcription. |
| Smad | Measuring transcriptional activity of a family of Mad-related transcription factors. |
| Sp1 | Measuring transcriptional activity of Sp1. Sp1 is a sequence-specific transcription factor that recognizes 5'-GGGGCGGGGC-3' and closely related sequences, which are often referred to as GC boxes. Sp1 was initially identified as a HeLa cell derived factor that selectively activates in vitro transcription from the SV40 promoter and binds to the multiple GC boxes in the 21-bp repeated elements in SV40. Sp1 has been described as a ubiquitous transcription factor that is required for the constitutive and inducible expression of a variety of genes, such as in cell cycle or mammalian development. |
| SRE | Monitoring the induction of the serum response element (SRE) and the mitogen-activated protein (MAP) kinase signal transduction pathway. |
| SRF | Monitoring the induction of serum response factor (c-fos serum response element-binding transcription factor). |
| Stat1 p84/p91 | Measuring transcriptional activity of signal transducer and activator of transcription 1. Stat1 is a member of the STAT protein family. In response to cytokines and growth factors, STAT family members are phosphorylated by the receptor associated kinases, and then form homo- or heterodimers that translocate to the cell nucleus where they act as transcription activators. This protein can be activated by various ligands including interferon-alpha, interferon-gamma, EGF, PDGF and IL-6. |
| Stat4 | Measuring transcriptional activity of signal transducer and activator of transcription 4. Stat4 protein encoded by this gene is a member of the STAT family of transcription factors. In response to cytokines and growth factors, STAT family members are phosphorylated by the receptor associated kinases, and then form homo- or heterodimers that translocate to the cell nucleus where they act as transcription activators. This protein is essential for mediating responses to IL-12 in lymphocytes, and regulating the differentiation of T helper cells. |
| VDR | Measuring transcriptional activity of vitamin D receptor. VDR is a member of the steroid receptor superfamily. In its ligand bound state, VDR forms heterodimers with RXR and regulates gene expression by binding to specific hormone response elements. The VDR-RXR heterodimer has been shown to bind to VD-responsive elements (VDRE) of osteocalcin and osteopontin genes to stimulate transcription of these genes. |
| YY1 | Measuring transcriptional activity of YY1. YY1 is a ubiquitously distributed transcription factor belonging to the GLI-Kruppel class of zinc finger proteins. The protein is involved in repressing and activating a diverse number of promoters. YY1 may direct histone deacetylases and histone acetyltransferases to a promoter in order to activate or repress the promoter, thus implicating histone modification in the function of YY1. |

Binding of the bispecific antibody to the signal transducing cell surface receptor activates the response element. In one embodiment the response element is a nuclear response element located in the nucleus of the cell. In another embodiment said response element is located on a plasmid in the reporter cell. In one embodiment the assay comprises the preliminary step of transfection of the reporter cells with an expression vector comprising the DNA sequence coding for the reporter gene under the control of the response element. Additionally, the reporter cells can be transfected with an expression vector comprising the DNA sequence coding for the signal transducing cell surface receptor. The reporter cells can be transfected with an expression vector comprising all elements of the signaling cascade or with different vectors individually expressing the different components. In one embodiment, the reporter cells comprise the DNA sequence coding for the reporter gene under the control of the response element, and the DNA sequence coding for signal transducing cell surface receptor.

In one embodiment the reporter gene is selected from a gene coding for a fluorescent protein or a gene coding for an enzyme whose catalytic activity can be detected. In one embodiment, the reporter gene is coding for a fluorescent or a luminescent protein. In one embodiment, the reporter gene is coding for green fluorescent protein (GFP) or luciferase. In further embodiments the fluorescent protein is selected from the group consisting of green fluorescent protein (GFP), yellow fluorescent protein (YFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Ormo et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) enhanced green fluorescent protein (EGFP) and can be measured e.g. by live cell imaging (e.g. Incucyte) or fluorescent spectrophotometry. In one embodiment the enzyme whose catalytic activity can be detected is selected from the group consisting of luciferase, beta Galactosidase, Alkaline Phosphatase. In one embodiment the reporter gene is encoding for GFP. In one embodiment the reporter gene is encoding for luciferase. The activity of luciferase can be detected by commercially available assays, e.g. by Luciferase 1000 Assay System (or ONE-Glo™ Luciferase Assay System (both Promega). The Luciferase 1000 Assay System contains coenzyme A (CoA) besides luciferin as a substrate, resulting in a strong light intensity lasting for at least one minute. For assaying the intracellular luciferase, it is necessary to lyse the cells prior to detection. Therefore, a cell lysis buffer was provided separately to the Luciferase 1000 assay system. In comparison, the ONE-Glo™ Luciferase Assay System combines the Luciferase substrate with a cell lysis reagent and also shows a more stable signal. The light which is produced as a by-product of the reaction is collected by the luminometer from the entire visible spectrum. In the examples shown herein the signal was proportional to the amount of produced luciferase and therefore proportional to the strength of the activation of the NFκB promotor. In another embodiment a Luciferase assay is used wherein the luciferase is secreted from the cells. Hence the assay can be performed without lysis of the cells.

Accordingly, as described herein, the signal transducing cell surface receptor is functionally linked to a response element. In one embodiment, the response element controls the expression of the reporter gene. In one embodiment the signal transducing cell surface receptor and the response element are part of the NF-κB pathway. In one embodiment the signal transducing cell surface receptor is selected from Toll-like receptors, TNF receptors, T cell receptors and B cell receptors; as well as recombinant forms and fragments thereof. Non-limiting examples of antibodies that upon binding to its target result in modulation of the activity of NF-κB are anti-CD3 antibodies, anti-CD40 antibodies, anti-DR5 antibodies, anti-DR4 antibodies, anti-41BB antibodies, anti-Ox40 antibodies and anti-GITR antibodies. In one embodiment the response element is a NF-κB response element. In one embodiment said response element comprises one or more of the following DNA repeats

```
                        (SEQ ID NO: 68)
       GGGAATTTCC, (SEQ ID NO: 69)
       GGGGACTT TCC, (SEQ ID NO: 70)
       GGGACTTTCC, (SEQ ID NO: 71)
       GGGACTTCC, (SEQ ID NO: 72)
       ATTGTAGCGTA.
```

In one embodiment said response element comprises 3 to 6, 3 or 6 of the DNA repeats mentioned above. In one embodiment said response element comprises 3 to 6, 3 or 6 of the DNA repeats mentioned above and 1, 2, 3 or 4 additional nucleotides.

In one embodiment said response element comprises a DNA sequence of

```
                                     (SEQ ID NO: 73)
GGGAATTT CCGGGGACTT TCCGGGAATTTCCGGGGACT
TTCCGGGAATTTCC,
```

```
                                     (SEQ ID NO: 74)
GGGAATTTCCGGGAATTTCCGGGAATTTCCGGGAATTTCCGGGAATTTC
CGGGAATTTCC, (SEQ ID NO: 75)
GGGACTTCCGGGACTTTCCGGGACTTTCCGGGACTTTCCGGGACTTTCC
GGGACTTTCC
or (SEQ ID NO: 76)
GGGACTTTCCATTGTAGCGTAGGGACTTTCCATTGTAGCGTAGGGCTTT
CCATTGTAGCGTAGGGCTTTCC.
```

In one embodiment, the reporter cells comprise at least one DNA repeat with a DNA sequence of SEQ ID NO: 68, 69, 70, 71 or 72, wherein the DNA repeat is operatively linked to the reporter gene and wherein the reporter gene is expressed upon binding of the second antigen binding moiety to the signal transducing cell surface receptor.

In one embodiment the steps iii) and iv) are performed consecutively or simultaneously.

As described herein, the expression of the reporter gene can be directly correlated with the functionality of the antibody to be tested. For example when using a gene encoding for a fluorescent protein or a gene encoding for luciferase as a reporter gene, the amount of light detected from the cells correlates directly with the target antigen binding of the antibody to be tested. In one embodiment the antibody is tested in different concentrations and the half maximal effective concentration (EC50) of reporter gene activation or inhibition is determined. EC50 refers to the concentration of the antibody or ligand at which the antibody or ligand activates or inhibits the reporter gene halfway between the baseline and maximum after a specified exposure time. The EC50 of the dose response curve therefore represents the concentration of the antibody where 50% of its maximal activating or inhibitory effect on the target antigen is observed.

The novel assay as described herein is robust, suitable for use in high-throughput format and efficient in terms of hands-on time needed to accomplish the assay. Furthermore, the assay of the present invention tolerates the presence of dead cells in the sample to be analyzed. This is in contrast to cell assays wherein the binding and functionality of an antibody is determined by measuring cell viability or cell death, e.g. a killing assay.

In one embodiment, the sample to be assayed contains dead cells. In one embodiment, the sample to be assayed is a tumor sample, in particular a biopsy of a tumor. In one embodiment, the tumor sample contains dead cells, in particular more than 10% of dead cells. In further embodiment, the tumor sample contains more than 20%, more than 30%, more than 40% or more than 50% dead cells. Methods to determine the number of dead cells in a cell culture or tissue are well known in the art, as e.g. propidium iodide staining.

One further advantage of the new assay described herein is that no washing steps are required. The antibodies to be tested and the reporter cells can be added to the tumor samples in either order or at the same time. In one embodiment, the antibody is diluted in cell culture medium and the tumor sample is added to the cell culture medium containing the diluted antibody in a suitable cell culture format, e.g., in a well of a 24 well plate or in a well of a 96 well plate. Preferably the testing medium is a medium that provides conditions for cells to be viable for up to 48 hours. Suitable media are for example Jurkat medium, as outlined in the examples. In one embodiment the assay is performed in a microtiterplate. In one embodiment the microtiterplate is suitable for high throughput screening. The assay of the present invention can be performed in any format that allows for rapid preparation, processing, and analysis of multiple reactions. This can be, for example, in multi-well assay plates (e.g., 24 wells, 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting fluorescent and/or luminescent signals. In one embodiment about 100000 to about 1000000 reporter cells per well of a 24-well plate are provided in step ii). In a preferred embodiment about 300000 to about 700000 cells or about 400000 to about 600000 reporter cells per well of a 24-well plate are provided. In one embodiment about 500000 reporter cells per well of a 24-well plate are provided in step ii). In one embodiment about 10000 to about 100000 cells per well of a 96-well plate are provided in step ii). In a preferred embodiment about 30000 to about 700000 cells or about 40000 to about 60000) cells per well of a 96-well plate are provided. In one embodiment about 50000 reporter cells per well of a 96-well plate are provided in step ii). In one embodiment about 200000 to about 2000000 cells per ml of cell culture medium are provided in step ii). In a preferred embodiment about 600000 to about 1400000 cells or about 800000 to about 1200000 cells per ml of cell culture medium are provided. In one embodiment about 1000000 cells per ml of cell culture medium are provided in step ii).

In one embodiment the antibody is provided in step iii) to achieve a final concentration of about 0.001 μg/ml to 10 μg/ml. In further embodiments the antibody is provided in step iii) to achieve a final concentration of about 0.05 μg/ml to about 2 μg/ml or about 0.1 μg/ml to about 1 μg/ml. In further embodiments the antibody is provided in step iii) to achieve a final concentration of about 0.5 μg/ml. In one embodiment the antibody is provided in step iii) to achieve a final concentration of about 1 nM to about 1000 nM. In further embodiments the antibody is provided in step iii) to achieve a final concentration of about 5 nM to about 200 nM or about 10 nM to about 100 nM. In further embodiments the antibody is provided in step iii) to achieve a final concentration of about 50 nM. The antibody can be diluted in cell culture medium. e.g. in Jurkat medium as described in the example section. The antibody diluted to the final concentration as described herein is added to the tumor sample before or after adding the reporter cells. In one embodiment, the antibody diluted to the final concentration as described herein is added to the tumor sample before adding the reporter cells. In one embodiment, the tumor samples are provided in cell culture inserts. In one embodiment, the tumor samples are embedded in Matrigel.

In certain embodiments the bispecific molecule of the invention binds to CD3. In one specific embodiment the bispecific antibody comprises
(a) a first antigen binding moiety which is a Fab molecule capable of specific binding to a target cell antigen;
(b) a second antigen binding moiety which is a Fab molecule capable of specific binding to CD3.

In one specific embodiment the bispecific antibody comprises
(a) a first antigen binding moiety which is a Fab molecule capable of specific binding to a target cell antigen;
(b) a second antigen binding moiety which is a Fab molecule capable of specific binding to CD3, and which comprises at least one heavy chain complementarity determining region (CDR) selected from the group consisting of SEQ ID NO: 11, SEQ ID NO: 12 and SEQ ID NO: 13 and at least one light chain CDR selected from the group of SEQ ID NO: 17, SEQ ID NO: 18, SEQ ID NO: 19.

In one embodiment, the target antigen is a cell surface receptor. In one embodiment, the target antigen is selected from the group consisting of CEA. Her2, TYRP. EGFR, MCSP. STEAP1, WT1 and FolR1. In one embodiment, the target antigen is FolR1. In one embodiment the bispecific antibody comprises
(a) a first antigen binding moiety which is a Fab molecule capable of specific binding to FolR1 comprising at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19;
(b) a second antigen binding moiety which is a Fab molecule capable of specific binding to CD3, and which comprises at least one heavy chain complementarity determining region (CDR) selected from the group consisting of SEQ ID NO: 11, SEQ ID NO: 12 and SEQ ID NO: 13 and at least one light chain CDR selected from the group of SEQ ID NO: 17, SEQ ID NO: 18, SEQ ID NO: 19.

In one embodiment the bispecific antibody comprises
(a) a second antigen binding moiety which is a Fab molecule capable of specific binding to FolR1 comprising heavy chain variable region comprising an amino acid sequence that is at least about 95%, 96%, 97%, 98%, 99% or 100% identical to the amino acid sequence of SEQ ID NO: 27 and a light chain variable region comprising an amino acid sequence that is at least about 95%, 96%, 97%, 98%, 99% or 100% identical to the amino acid sequence of SEQ ID NO: 28; and
(b) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 26 and a light chain variable region comprising an amino acid sequence that is at least about 95%, 96%, 97%, 98%, 99% or 100% identical to the amino acid sequence of SEQ ID NO: 28.

In several embodiments, the bispecific antibody comprises an Fc domain composed of a first and a second subunit capable of stable association. In some embodiments, the first antigen binding moiety is fused at the C-terminus of the Fab heavy chain to the N-terminus of the first or the second subunit of the Fc domain.

In one such embodiment, the second antigen binding moiety is fused at the C-terminus of the Fab heavy chain to the N-terminus of the Fab heavy chain of the first antigen binding moiety. In a specific such embodiment, the bispecific antibody essentially consists of a first and a second antigen binding moiety, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first or the second subunit of the Fc domain. In one embodiment, the Fab light chain of the second antigen binding moiety and the Fab light chain of the first antigen binding moiety may additionally be fused to each other, optionally via a peptide linker.

In another embodiment, the second antigen binding moiety is fused at the C-terminus of the Fab heavy chain to the N-terminus of the first or second subunit of the Fc domain. In a specific such embodiment, the bispecific antibody essentially consists of a first and a second antigen binding moiety, an Fc domain composed of a first and a second subunit, and optionally one or more peptide linkers, wherein the first and the second antigen binding moiety are each fused at the C-terminus of the Fab heavy chain to the N-terminus of one of the subunits of the Fc domain In other embodiments, the second antigen binding moiety is fused at the C-terminus of the Fab heavy chain to the N-terminus of the first or second subunit of the Fc domain. In a particular such embodiment, the first antigen binding moiety is fused at the C-terminus of the Fab heavy chain to the N-terminus of the Fab heavy chain of the second antigen binding moiety. In a specific such embodiment, the bispecific antibody essentially consists of a first and a second antigen binding moiety, an Fc domain composed of a first and a second subunit, and optionally one or more peptide linkers, wherein the first antigen binding moiety is fused at the C-terminus of the Fab heavy chain to the N-terminus of the Fab heavy chain of the second antigen binding moiety, and the second antigen binding moiety is fused at the C-terminus of the Fab heavy chain to the N-terminus of the first or the second subunit of the Fc domain. Optionally, the Fab light chain of the second antigen binding moiety and the Fab light chain of the first antigen binding moiety may additionally be fused to each other.

In one embodiment, the first and the second antigen binding moieties are conventional Fab molecules comprising a common light chain. In one embodiment, the second antigen binding moiety is fused at the C-terminus of the Fab heavy chain to the N-terminus of the Fab heavy chain of the first antigen binding moiety, optionally via a peptide linker. In one embodiment, the Fab light chain of the first antigen binding moiety and the Fab light chain of the second antigen binding moiety are fused to each other, optionally via a peptide linker.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally a number between 1 and 10, typically between 2 and 4. A particularly suitable peptide linker for fusing the Fab light chains of the first and the second antigen binding moiety to each other is $(G_4S)_2$. Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

A bispecific antibody with a single antigen binding moiety capable of specific binding to a target cell antigen is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have a bispecific antibody comprising two or more antigen binding moieties specific for a target cell antigen, for example to optimize targeting to the target site.

Accordingly, in certain embodiments, the bispecific antibody used according to the invention further comprises a third antigen binding moiety capable of specific binding to a target cell antigen. In further embodiments, the third antigen binding moiety is a conventional Fab molecule, or a crossover Fab molecule wherein either the variable or the constant regions of the Fab light chain and the Fab heavy chain are exchanged. In one embodiment, the third antigen binding moiety is capable of specific binding to the same target cell antigen as the first antigen binding moiety. In a particular embodiment, the second antigen binding moiety is capable of specific binding to CD3, and the first and third antigen binding moieties are capable of specific binding to a target cell antigen. In a particular embodiment, the first and the third antigen binding moiety are identical (i.e. they comprise the same amino acid sequences).

In a particular embodiment, the second antigen binding moiety is capable of specific binding to CD3, and the first and third antigen binding moieties are capable of specific binding to FolR1, wherein the first and third antigen binding moieties comprise at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In a particular embodiment, the second antigen binding moiety is capable of specific binding to CD3, and comprises at least one heavy chain complementarity determining region (CDR) selected from the group consisting of SEQ ID NO: 11, SEQ ID NO: 12 and SEQ ID NO: 13 and at least one light chain CDR selected from the group of SEQ ID NO: 17, SEQ ID NO: 18, SEQ ID NO: 19; and the first and third antigen binding moieties are capable of specific binding to FolR1, wherein the first and third antigen binding moieties comprise at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In a particular embodiment, the second antigen binding moiety which is a Fab molecule capable of specific binding to CD3, comprising the heavy chain complementarity determining region (CDR) 1 of SEQ ID NO: 11, the heavy chain CDR 2 of SEQ ID NO: 12, the heavy chain CDR 3 of SEQ ID NO: 13, the light chain CDR 1 of SEQ ID NO: 17, the light chain CDR 2 of SEQ ID NO: 18 and the light chain CDR 3 of SEQ ID NO: 19, wherein the first antigen binding moiety is a crossover Fab molecule wherein either the variable or the constant regions, particularly the constant regions, of the Fab light chain and the Fab heavy chain are exchanged; and the first and third antigen binding moiety each of which is a Fab molecule capable of specific binding to FolR1 comprising the heavy chain CDR 1 of SEQ ID NO: 14, the heavy chain CDR 2 of SEQ ID NO: 15, the heavy chain CDR 3 of SEQ ID NO: 16, the light chain CDR 1 of SEQ ID NO: 17, the light chain CDR 2 of SEQ ID NO: 18 and the light chain CDR3 of SEQ ID NO: 19.

In a particular embodiment, the second antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 26 and a light chain variable region comprising an amino acid sequence that is at least about 95%, 96%, 97%, 98%, 99% or 100% identical to the amino acid sequence of SEQ ID NO: 28, and the first and third antigen binding moieties are capable of specific binding to FolR1, wherein the second and third antigen binding moieties comprise a heavy chain variable region comprising an amino acid sequence that is at least about 95%, 96%, 97%, 98%, 99% or 100% identical to the amino acid sequence of SEQ ID NO: 27 and a light chain variable region comprising an amino acid sequence that is at least about 95%, 96%, 97%, 98%, 99% or 100% identical to the amino acid sequence of SEQ ID NO: 28.

The Fc domain of the bispecific antibodies used according to the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the bispecific antibodies used according to the invention comprises not more than one Fc domain.

In one embodiment the Fc domain of the bispecific antibody is an IgG Fc domain. In one embodiment, the Fc domain is an IgG1 or IgG4, Fc domain In a particular embodiment the Fc domain is an IgG1 Fc domain. In another embodiment the Fc domain is an IgG4 Fc domain. In a more specific embodiment, the Fc domain is an IgG4 Fc domain comprising an amino acid substitution at position S228 (Kabat numbering), particularly the amino acid substitution S228P. This amino acid substitution reduces in vivo Fab arm exchange of IgG4 antibodies (see Stubenrauch et al., Drug Metabolism and Disposition 38, 84-91 (2010)). In a further embodiment the Fc domain is a human Fc domain.

Bispecific antibodies used according to the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity bispecific antibodies in recombinant production, it will thus be advantageous to introduce in the Fc domain of the bispecific antibodies a modification promoting the association of the desired polypeptides.

Accordingly, in particular embodiments the Fc domain of the bispecific antibodies used according to the invention comprise a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g., in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in a particular embodiment, in the CH3 domain of the first subunit of the Fc domain of the bispecific antibody an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g., by site-specific mutagenesis, or by peptide synthesis. In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A). In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In a particular embodiment the antigen binding moiety capable of binding to CD3 is fused (optionally via the antigen binding moiety capable of binding to the target cell antigen) to the first subunit of the Fc domain (comprising the "knob" modification).

In an alternative embodiment a modification promoting association of the first and the second subunit of the Fc domain comprises a modification mediating electrostatic steering effects, e.g., as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

In one embodiment, the bispecific antibody of step iii) additionally comprises c) a masking moiety covalently attached to the second antigen binding moiety through a protease-cleavable linker, wherein the masking moiety is capable of specific binding to the idiotype of the second antigen binding moiety thereby reversibly concealing the second antigen binding moiety. Such constructs are referred to as being "protease activatable" since the second antigen binding moiety will only be unconcealed upon cleavage of the protease-cleavable linker by a protease. In one embodiment, the protease is expressed by the tumor sample. In one embodiment the protease capable of cleaving the protease-cleavable linker is selected from the group consisting of metalloproteinase, e.g., matrix metalloproteinase (MMP) 1-28 and A Disintegrin And Metalloproteinase (ADAM) 2, 7-12, 15, 17-23, 28-30 and 33, serine protease. e.g., urokinase-type plasminogen activator and Matriptase, cysteine protease, aspartic protease, and cathepsin protease. In one specific embodiment the protease is MMP9 or MMP2. In a further specific embodiment, the protease is Matriptase. Expression of protease is known in the art to be indicative of malignant tumors. Accordingly, in one embodiment, protease expression is indicative for a malignant tumor. In one embodiment, the reporter gene is expressed by the reporter cells upon binding of the first antigen binding moiety to the target antigen on the tumor cells in the tumor sample and cleavage of the protease-cleavable linker by a protease expressed by the tumor cells and subsequent binding of the second antigen binding moiety to the signal transducing cell surface receptor. Upon cleavage of the linker, the second antigen binding moiety is revealed and binds to the signal transducing cell surface receptor, wherein expression of the reporter gene initiated. Accordingly, expression of the reporter gene is indicative for target antigen and protease expression in the tumor, wherein protease expression is indicative for a malignant tumor.

In one embodiment, the anti-idiotype masking moiety binds to the idiotype of the second antigen binding moiety. In one embodiment, the anti-idiotype masking moiety has a KD of about 1 nM to about 8 nM, in particular as determined by Surface Plasmon Resonance (SPR). In one embodiment, anti-idiotype mask has a KD of about 2 nM at 37° C. as determined by SPR. In one specific embodiment, the masking moiety recognizes the idiotype of the second antigen binding moiety capable of specific binding to a CD3, e.g., a human CD3. In one specific embodiment, the masking moiety recognizes the idiotype of the second antigen binding moiety capable of binding to a target cell antigen.

In one embodiment, the second antigen binding moiety is capable of specific binding to CD3. The second antigen binding moiety capable of specific binding to CD3 comprises an idiotype. In one embodiment, the masking moiety of the protease-activatable T cell activating bispecific molecule is covalently attached to the second antigen binding moiety. In one embodiment the masking moiety is covalently attached to the heavy chain variable region of the second antigen binding moiety. In one embodiment the masking moiety is covalently attached to the light chain variable region of the second antigen binding moiety. This covalent bond is separate from the specific binding, which is preferably non-covalent, of the masking moiety to the idiotype first antigen binding site. The idiotype of the second antigen binding moiety comprises its variable region. In one embodiment the masking moiety binds to amino acid residues that make contact with CD3 when the second antigen biding moiety is bound to CD3. In a preferred embodiment, the masking moiety is not the cognate antigen or fragments thereof of the second antigen binding moiety, i.e., the masking moiety is not a CD3 or fragments thereof. In one embodiment the masking moiety is an anti-idiotypic antibody or fragment thereof. In one embodiment, the masking moiety is an anti-idiotypic scFv. Exemplary embodiments of masking moieties which are anti-idiotypic scFv, and protease activatable T cell activating molecules comprising such masking moieties, are described in detail in the examples.

In one embodiment, the masking moiety masks a CD3-binding moiety and comprises at least one of the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25. In one embodiment, the masking moiety comprises the heavy chain CDR1 of SEQ ID NO: 20, the heavy chain CDR2 of SEQ ID NO: 21, the heavy chain CDR3 of SEQ ID NO: 22, the light chain CDR 1 of SEQ ID NO: 23, the light chain CDR2 of SEQ ID NO: 24, and the light chain CDR3 of SEQ ID NO: 25.

In one embodiment the idiotype-specific polypeptide is an anti-idiotype scFv. In one embodiment the idiotype-specific polypeptide is covalently attached to the molecule through a linker. In one embodiment the idiotype-specific polypeptide is covalently attached to the molecule through more than one linker. In one embodiment the idiotype-specific polypeptide is covalently attached to the molecule through two linkers. In one embodiment the linker is a peptide linker. In one embodiment the linker is a protease-cleavable linker. In one embodiment, the protease-cleavable linker comprises the sequence of SEQ ID NO: 30, 31, 32, 33, 34, 35, 36, 37, 38, 39, 40, 41, 42, 43 or 44. In one embodiment the protease-cleavable linker comprises at least one protease recognition site.

In one embodiment, the protease recognition site comprises the polypeptide sequence of SEQ ID NO: 45, 46, 47, 48, 49, 50, 51, 52, 53, 54, 55, 56, 57, 58 or 59.

In one embodiment the protease cleavable linker comprises a protease recognition sequence. In one embodiment the protease recognition sequence is selected from the group consisting of:

a)
(SEQ ID NO: 45)
RQARVVNG;

b)
(SEQ ID NO: 46)
VHMPLGFLGPGRSRGSFP;

c)
(SEQ ID NO: 47)
RQARVVNGXXXXXVPLSLYSG;

d)
(SEQ ID NO 48)
RQARVVNGVPLSLYSG;

e)
(SEQ ID NO: 49)
PLGLWSQ;

f)
(SEQ ID NO: 50)
VHMPLGFLGPRQARVVNG;

g)
(SEQ ID NO: 51)
FVGGTG;

h)
(SEQ ID NO: 52)
KKAAPVNG;

i)
(SEQ ID NO: 53)
PMAKKVNG;

j)
(SEQ ID NO: 54)
QARAKVNG;

k)
(SEQ ID NO: 55)
VHMPLGFLGP;

-continued l)

QARAK;    (SEQ ID NO: 56)

m)

VHMPLGFLGPPMAKK;    (SEQ ID NO: 57)

n)

KKAAP;    (SEQ ID NO: 58)

and o)

PMAKK,    (SEQ ID NO: 59)

wherein X is any amino acid.

In one embodiment the protease is selected from the group consisting of metalloproteinase, e.g., matrix metalloproteinase (MMP) 1-28 and A Disintegrin And Metalloproteinase (ADAM) 2, 7-12, 15, 17-23, 28-30 and 33, serine protease, e.g., urokinase-type plasminogen activator and Matriptase, cysteine protease, aspartic protease, and cathepsin protease. In one embodiment, the protease is selected from the group consisting of metalloproteinase, serine protease, cysteine protease, aspartic proteases, and cathepsin protease. In one embodiment, the protease is a metalloproteinase. In one embodiment the metalloproteinase is a matrix metalloproteinase (MMP), in particular MMP9 or MMP2. In one embodiment, the protease is a serine protease. In one embodiment, the serine protease is Matriptase. Accordingly, in one embodiment, a protease cleaves the protease-cleavable linker, wherein the second antigen binding moiety is unconcealed. In one embodiment, the protease as described herein is expressed by the tumor cells. In one embodiment, the protease is expressed in the tumor sample, in particular in the biopsy as described herein. In one embodiment, the protease is expressed in a tumor tissue sample, in particular a biopsy from a patient. In one embodiment, the expression of the reporter gene is indicative for protease expression in the tumor sample.

According to the methods as described herein, antibodies comprising a masking moiety connected to the second antigen binding moiety through a protease-cleavable linker are used to detect protease expression in tumor samples. In one embodiment, the target antigen of the protease-activatable bispecific antibody is a cell surface receptor. In one embodiment, the target antigen is selected from the group consisting of CEA, Her2, TYRP, EGFR, MCSP, STEAP1, WT1 and FolR1. In one embodiment, the target antigen is FolR1.

In one embodiments the protease-activatable bispecific antibody used according to the invention comprises at least one antigen binding moiety that is specific for FolR1 further comprises an anti-idiotypic CD3 scFv comprising at least one of the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25. In one embodiment, the anti-idiotypic scFv comprises the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25.

In one embodiments the protease-activatable bispecific antibody used according to the invention comprises at least one antigen binding moiety that is specific for FolR1 further comprises an anti-idiotypic CD3 scFv comprising a polypeptide sequence that is at least about 95%, 96%, 97%, 98%, 99% or 100% identical to SEQ ID NO: 29. In one embodiment, the anti-idiotypic scFv comprises the polypeptide sequence of SEQ ID NO: 29.

Accordingly, the assay of the present invention is able to assess both binding to a target antigen as described herein and expression of a protease as described herein. In one embodiment, the binding to the target antigen and the expression of the protease are determined in the same vial. In one embodiment, the assay of the present invention is used for selection of protease-cleavable linkers suitable for the treatment of a tumor.

In one embodiment the protease-activatable bispecific antibody used according to the invention comprises a polypeptide sequence that is at least about 95%, 96%, 97%, 98%, 99% or 100% identical to SEQ ID NO: 5, a polypeptide sequence that is at least about 95%, 96%, 97%, 98%, 99% or 100% identical to SEQ ID NO: 6 and a polypeptide sequence that is at least about 95%, 96%, 97%, 98%, 99% or 100% identical to SEQ ID NO: 7.

In one embodiment the protease-activatable bispecific antibody used according to the invention comprises the polypeptide sequence of SEQ ID NO: 5, the polypeptide sequence of SEQ ID NO: 6 and the polypeptide sequence of SEQ ID NO: 7.

In one embodiment the protease-activatable bispecific antibody used according to the invention comprises a polypeptide sequence that is at least about 95%, 96%, 97%, 98%, 99% or 100% identical to SEQ ID NO: 5, a polypeptide sequence that is at least about 95%, 96%, 97%, 98%, 99% or 100% identical to SEQ ID NO: 7 and a polypeptide sequence that is at least about 95%, 96%, 97%, 98%, 99% or 100% identical to SEQ ID NO: 10.

In one embodiment the protease-activatable bispecific antibody used according to the invention comprises the polypeptide sequence of SEQ ID NO: 5, the polypeptide sequence of SEQ ID NO: 7 and the polypeptide sequence of SEQ ID NO: 10. (8363)

In one embodiment the protease-activatable bispecific antibody used according to the invention comprises a polypeptide sequence that is at least about 95%, 96%, 97%, 98%, 99% or 100% identical to SEQ ID NO: 5, a polypeptide sequence that is at least about 95%, 96%, 97%, 98%, 99% or 100% identical to SEQ ID NO: 7 and a polypeptide sequence that is at least about 95%, 96%, 97%, 98%, 99% or 100% identical to SEQ ID NO: 8.

In one embodiment the protease-activatable bispecific antibody used according to the invention comprises the polypeptide sequence of SEQ ID NO: 5, the polypeptide sequence of SEQ ID NO: 7 and the polypeptide sequence of SEQ ID NO: 8.

In one embodiment the protease-activatable bispecific antibody used according to the invention comprises a polypeptide sequence that is at least about 95%, 96%, 97%, 98%, 99% or 100% identical to SEQ ID NO: 3, a polypeptide sequence that is at least about 95%, 96%, 97%, 98%, 99% or 100% identical to SEQ ID NO: 4 and a polypeptide sequence that is at least about 95%, 96%, 97%, 98%, 99% or 100% identical to SEQ ID NO: 5.

In one embodiment the protease-activatable bispecific antibody used according to the invention comprises the polypeptide sequence of SEQ ID NO: 3, the polypeptide sequence of SEQ ID NO: 4 and the polypeptide sequence of SEQ ID NO: 5.

In further embodiments, provided is a method for selecting a bispecific antibody for the treatment of a tumor, wherein the bispecific antibody comprises:
  a. a first antigen binding moiety capable of specific binding to a target antigen; and
  b. a second antigen binding moiety capable of specific binding to a signal transducing cell surface receptor;
wherein the method comprises determining the presence of a target antigen in a tumor sample according to the method as described herein and wherein the bispecific antibody is selected for treatment of the tumor if expression of the reporter gene is detected.

In one embodiment, the bispecific antibody additionally comprises c) a masking moiety covalently attached to the second antigen binding moiety through a protease-cleavable linker, wherein the masking moiety is capable of specific binding to the idiotype of the second antigen binding moiety thereby reversibly concealing the second antigen binding moiety as described herein. Such constructs are described herein to as being protease-activatable.

Bispecific antibodies targeting different antigens on the same or even different cells are considered to overcome some of the current challenges in cancer therapy. Some of these construct bind to antigens on different cells, e.g., to a target antigen on a cancer cell and an immunostimulatory antigen on an effector cell, in particular on T cells. The target antigen is supposed to direct the bispecific antibody to the tumor tissue whereas the immunostimulatory antigen activates the effector cells which leads to efficient destruction of the tumor cells by the effector cells, e.g., T cells. In addition, it might be necessary to conceal the immunostimulatory antigen until the antibody reaches its tumor target to avoid adverse effects due to the systemic application of the antibody. Some constructs comprise activatable immunomodulatory moieties which are unconcealed upon binding to the tumor. This can be done as described herein by concealing the immunomodulatory moiety with a masking moiety attached to the immunomodulatory moiety through a protease-cleavable linker. These constructs are described herein to as being protease-activatable.

For efficient lysis of a tumor, the tumor cells must express the target antigen in suitable amount for the antibody to bind efficiently to the tumor cells. Additionally, for protease-activatable constructs with concealed moieties, the tumor cells must also express a tumor tissue specific protease in suitable amounts to efficiently cleave the protease-cleavable linker between the masking moiety and the masked moiety. The method according to the present invention provides an assay to assess if a bispecific antibody is suitable for the treatment of a tumor by assessing a tumor sample, e.g., a tumor biopsy for target antigen binding and/or protease expression. Accordingly, the expression of the reporter gene measured in a method according to the invention is indicative for a suitable bispecific antibody for the treatment of a tumor, wherein the tumor sample is a tumor biopsy from a patient and wherein the bispecific antibody is a candidate antibody for treatment of the tumor. In one embodiment, the assay of the present invention is used for selection of protease-cleavable linkers suitable for the treatment of a tumor. The assessment can be done in high-throughput format as described herein, i.e. a multitude of candidate antibodies for treatment of a tumor can be assessed in parallel. The assay is robust and tolerates the presence of dead cells in the tumor sample. Bispecific antibodies selected for the treatment of a tumor can be used in therapeutic methods as described herein. Protease-cleavable linkers suitable for the treatment of a tumor as selected using the assay of the invention can be included in novel or known bispecific antibodies for the treatment of cancer.

Any of bispecific antibodies selected for the treatment of a tumor as described herein, may be used in therapeutic methods. Bispecific antibodies selected for the treatment of a tumor as described herein can be used as immunotherapeutic agents, for example in the treatment of cancers. For use in therapeutic methods, bispecific antibodies selected according to the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect bispecific antibodies selected for the treatment of a tumor according to the method of the invention are provided. In one aspect, provided are the selected bispecific antibodies for use as a medicament. In further aspects, selected bispecific antibodies of the invention for use in treating a disease are provided. In certain embodiments, selected bispecific antibodies of the invention for use in a method of treatment are provided. In one embodiment, the invention provides a bispecific antibody selected as described herein for use in the treatment of a disease in an individual in need thereof. In certain embodiments, the invention provides a bispecific antibody for use in a method of treating an individual having a disease comprising administering to the individual a therapeutically effective amount of the selected bispecific antibody. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a bispecific antibody selected as described herein for use in inducing lysis of a target cell, particularly a tumor cell. In certain embodiments, the invention provides a bispecific antibody for use in a method of inducing lysis of a target cell, particularly a tumor cell, in an individual comprising administering to the individual an effective amount of the selected bispecific antibody to induce lysis of a target cell. An "individual" according to any of the above embodiments is a mammal, preferably a human.

In a further aspect, the invention provides for the use of a bispecific antibody selected for the treatment of a tumor as described herein in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human. In a particular embodiment, a tumor sample, e.g., a tumor biopsy, of the individual is assessed using the methods according to the invention to find a suitable bispecific antibody for the treatment of the tumor.

In a further aspect, the invention provides a method for treating a disease. In one embodiment, the method comprises selecting a bispecific antibody for the treatment of the disease according to the methods as described herein and administering to an individual having such disease a therapeutically effective amount of the selected bispecific antibody. In one embodiment a composition is administered to said individual, comprising the selected bispecific antibody in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent. e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with a bispecific antibody selected according to the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of a bispecific antibody to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a bispecific antibody include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the bispecific antibody may not provide a cure but may only provide partial benefit. In some embodiments, a physiological change having some benefit is also considered therapeutically beneficial. Thus, in some embodiments, an amount of bispecific antibody that provides a physiological change is considered an "effective amount" or a "therapeutically effective amount". The subject, patient, or individual in need of treatment is typically a mammal, more specifically a human.

In some embodiments, an effective amount of a selected bispecific antibody according to the invention is administered to a cell. In other embodiments, a therapeutically effective amount of a bispecific antibody is administered to an individual for the treatment of disease. For the prevention or treatment of disease, the appropriate dosage of a bispecific antibody (when used alone or in combination with one or more other additional therapeutic agents) will depend on the type of disease to be treated, the route of administration, the body weight of the patient, the type of T cell activating bispecific antibody, the severity and course of the disease, whether the T cell activating bispecific antibody is administered for preventive or therapeutic purposes, previous or concurrent therapeutic interventions, the patient's clinical history and response to the bispecific antibody, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The selected bispecific antibody is suitably administered to the patient at one time or over a series of treatments. Depending on the type and severity of the disease, about 1 μg/kg to 15 mg kg (e.g., 0.1 mg/kg-10 mg/kg) of bispecific antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the T cell activating bispecific antibody would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/g body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the bispecific antibody). An initial higher loading dose, followed by one or more lower doses may be administered. However, other dosage regimens may be useful. The progress of this therapy is easily monitored by conventional techniques and assays.

The selected bispecific antibody according to the invention will generally be used in an amount effective to achieve the intended purpose. For use to treat or prevent a disease condition, the selected bispecific antibodys, or pharmaceutical compositions thereof, are administered or applied in a therapeutically effective amount. Determination of a therapeutically effective amount is well within the capabilities of those skilled in the art, especially in light of the detailed disclosure provided herein. For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data. Dosage amount and interval may be adjusted individually to provide plasma levels of the bispecific antibodys which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

A therapeutically effective dose of the selected bispecific antibodys described herein will generally provide therapeutic benefit without causing substantial toxicity. Toxicity and therapeutic efficacy of a bispecific antibody can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antibodies that exhibit large therapeutic indices are preferred. In one embodiment, the selected bispecific antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with selected bispecific antibodys according to the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Exemplary Embodiments

1. An in vitro method for determining the presence of a target antigen in a tumor sample comprising the steps of:
   i) providing a tumor sample;
   ii) providing reporter cells comprising a reporter gene under the control of a signal transducing cell surface receptor;
   iii) adding to the tumor sample a bispecific antibody comprising:
      a) a first antigen binding moiety capable of specific binding to a target antigen; and
      b) a second antigen binding moiety capable of specific binding to the signal transducing cell surface receptor;
   iv) adding the reporter cells to the tumor sample; and
   v) determining the presence of the target antigen by determining the expression of the reporter gene.
2. The method according to embodiment 1, wherein the target antigen is expressed by the tumor cells.
3. The method according to any one of embodiments 1 or 2, wherein the expression of the reporter gene is indicative for binding of the first antigen binding moiety to the target antigen.
4. The method according to any one of embodiments 1 to 3, wherein the bispecific antibody additionally comprises:
   c) a masking moiety covalently attached to the second antigen binding moiety through a protease-cleavable linker, wherein the masking moiety is capable of specific binding to the idiotype of the second antigen binding moiety thereby reversibly concealing the second antigen binding moiety;
5. The method according to any one of embodiments 1 to 4, wherein a protease cleaves the protease-cleavable linker, wherein the second antigen binding moiety is unconcealed.
6. The method according to any one of embodiments 1 to 5, wherein the protease is expressed by the tumor cells.
7. The method according to any one of embodiments 4 to 6 wherein the expression of the reporter gene is indicative for protease expression in the tumor sample.
8. The method according to any one of embodiments 1 to 7, wherein the tumor sample is a tumor tissue sample, in particular a biopsy from a patient.
9. The method according to any one of embodiments 1 to 8, wherein the tumor sample is not digested.
10. The method according to any one of embodiments 1 to 9, wherein the tumor sample is digested, in particular by in particular by collagenase or hyaluronidase.
11. The method according to any one of embodiments 1 to 10, wherein the tumor sample contains dead cells, in particular more than 10% of dead cells.
12. The method according to any one of embodiments 6 to 11, wherein protease expression is indicative for a malignant tumor.
13. The method according to any one of embodiments 1 to 12, wherein the signal transducing cell surface receptor is functionally linked to a response element.
14. The method according to any one of embodiments 1 to 13, wherein the response element controls the expression of the reporter gene.
15. The method according to any one of embodiments 1 to 14, wherein the response element is part of the NF-κB pathway.

16. The method according to embodiment 15, wherein the response element comprises at least one DNA repeat with a DNA sequence of SEQ ID NO: 68, 69, 70, 71 or 72.
17. The method according to any one of embodiments 15 or 16, wherein the response element comprises a DNA sequence of SEQ ID NO 73, 74, 75 or 76.
18. The method according to any one of embodiments 1 to 17, wherein the reporter gene is coding for a fluorescent or a luminescent protein.
19. The method according to any one of embodiments 1 to 18, wherein the reporter gene is coding for green fluorescent protein (GFP) or luciferase.
20. The method according to any one of embodiments 1 to 19, wherein the reporter cells comprise the DNA sequence coding for the reporter gene under the control of the response element, and the DNA sequence coding for the signal transducing cell surface receptor.
21. The method according to any one of embodiments 1 to 20, wherein the reporter cells comprise at least one DNA repeat with a DNA sequence of SEQ ID NO: 68, 69, 70, 71 or 72, wherein the DNA repeat is operatively linked to the reporter gene and wherein the reporter gene is expressed upon binding of the second antigen binding moiety to the signal transducing cell surface receptor.
22. The method according to any one of embodiments 1 to 21, wherein the second antigen binding moiety is capable of specific binding to CD3ε.
23. The method according to any one of embodiment 4 to 22, wherein the protease-cleavable linker comprises a protease recognition sequence.
24. The method according to embodiment 23, wherein the protease recognition sequence is selected from the group consisting of:

a)
            (SEQ ID NO: 45)
RQARVVNG;

b)
            (SEQ ID NO: 46)
VHMPLGFLGPGRSRGSFP;

c)
            (SEQ ID NO: 47)
RQARVVNGXXXXXVPLSLYSG;

d)
            (SEQ ID NO: 48)
RQARVVNGVPLSLYSG;

e)
            (SEQ ID NO: 49)
PLGLWSQ;

f)
            (SEQ ID NO: 50)
VHMPLGFLGPRQARVVNG;

g)
            (SEQ ID NO: 51)
FVGGTG;

h)
            (SEQ ID NO: 52)
KKAAPVNG;

i)
            (SEQ ID NO: 53)
PMAKKVNG;

j)
            (SEQ ID NO: 54)
QARAKVNG;

k)
            (SEQ ID NO: 55)
VHMPLGFLGP;

l)
            (SEQ ID NO: 56)
QARAK;

m)
            (SEQ ID NO: 57)
VHMPLGFLGPPMAKK;

n)
            (SEQ ID NO: 58)
KKAAP;
and o)
            (SEQ ID NO: 59)
PMAKK, wherein X is any amino acid.
25. The method according to any one of embodiments 4 to 24, wherein the protease is selected from the group consisting of metalloproteinase, serine protease, cysteine protease, aspartic proteases, and cathepsin protease.
26. The method according to embodiment 25, wherein the metalloproteinase is a matrix metalloproteinase (MMP), particularly MMP9 or MMP2.
27. The method according to embodiment 26, wherein the serine protease is Matriptase.
28. The method according to any one of embodiments 4 to 27, wherein the masking moiety is covalently attached to the heavy chain variable region of the second antigen binding moiety.
29. The method according to any one of embodiments 4 to 28, wherein the masking moiety is covalently attached to the light chain variable region of the second antigen binding moiety.
30. The method according to any one of embodiments 4 to 29, wherein the masking moiety is an anti-idiotypic scFv.
31. The method according to any one of embodiments 1 to 30, wherein the first and the second antigen binding moiety are fused to each other, optionally via a peptide linker.
32. The method according to any one of embodiments 1 to 31, wherein the first and the second antigen binding moieties are conventional Fab molecules comprising a common light chain.
33. The method according to embodiment 32, wherein the second antigen binding moiety is fused at the C-terminus of the Fab heavy chain to the N-terminus of the Fab heavy chain of the first antigen binding moiety, optionally via a peptide linker.
34. The method according to any one of embodiments 32 or 33, wherein the Fab light chain of the first antigen binding moiety and the Fab light chain of the second antigen binding moiety are fused to each other, optionally via a peptide linker.
35. The method according to any one of embodiments 1 to 34, wherein the bispecific antibody comprises a third antigen binding moiety capable of specific binding a tumor antigen.
36. The method according to embodiment 35, wherein the third antigen binding moiety is a conventional Fab molecule, or a crossover Fab molecule wherein either the variable or the constant regions of the Fab light chain and the Fab heavy chain are exchanged.
37. The method according to any one of embodiments 36, wherein the third antigen binding moiety is identical to the first antigen binding moiety.
38. The method according to any one of embodiments 1 to 37, wherein the bispecific antibody additionally comprises an Fc domain composed of a first and a second subunit capable of stable association.
39. The method according to embodiment 38, wherein the Fc domain is an IgG, specifically an IgG1 or IgG4, Fc domain.
40. The method according to any one of embodiments 38 or 39, wherein the Fc domain is a human Fc domain.
41. The method according to any one of embodiments 1 to 40, wherein the target antigen is a cell surface receptor.
42. The method according to any one of embodiments 1 to 41, wherein the target antigen is FolR1.
43. The method according to any one of embodiments 1 to 42, wherein the target antigen is a peptide bound to a molecule of the human major histocompatibility complex (MHC).
44. The peptide according to embodiments 43, wherein the peptide has an overall length of between 8 and 100, preferably between 8 and 30, and more preferred between 8 and 16 amino acids.
45. The method according to any one of embodiments 4 to 44, wherein the binding to the target antigen and the expression of the protease are determined in the same vial.
46. An in vitro method for selecting a bispecific antibody for the treatment of a tumor, wherein the bispecific antibody comprises:
    a. a first antigen binding moiety capable of specific binding to a target antigen; and
    b. a second antigen binding moiety capable of specific binding to a signal transducing cell surface receptor;
    wherein the method comprises determining the presence of a target antigen in a tumor sample according to the method of any one of embodiments 1 to 45 and wherein the bispecific antibody is selected for treatment of the tumor if expression of the reporter gene is detected.
47. The method essentially as hereinbefore described.

The following are examples of methods and compositions of the invention. It is understood that various other embodiments may be practiced, given the general description provided above. Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

III. Examples

Example 1

Figure 2F:
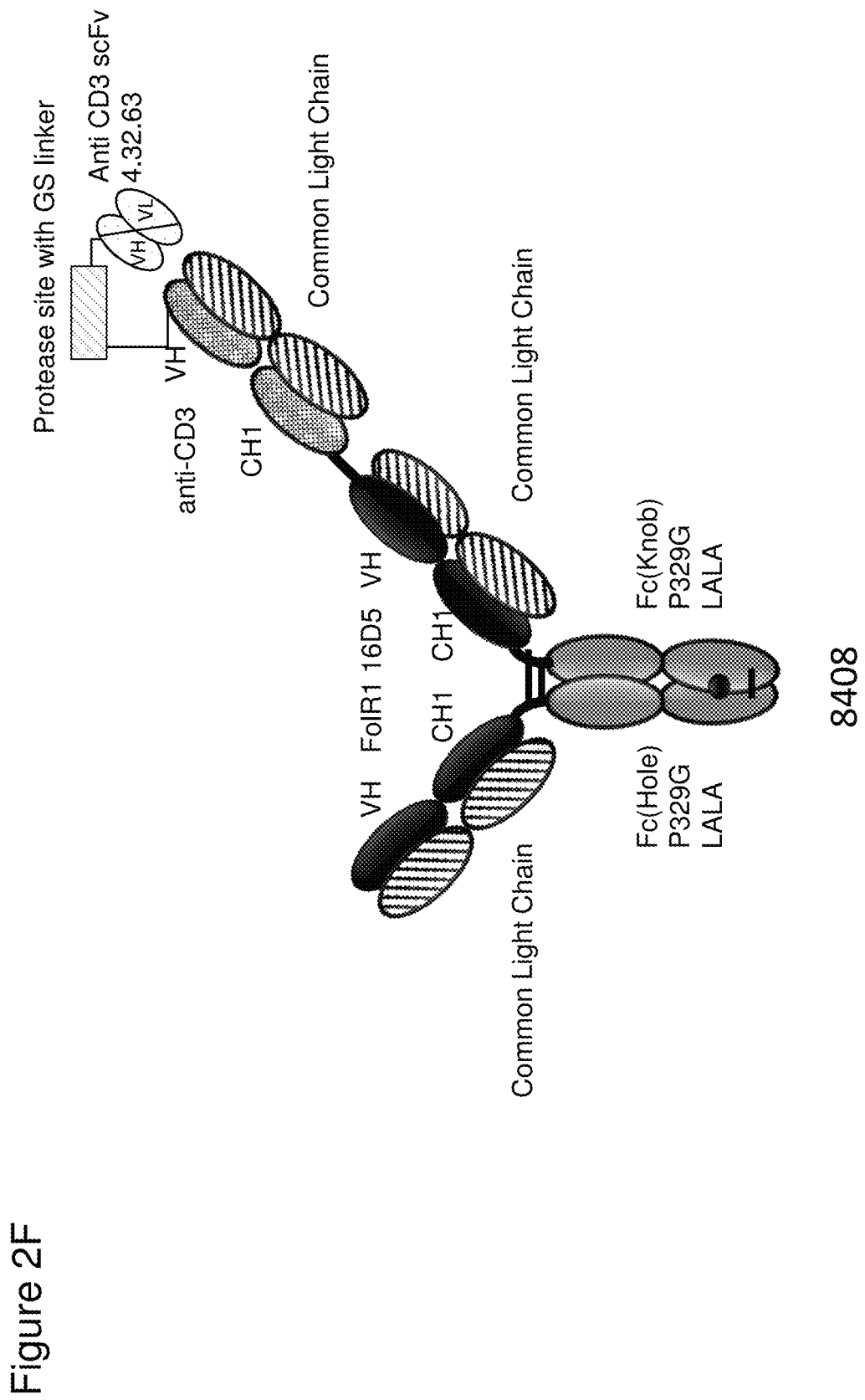
FIG. 2F: ID 8408, anti ID CH2527 scFv 4.15.64 MK062 Matriptase site CD3 16D5 Fc.

Preparation of Anti FolR1/Anti-CD3 T Cell Bispecific (TCB) Molecules with Anti CD3 scFv The following molecules were prepared in this example; schematic illustrations thereof are shown in FIGS. 2A-F:
ID 8364: "FolR1 2+1 IgG, classic format (anti idiotypic scFv 4.32.63—MMP9-MK062 Matriptase site—CD3—N-terminal fused to FolR1 VH—inert Fc) with N-terminal fused anti CD3 scFv 4.32.63 and MMP9—MK062 protease linker" (FIG. 2A, SEQ ID NOs 5, 6, 7)
ID 8363: "FolR1 2+1 IgG, classic format (anti idiotypic scFv 4.32.63—Cathepsin S/B site—CD3—N-terminal fused to FolR1 VH—inert Fc) with N-terminal fused anti CD3 scFv 4.32.63 and Cathepsin S/B protease linker" (FIG. 2B, SEQ ID NOs 5, 7, 10)
ID 8409: "FolR1 2+1 IgG, classic format (anti idiotypic scFv 4.32.63—non cleavable linker—CD3—N-terminal fused to FolR1 VH—inert Fc) with N-terminal fused anti CD3 scFv 4.32.63 and non cleavable GS linker." (FIG. 2C)
ID 6298: "FolR1 2+1 IgG, classic format." (FIG. 2D, SEQ ID Nos 3, 4, 5)
ID 7235/6182: "DP47GS 2+1 IgG, inverted format." (FIG. 2E)
ID 8408: "FolR1 2+1 IgG, classic format (anti idiotypic scFv 4.32.63—Matriptase site—CD3—N-terminal fused to FolR1 VH—inert Fc) with N-terminal fused anti CD3 scFv 4.32.63 and Matriptase protease linker" (FIG. 2F, SEQ ID NOs 5, 7, 8)

The variable domains were subcloned in frame with the pre-inserted domains into the respective recipient mammalian expression vector. Protein expression is driven by an MPSV promoter and a synthetic polyA signal sequence is present at the 3' end of the CDS. In addition each vector contains an EBV OriP sequence.

The molecules were produced by co-transfecting HEK293-EBNA cells growing in suspension with the mammalian expression vectors using polyethylenimine (PEI). For transfection HEK293 EBNA cells were cultivated in serum free ExCell culture medium containing 6 mM L-glutamine and 250 mg/l G418. For the production in 600 ml tubespin flasks (max, working volume 400 ml) 800 million HEK293 EBNA cells were seeded 24 hours before transfection without G418. For transfection 800 mio cells were centrifuged for 5 min at 210×g and supernatant was replaced by 40 ml pre-warmed CD CHO medium containing 6 mM L-Glutamine. Expression vectors were mixed with 40 ml CD CHO medium containing 6 mM L-Glutamine to a total amount of 400 µg DNA. After addition of 1080 µl PEI solution (2.7 µg/ml) the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a 5% $CO_2$ atmosphere. After incubation, 320 ml ExCell+6 mM L-glutamine+5 g/L Pepsoy+1.0 mM VPA+3 µl glucose medium was added and cells were cultivated for 24 hours prior to feeding with 7% Feed 7. After 6-7 days the cultivation supernatant was collected for purification by centrifugation for 20-30 min at 210×g (Sigma 8K centrifuge). The solution was sterile filtered (0.22 µm filter) and sodium azide in a final concentration of 0.01% w/v was added. The solution was kept at 4° C. until purification.

The secreted protein was purified from cell culture supernatants by affinity chromatography using ProteinA affinity chromatography, followed by one to two size exclusion chromatographic steps.

For affinity chromatography supernatant was loaded on a Protein A MabSelectSure (CV=5 mL, GE Healthcare) equilibrated with 20 mM Sodium Citrate, 20 mM Sodium Phosphate, pH 7.5. Unbound protein was removed by washing with at least 10 column volumes 20 mM Sodium Citrate, 20 mM Sodium Phosphate, pH 7.5 and target protein was eluted in 20 column volumes (gradient from 0%-100%) 20 mM Sodium Citrate, 100 mM Sodium Chloride, 100 mM Glycine, pH 3.0. Protein solution was neutralized by adding 1/10 of 0.5 M Na2HPO4 pH 8.0. Target protein was concentrated with Amicon®Ultra-15 Ultracel 30K (Merck Millipore Ltd.) to a volume of 4 ml maximum prior loading on a HiLoad Superdex 200 column (GE Healthcare) equilibrated with 20 mM Histidine, 140 mM NaCl, 0.01% Tween pH 6.0.

The protein concentration of purified protein samples was determined by measuring the optical density (OD) at 280 nm divided by the molar extinction coefficient calculated on the basis of the amino acid sequence.

Purity and molecular weight of the molecules after the final purification step were analyzed by CE-SDS analyses in the presence and absence of a reducing agent. The Caliper LabChip GXII system (Caliper Lifescience) was used according to the manufacturer's instruction.

The aggregate content of the molecules was analyzed using a TSKgel G3000 SW XL analytical size-exclusion column (Tosoh) in 25 mM K2HPO4, 125 mM NaCl, 200 mM L-arginine monohydrochloride, 0.02% (w/v) NaN3, pH 6.7 running buffer at 25° C. The final quality of all molecules was good, with ≥95% monomer content.

TABLE 1

Summary of production and purification of protease-activated TCB molecules.

| Molecule | Titer [mg/l] | Yield [mg/l] | Analytical SEC (HMW/Monomer/LMW) [%] |
|---|---|---|---|
| 1 (8364) | 34.55 | 1.72 | 0.68/99.32/0 |
| 2 (8363) | 33.75 | 1.59 | 4.02/95.98/0 |

Example 2

Quality Control and Stability

Capillary Electrophoresis SDS analysis of different TCB molecules. Purity and molecular weight of the molecules after the final purification step were analyzed by CE-SDS analyses in the presence and absence of a reducing agent. The Caliper LabChip GXII system (Caliper Lifescience) was used according to the manufacturer's instruction. Comparison of untreated molecules (stored at 4° C.), treated molecules (treated with appropriate recombinant protease (R&D Systems) for 24 h at 37° C. and molecule incubated for 72 h at 37° C.

Figure 3A:
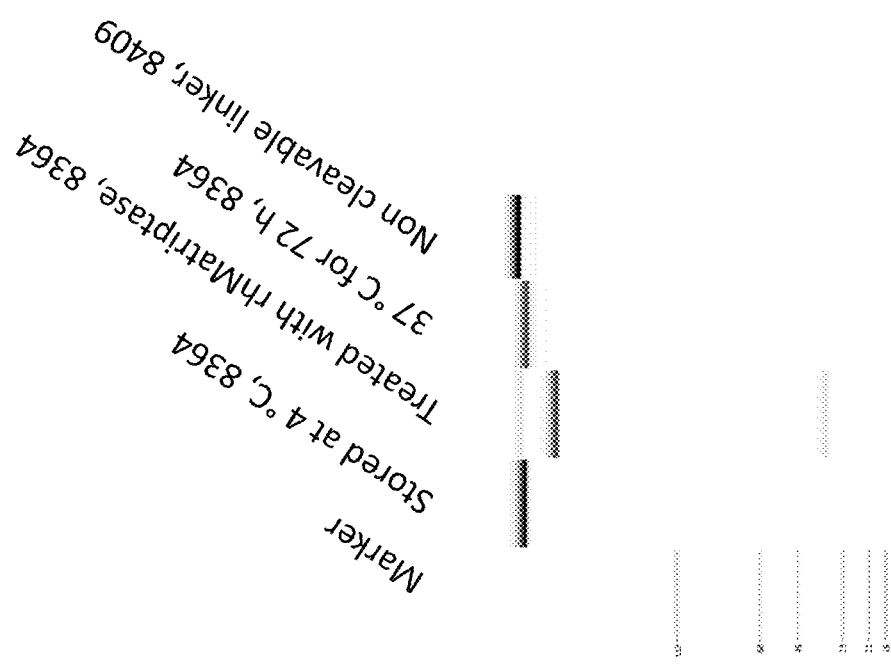
FIG. 3A: CE-SDS analysis of the TCB 8364 depicted in FIG. 2A (final purified preparation): Lane A=Protein standard, lane B=protein stored at 4° C. lane C=protein pretreated with rhMatriptase/ST14 (R&D Systems), lane D=protein incubated for 72 h at 37° C. and lane E=non cleavable linker construct.
Figure 3B:
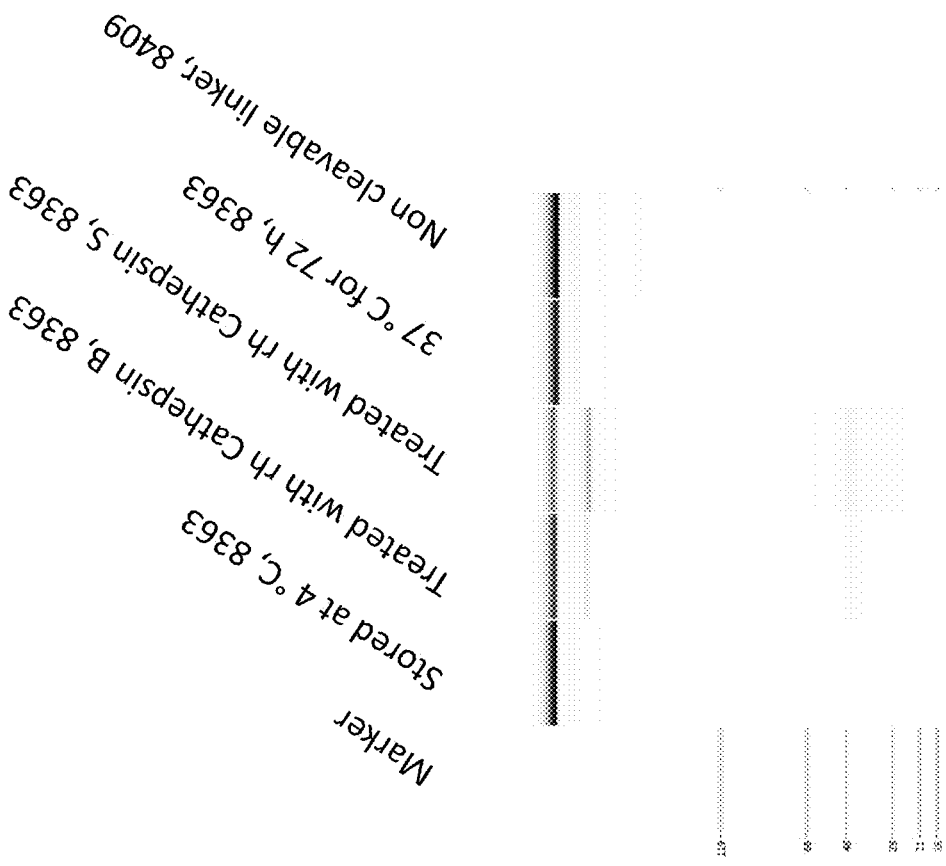
FIG. 3B: CE-SDS analysis of the TCB 8363 depicted in FIG. 2B (final purified preparation): Lane A=Protein standard, lane B=protein stored at 4° C., lane C=protein pretreated with rhCathepsin B (R&D Systems), lane D=protein pretreated with rhCathepsin S (R&D Systems), lane E=protein incubated for 72 h at 37° C. and lane F=non cleavable linker construct.

Comparison of the untreated and treated molecule shows cleavage of the anti ID scFv after rhMatriptase/ST14 treatment for the molecule containing the MMP9-MK062 Matriptase linker (FIG. 3A). Cleavage with rhCathepsin B and rhCathepsin S treatment is incomplete. The conditions for the purified enzymes have not been optimal (FIG. 3B).

Molecules incubated at 37° C. for 72 h are running on the same height than pure molecules suggesting that the molecules are stable at 37° C. for the time of in vitro assay duration. Pre-stained protein Marker Mark 12 (Invitrogen) was used for estimation of correct molecule weight.

Example 3

Comparison of Different Linkers and Formats of Protease-Activated FolR1 TCBs

Figure 4A:
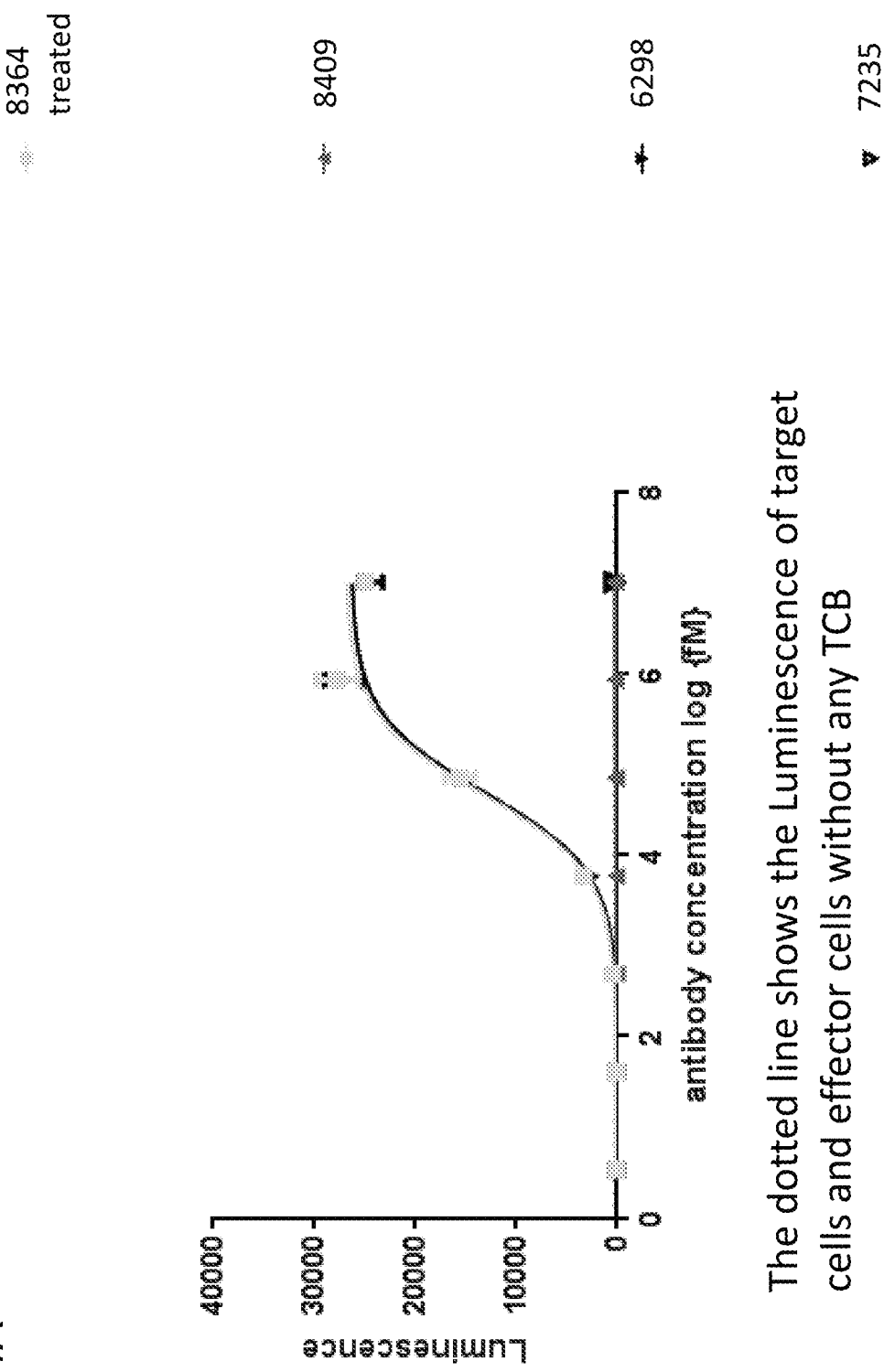
FIG. 4 depicts the Jurkat NFAT activation assay according to FIG. 1 using HeLa (4A) and Skov-3 (4B) cells as target cells. Each point represents the mean value of triplicates. Standard deviation is indicated by error bars. The FolR1 TCB (black triangles pointing down) and rhMatriptase/ST14 pretreated protease-activated TCB (8364, grey filled squares) with N-terminally fused anti ID CD3 4.32.63 scFv and MMP9-Matriptase MK062 site were compared. The masked TCB (containing a GS non cleavable linker, grey triangles pointing up) and the non-targeted TCB control (empty triangle pointing down) are included as negative controls. The dotted line shows the Luminescence of target cells and effector cells without any TCB.
Figure 4B:
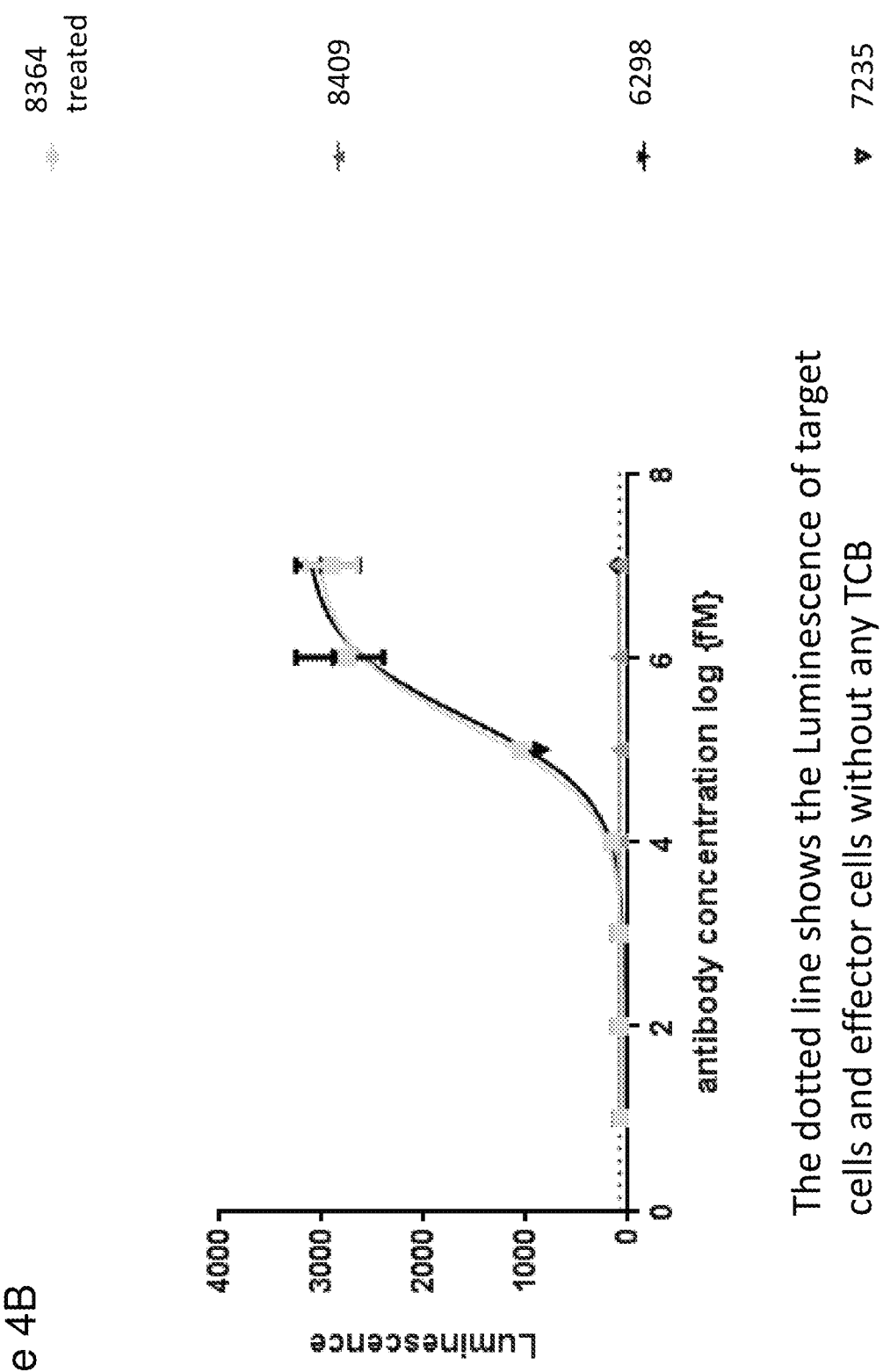

Jurkat NFAT activation assay. Jurkat NFAT activation assay for comparison of different formats and linkers of protease-activated TCB. Jurkat-NFAT reporter cell line (Promega) is a human acute lymphatic leukemia reporter cell line with a NFAT promoter, expressing human CD3ε. If the TCB binds the tumor target and the CD3 binder (crosslinkage) binds the CD3ε Luciferase expression can be measured in Luminescence after addition of One-Glo substrate (Promega), 20.000 target cells were seeded in 96-well white walled clear bottom plate (Greiner BioOne) in 50 ul/well Jurkat medium (RPMI1640, 2 g/l Glucose, 2 g/l NaHCO3, 10% FCS, 25 mM HEPES, 2 mM L-Glutamin, 1×NEAA, 1×Sodium-pyruvate) without Hygromycine. Plates were incubated for about 20 hours at 37° C. Jurkat-NFAT reporter cells were harvested and viability was assessed using ViCell. Cells were resuspended in Jurkat medium without Hygromycine and 50 µl per well (50.000 cells/well) were added. The E:T ratio was 2.5:1 (based on cell number seeded). Antibodies were diluted in Jurkat medium without Hygromycine and 50 ul/well were added. Cells were incubated at 37° C. for 6 h in a humidified incubator before they were taken out of the incubator for about 10 min to adapt to room temperature prior to Luminescence read out. 50 µl/well of ONE-Glo solution were added to wells and incubated for 10 min at room temperature in the dark. Luminescence was detected using WALLAC Victor3 ELISA reader (PerkinElmer2030), 1 sec/well as detection time. As a positive control (pretreated) the protease-activated TCBs were treated with rhMatriptase/ST14 (R&D Systems) for about 20 h at 37° C. Comparison of the pretreated protease-activated TCB (8364, grey filled squares) and FolR1 TCB (black triangles pointing down) showed that potency after cleavage is recovered completely. No Luminescence was detectable for cells incubated with the masked TCB (containing a GS non cleavable linker, grey triangles pointing up) and the non-targeted TCB control (empty triangle pointing down) for both cell lines in this concentration range. The dotted line shows the Luminescence of target cells and effector cells without any TCB (FIGS. 4A-B).

Example 4

Jurkat-NFAT Reporter Assay to Monitor Target Expression (FOLR1 TCB) and Protease Activity (Protease-Activated FOLR1 TCB) in Primary Tumor Samples The intention of this assay was to show tumor target antigen (FolR1) expression and activity of tumor specific proteases like MMP9, Matriptase or Cathepsin in human tumor samples.

Jurkat-NFAT reporter cell line (Promega) is a human acute lymphatic leukemia reporter cell line with a NFAT promoter, expressing human CD3ε. Luciferase expression can be measured, if the T cell bispecific molecule binds the tumor target and the CD3ε (crosslinkage). Luminescence is measured after addition of One-Glo substrate (Promega). Primary tumor samples were received from Indivumed GmbH, Germany. Samples were shipped over night in transport medium. About 24 h after surgery the sample was cut in small pieces.

First Method (FIG. 5):

24-well plate was prepared by inserting one Millicell Cell Culture Insert, 12 mm, hydrophilic PTFE, 0.4 µm (PICM01250, MerckMillipore) in each well. Antibodies were diluted in Jurkat medium without Hygromycine but with 1.5× penicillin/streptomycine solution. 400 ul were added inside the well and 600 ul were added outside the filter. Two to three pieces of human tumor were added to each well and incubated for 48 hours at 37° C., 5% CO2.

Jurkat-NFAT reporter cells were harvested and viability was assessed using ViCell. Cells were centrifuged at 350×g, 7 min before they were resuspended in Jurkat medium without Hygromycine and 500 µl per well (500.000) cells/well) were added. Plate was incubated for 5 h at 37° C. in a humidified incubator before it was taken out for Luminescence read out. 500 µl of ONE-Glo solution was added to each well and incubated for 10 min at room temperature in the dark. Luminescence was detected using WALLAC Victor3 ELISA reader (PerkinElmer2030), 1 sec/well as detection time.

Second Method (FIG. 6):

96-well white walled, flat (clear) bottom plate was prepared by adding 18 ul cold Matrigel (Matrigel (734-1101, Corning/VWR). Plate was incubated for 2 min at 37° C. before tumor pieces were added (triplicates). 33 ul of cold Matrigel were added per well and plate was incubated again for 2 min at 37° C. 50 ul of antibody dilution (in Jurkat medium without Hygromycine but containing 2× Penicillin/Streptomycine) was added per well and plate was incubated for about 48 hours at 37° C., 5% CO2.

Jurkat-NFAT reporter cells were harvested and viability was assessed using ViCell. Cells were centrifuged at 350×g, 7 min before they were resuspended in Jurkat medium without Hygromycine and 50 µl per well (50.000 cells/well) were added. Plate was incubated for 5 h at 37° C. in a humidified incubator before it was taken out for Luminescence read out. 80 ul of each well were transferred into a white walled 96-well plate. 27 µl/well of ONE-Glo solution were added to each well and incubated for 10 min at room temperature in the dark. Luminescence was detected using WALLAC Victor3 ELISA reader (PerkinElmer2030), 1 sec/well as detection time.

Figure 5:
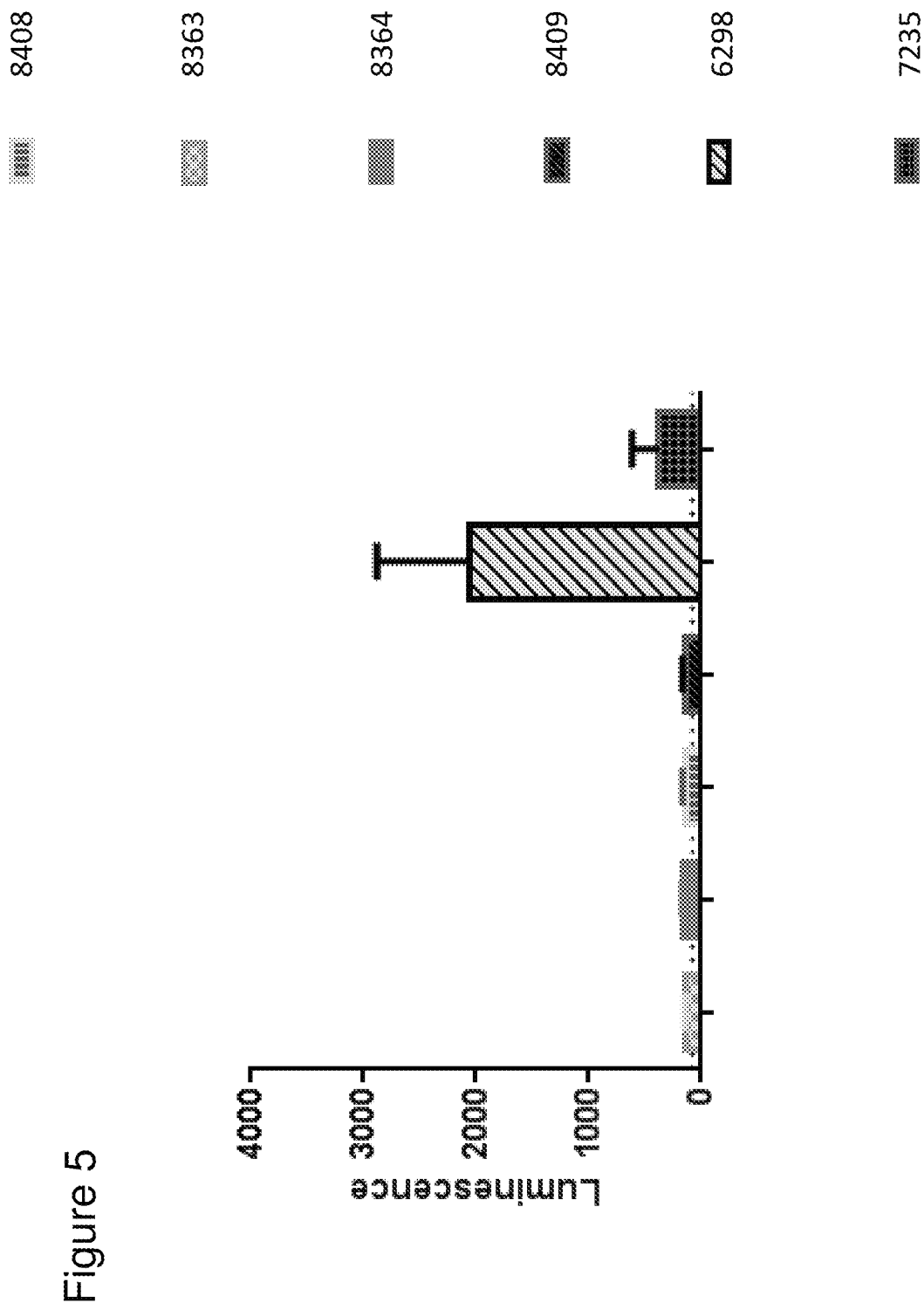
FIG. 5 depicts the Jurkat-NFAT activation assay with benign primary tumor sample and FolR1 TCBs. Jurkat NFAT reporter cells are activated after co-incubation with FolR1 TCB (6298) in 24 well plate with cell culture inserts. Protease-activated FolR1 TCBs (8363, 8364, 8408) and control TCBs (8409, 7235) do not induce Luciferase expression. The dotted line indicates the baseline Luminescence for Jurkat NFAT cells co-incubated with tumor.
Figure 6:
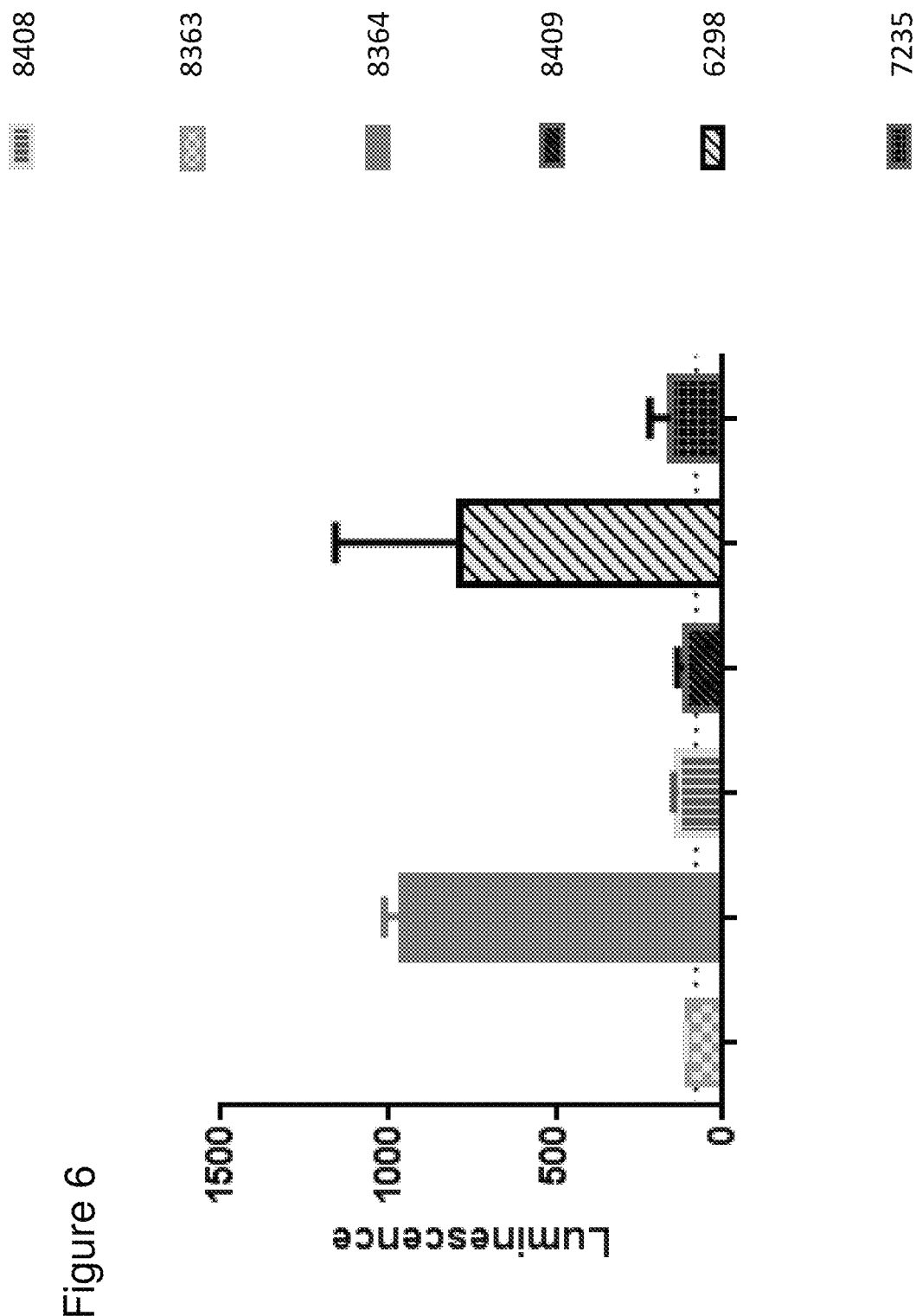
FIG. 6 depicts the Jurkat-NFAT activation assay with malignant primary tumor samples and FolR1 TCBs. Jurkat NFAT reporter cells are activated after co-incubation with FolR1 TCB (6298) and protease-activated FolR1 TCB containing MMP9-Matriptase cleavage site (8364) in 96 well plate with Matrigel. Protease-activated FolR1 TCBs (8363, 8408) and control TCBs (8409, 7235) do not induce Luciferase expression. The dotted line indicates the baseline Luminescence for Jurkat NFAT cells co-incubated with tumor.

Jurkat NFAT reporter cells are activated after incubation with FolR1 TCB (6298) and tumor samples. Protease-activated FolR1 TCBs (8363, 8408) and control TCBs (8409, 7235) do not induce Luciferase expression. The dotted line indicates the baseline Luminescence for Jurkat NFAT cells co-incubated with tumor (FIGS. 5&6).

Increased Luminescence can be detected for the Jurkat NFAT cells incubated with the malignant tumor sample (FIG. 6) and the protease-activated FolR1 TCB (MMP9-Matriptase. 8364). However no Jurkat NFAT activation can be measured for the benign tumor sample (FIG. 5) and the protease-activated FolR1 TCB (MMP9-Matriptase, 8364).

Example 5

Figure 7A:
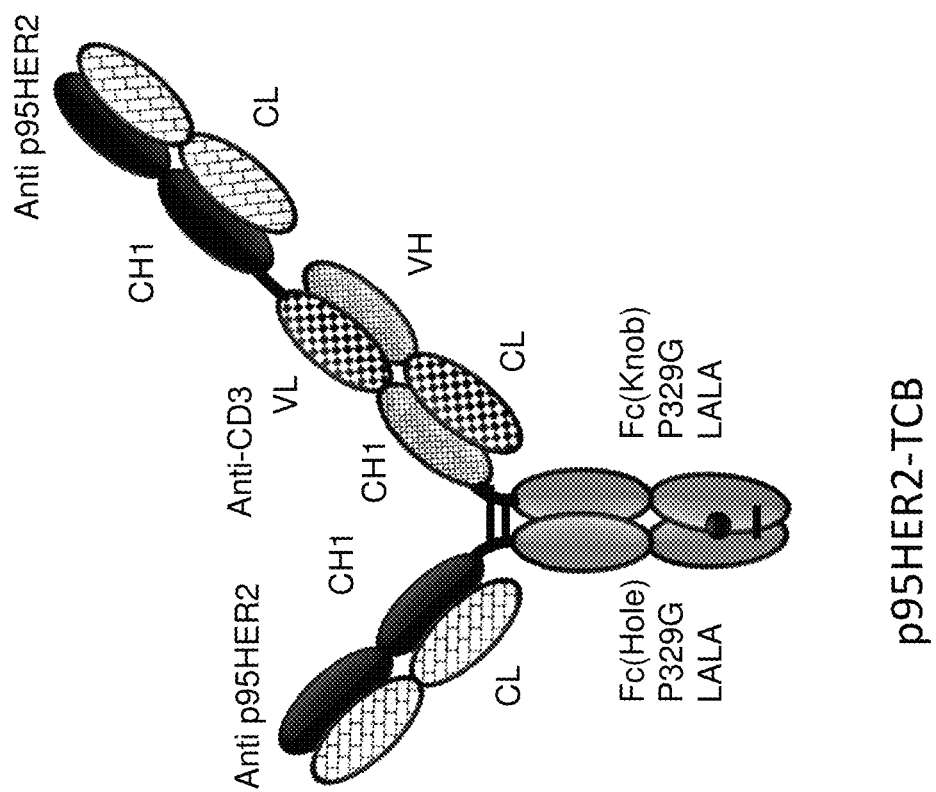
FIG. 7A depicts a schematic of the p95Her2-TCB (SEQ ID NOs: 77, 78, 79, 80).

Jurkat-NFAT Reporter Assay to Monitor Target Expression (p95HER2) in Patient-Derived Xenografts To quantify the activation of T cells induced by p95HER2-TCB (FIG. 7A) in the presence of cells from different patient-derived xenografts (PDX) expanded in immunodeficient mice, we used Jurkat cells expressing an NFAT-driven reporter of TCR activation coupled to luciferase. Fragments of patient samples were implanted into the fat pad of NOD.CB17-Prkdcscid (NOD/SCID) (#SM-NOD-5S-F. Janiver) or NOD.Cg-Prkdcscid Il2rgtm1WjI/SzJ (NSG) (Charles River Laboratories) mice and 17 β-estradiol (1 µM) (#E8875-1G, Sigma) was added to drinking water.

Figures 7B, 7C:
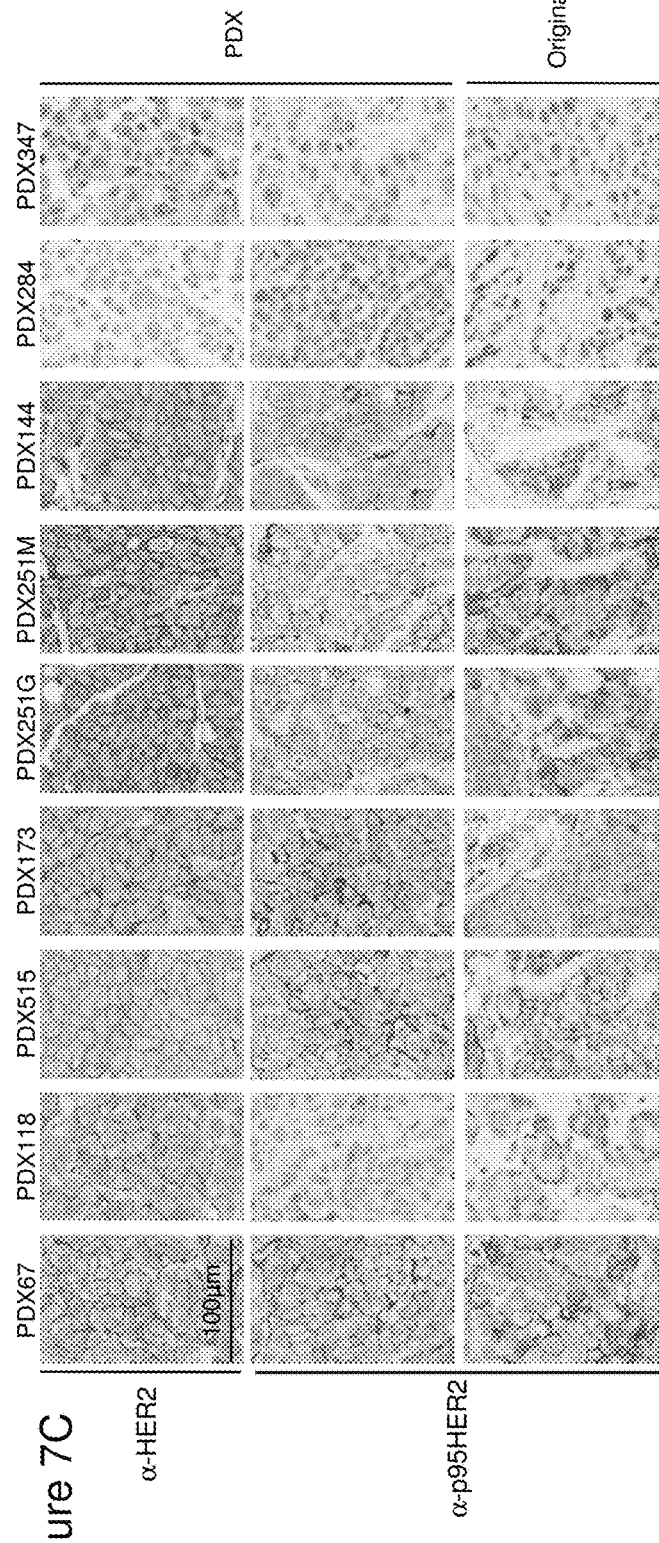
FIG. 7B depicts quantitative analysis of p95Her2 expression of patient-derived xenografts (PDX) or human breast cancer samples.
FIG. 7C depict immunohistological staining of PDXs for HER2 or p95HER2.

Patient-Derived Xenografts or human breast cancer sample tissues were fixed in 4% Formaldehyde buffered to pH=7 (stabilized with methanol) for 24 h and then paraffin-embedded (FFPE). Tissue sections of 4 µm thickness were mounted on positively charged glass slides and immunostained with the indicated antibodies. A certified pathologist evaluated p95HER2 expression by H-score and the percentage of cytokeratin and CD8 positive cells (FIGS. 7B and 7C)

Figure 7D:
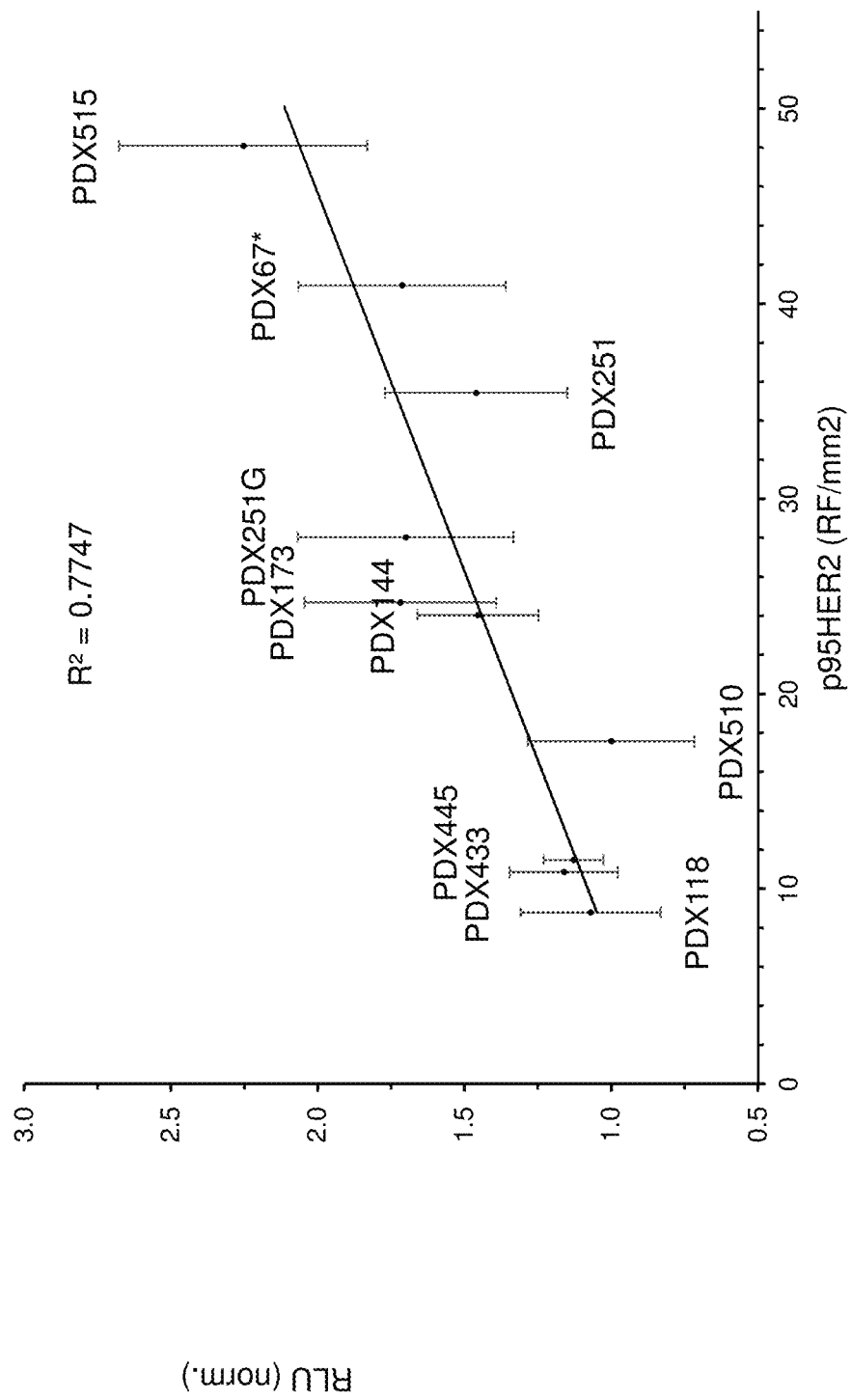
FIG. 7D depicts a correlation analysis of the quantitative IHC-based analysis and the Jurkat-NFAT activation with corresponding samples.

Tumors derived from PDXs were excised and cut into the smallest pieces possible, incubated for 1 h with 200 U/ml Collagenase IA Sigma), washed, filtered through 100 min strainers (Corning) and counted. Single target cells were co-cultured with effector cells at an 5:1 Effector:Target (E:T) ratio in 96-well V bottom plates, in the presence of p95HER2-TCB. The plate was incubated for 16 h at 37° C. in a humidified incubator before it was taken out for Luminescence read out as described before. Observed was a positive correlation between the activation of the T cell response induced by the p95HER2-TCB (FIG. 7D) and the levels of p95HER2 determined by a quantitative IHC-based assay and by immunohistochemistry.

| Exemplary sequences | | |
|---|---|---|
| Construct | Amino acid sequence | SEQ ID NO |
| LC Common light chain pETR13197 | QAVVTQEPSLTVSPGGTVTLTCGSSTGAVTTSNYANWVQEKPGQAFR GLIGGTNKRAPGTPARFSGSLLGGKAALTLSGAQPEDEAEYYCALWY SNLWVFGGGTKLTVLGQPKAAPSVTLFPPSSEELQANKATLVCLISDF YPGAVTVAWKADSSPVKAGVETTTPSKQSNNKYAASSYLSLTPEQW KSHRSYSCQVTHEGSTVEKTVAPTECS | 1 |
| LC Common light chain pETR13197 V region | QAVVTQEPSLTVSPGGTVTLTCGSSTGAVTTSNYANWVQEKPGQAFR GLIGGTNKRAPGTPARFSGSLLGGKAALTLSGAQPEDEAEYYCALWY SNLWVFGGGTKLTVL | 2 |
| anti FolR1 16D5 VH CH1 Fc hole HRYF, pCON983 | EVQLVESGGGLVKPGGSLRLSCAASGFTFSNAWMSWVRWGKGLE WVGRIKSKTDGGTTDYAAPVKGRFTISRDDSKNTLYLQMNSLKTEDT AVYYCTTPWEWSWYDYWGQGTLVTVSSASTKGPSVFPLAYSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGGPSVFLFPPKPKDTLMISRTPEVTCVVVDVSHEDPEVKFNWYVD GVEVHNAKTKPREEQYNSTYRVVSVLTVLHQDWLNGKEYKCKVSNK ALGAPIEKTISKAKGQPREPQVCTLPPSRDELTKNQVSLSCAVKGFYPS DIAVEWESNGQPENNYKTTPPVLDSDGSFFLVSKLTVDKSRWQQGNV FSCSVMHEALHNRFTQKSLSLSPGK | 3 |
| CD3 CH2527-VH3_23-12 CH1 | EVQLLESGGGLVQPGGSLRLSCAASGFTFSTYAMNWVRQAPGKGLE WVSRIRSKYNNYATYYADSVKGRFTISRDDSKNTLYLQMNSLRAEDT | 4 |

-continued

| Exemplary sequences | | |
|---|---|---|
| (G4S)2 FolR1 16D5 VH CH1 Fc knob P329G LALA, pETR13932 | AVYYCVRHGNFGNSYVSWFAYWGQGTLVTVSSASTKGPSVFPLAPSS KSTSGGTAALGCLVKDYFPEPVTVSWNSGALTSGVHTFPAVLQSSGL YSLSSVVTVPSSSLGTQTYICNVNHKPSNTKVDKKVEPKSCDGGGGSG GGGSEVQLVESGGGLVKPGGSLRLSCAASGFTFSNAWMSWVRQAPG KGLEWVGRIKSKTDGGTTDYAAPVKGRFTISRDDSKNTLYLQMNSLK TEDTAVYYCTTPWEWSWYDYWGQGTLVTVSSASTKGPSVFPLAPSS KSTSGGTAALGCLVKDYFPEPVTVSWNSGALTSGVHTEPAVLQSSGL YSLSSVVTVPSSSLGTQTYICNVNHKPSNTKVDKKVEPKSCDKTHTCP PCPAPEAAGGPSVFLFPPKPKDTLMISRTPEVTCVVVDVSHEDPEVKFN WYVDGVEVHNAKTKPREEQYNSTYRVVSVLTVLHQDWLNGKEYKC KVSNKALGAPIEKTISKAKGQPREPQVYTLPPCRDELTKNQVSLWCLV KGFYPSDIAVEWESNGQPENNYKTTPPVLDSDGSFFLYSKLTVDKSRW QQGNVFSCSVMHEALHNHYTQKSLSLSPGK | |
| LC Common light chain pETR13197 | QAVVTQEPSLTVSPGGTVTLTCGSSTGAVTTSNYANWVQEKPGQAFR GLIGGTNKRAPGTPARFSGSLLGGKAALTLSGAQPEDEAEYYCALWY SNLWVFGGGTKLTVLGQPKAAPSVTLFPPSSEELQANKATLVCLISDF YPGAVTVAWKADSSPVKAGVETTTPSKQSNNKYAASSYLSLTPEQW KSHRSYSCQVTHEGSTVEKTVAPTECS | 5 |
| anti CD3 (CH2527 VH_3-23(12) VL7-46(13)) scFv 4.32.63 MMP9 Matriptase MK062 CH2527 VH3_23-VH12 CH1 FolR1 16D5 VH CH1 hum Fc knob PG LALA, pETR16546 | QVQLKESGPGLVAPSQSLSITCTVSGFSLTSYGVSWVRQPPGKCLEWL GIIWGDGSTNYHSALISRLSISKDNSKSQVFLKLNSLQTDDTATYYCAK GITTVVDDYYAMDYWGQGTSVTVSSGGGGSGGGGSGGGGSGGGGS DIQMTQSPASLSASVGETVTITCRASENIDSYLAWYQQKQGKSPQLLV YAATFLADDVPSRFSGSGSGTQYSLKINSTQSEDVARYYCQHYYSTPY TFGCGTKLEIKGGGGSVHMPLGFLGPRQARVVNGGGGGSGGGGSEV QLLESGGGLVQPGGSLRLSCAASGFTFSTYAMNWVRQAPGKGLEWV SRIRSKYNNYATYYADSVKGRFTISRDDSKNTLYLQMNSLRAEDTAV YTYCVRHGNFGNSYVSWFAYWGQGTLVTVSSASTKGPSVFPLAPSSKS TSGGTAALGCLVKDYFPEPVTVSWNSGALTSGVHTFPAVLQSSGLYSL SSVVTVPSSSLGTQTYICNVNHKPSNTKVDKKVEPKSCDGGGGSGGG GSEVQLVESGGGLVKPGGSLRLSCAASGFTFSNAWMSWVRQAPGKG LEWVGRIKSKTDGGTTDYAAPVKGRFTISRDDSKNTLYLQMNSLKTE DTAVYYCTTPWEWSWYDYWGQGTLVTVSSASTKGPSVFPLAPSSKST SGGTAALGCLVKDYFPEPVTVSWNSGALTSGVHTFPAVLQSSGLYSLS SVVTVPSSSLGTQTYICNVNHKPSNTKVDKKVEPKSCDKTHTCPPCPA PEAAGGPSVFLFPPKPKDTLMISRTPEVTCVVVDVSHEDPEVKFNWYV DGVEVHNAKTKPREEQYNSTYRVVSVLTVLHQDWLNGKEYKCKVSN KALGAPIEKTISKAKGQPREPQVYTLPPCRDELTKNQVSLWCLVKGFY PSDIAVEWESNGQPENNYKTTPPVLDSDGSFFLYSKLTVDKSRWQQG NVFSCSVMHEALHNHYTQKSLSLSPGK | 6 |
| FolR1 16D5 VH CH1 Fc hole P329G LALA HRYF, pETR15214 | EVQLVESGGGLVKPGGSLRLSCAASGFTFSNAWMSWVRQAPGKGLE WVGRIKSKTDGGTTDYAAPVKGRFTISRDDSKNTLYLQMNSLKTEDT AVYYCTTPWEWSWYDYWGQGTLVTVSSASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPE AAGGPSVFLFPPKPKDTLMISRTPEVTCVVVDVSHEDPEVKFNWYVD GVEVHNAKTKPREEQYNSTYRVVSVLTVLHQDWLNGKEYKCKVSNK ALGAPIEKTISKAKGQPREPQVCTLPPSRDELTKNQVSLSCAVKGFYPS DIAVEWESNGQPENNYKTTPPVLDSDGSFFLVSKLTVDKSRWQQGNV FSCSVMHEALHNRFTQKSLSLSPGK | 7 |
| anti CD3 (CH2527 VH_3-23(12) VL7-46(13)) scFv 4.32.63 Matriptase MK062 CH2527 VH3_23-VH12 CH1 FolR1 16D5 VH CH1 hum Fc knob PG LALA, pETR15599 | QVQLKESGPGLVAPSQSLSITCTVSGFSLTSYGVSWVRQPPGKCLEWL GIIWGDGSTNYHSALISRLSISKDNSKSQVFLKLNSLQTDDTATYYCAK GITTVVDDYYAMDYWGQGTSVTVSSGGGGSGGGGSGGGGSGGGGS DIQMTQSPASLSASVGETVTITCRASENIDSYLAWYQQKQGKSPQLLV YAATFLADDVPSRFSGSGSGTQYSLKINSTQSEDVARYYCQHYYSTPY TFGCGTKLEIKGGGGSGGGGSRQARVVNGGGGGSGGGGSGGGGSEV QLLESGGGLVQPGGSLRLSCAASGFTFSTYAMNWVRQAPGKGLEWV SRIRSKYNNYATYYADSVKGRFTISRDDSKNTLYLQMNSLRAEDTAV YYCVRHGNFGNSYVSWFAYWGQGTLVTVSSASTKGPSVFPLAPSSKS TSGGTAALGCLVKDYFPEPVTVSWNSGALTSGVHTFPAVLQSSGLYSL SSVVTVPSSSLGTQTYICNVNHKPSNTKVDKKVEPKSCDGGGGSGGG GSEVQLVESGGGLVKPGGSLRLSCAASGFTFSNAWMSWVRQAPGKG LEWVGRIKSKTDGGTTDYAAPVKGRFTISRDDSKNTLYLQMNSLKTE DTAVYYCTTPWEWSWYDYWGQGTLVFVSSASTKGPSVFPLAPSSKST SGGTAALGCLVKDYFPEPVTVSWNSGALTSGVHTFPAVLQSSGLYSLS SVVTVPSSSLGTQTYICNVNHKPSNTKVDKKVERKSCDKTHTCPPCPA PEAAGGPSVFLFPPKPKDTLMISRTPENTCVVVDVSHEDPEVKFNWYV DGVEVHNAKTKPREEQYNSTYRVVSVLTVLHQDWLNGKEYKCKVSN KALGAPIEKTISKAKGQPREPQVYTLPPCRDELTKNQVSLWCLVKGFY PSDIAVEWESNGQPENNYKTTPPVLDSDGSFFLYSKLTVDKSRWQQG NVFSCSVMHEALHNHYTQKSLSLSPGK | 8 |
| anti CD3 (CH2527 VH_3-23(12) VL7- | QVQLKESGPGLVAPSQSLSITCTVSGFSLTSYGVSWVRQPPGKCLEWL GIIWGGGSTNYHSALISRLSISKDNSKSQVFLKLNSLQTDDTATYYCAK | 9 |

Exemplary sequences

| | | |
|---|---|---|
| 46(13)) scFv 4.32.63 non cleavable linker CH2527 VH3_23-VH12 CH1 FolR1 16D5 VH CH1 hum Fc knob PG LALA, pETR15603 | GITTVVDDYYAMDYWGQGTSVTVSSGGGGSGGGGSGGGGSGGGGS DIQMTQSPASLSASVGETVTITCRASENIDSYLAWYQQKGKSPQLLV YAATFLADDVPSRFSGSGSGTQYSLKINSLQSEDVARYYCQHYYSTPY TFGCGTKLEIKGGGGSGGGGSGGGGSGGGGGGSGGGGSGGGGSEV QLLESGGGLVQPGGSLRLSCAASGFTFSTYAMNWVRQAPGKGLEWV SRIRSKYNNYATYYADSVKGRFTISRDDSKNTLYLQMNSLRAEDTAV YYCVRHGNFGNSYVSWFAYWGQGTLVTVSSASTKGPSVFPLAPSSKS TSGGTAALGCLVKDYFPEPVTVSWNSGALTSGVHTFPAVLQSSGLYSL SSVVTVPSSSLGTQTYICNVNHKPSNTKVDKKVEPKSCDGGGGSGGG GSEVQLVESGGGLVKPGGSLRLSCAASGFTFSNAWMSWVRQAPGKG LEWVGRIKSKTDGGTTDYAAPVKGRFTISRDDSKNTLYLQMNSLKTE DTAVYYCTTPWEWSWYDYWGQGTLVTVSSASTKGPSVFPLAPSSKST SGGGTAALGCLVKDYFPEPVTVSWNSGALTSGVHTFPAVLQSSGLYSLS SVVTVPSSSLGTQTYICNVNHKPSNTKVDKKVEPKSCDKTHTCPPCPA PEAAGGPSVFLFPPKPKDTLMISRTPEVTCVVVDVSHEDPEVKFNWYV DGVEVHNAKTKPREEQYNSTYRVVSVLTVLHQDWLNGKEYKCKVSN KALGAPIEKTISKAKGQPREPQVYTLPPCRDELTKNQVSLWCLVKGFY PSDIAVEWESNGQPENNYKTTPPVLDSDGSFFLYSKLTVDKSRWQQG NVFSCSVMHEALHNHYTQKSLSLSPGK | |
| anti CD3 (CH2527 VH_3-23(12) VL7-46(13)) scFv 4.32.63 Cathepsin S/B site CH2527 VH3_23-VH12 CH1 FolR1 16D5 VH CH1 hum Fc knob PG LALA, pETR 16550 | QVQLKESGPGLVAPSQSLSITCTVSGFSLTSYGVSWVRQPPGKCLEWL GIIWGDGSTNYHSALISRLSISKDNSKSQVFLKLNSLQTDDTATYYCAK GITTVVDDYYAMDYWGQGTSVTVSSGGGGSGGGGSGGGGSGGGGS DIQMTQSPASLSASVGETVTITCRASENIDSYLAWYQQKGKSPQLLV YAATFLADDVPSRFSGSGSGTQYSLKINSLQSEDVARYYCQHYYSTPY TFGCGTKLEIKGGGGSGGGGSGGGGSFVGGTGGGGSGGGGSGGSEVQ LLESGGGLVQPGGSLRLSCAASGFTFSTYAMNWVRQAPGKGLEWVS RIRSKYNNYATYYADSVKGRFTISRDDSKNTLYLQMNSLRAEDTAVY YCVRHGNFGNSYVSWFAYWGQGTLVTVSSASTKGPSVFPLAPSSKST SGGTAALGCLVKDYFPEPVTVSWNSGALTSGVHTFPAVLQSSGLYSLS SVVTVPSSSLGTQTYICNVNHKPSNTKVDKKVEPKSCDGGGGSGGGG SEVQLVESGGGLVKPGGSLRLSCAASGFTFSNAWMSWVRQAPGKGL EWVGRIKSKTDGGTTDYAAPVKGRFTISRDDSKNTLYLQMNSLKTED TAVYYCTTPWEWSWYDYWGQGTLVTVSSASTKGPSVFPLAPSSKSTS GGTAALGCLVKDYFPEPVTVSWNSGALTSGVHTFPAVLQSSGLYSLSS VVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYV DGVEVHNAKTKPREEQYNSTYRVVSVLTVLHQDWLNGKEYKCKVSN KALGAPIEKTISKAKGQPREPQVYTLPPCRDELTKNQVSLWCLVKGFY PSDIAVEWESNGQPENNYKTTPPVLDSDGSFFLYSKLTVDKSRWQQG NVFSCSVMHEALHNHYTQKSLSLSPGK | 10 |
| CD3 HCDR1 | TYAMN | 11 |
| CD3 HCDR2 | RIRSKYNNYATYYADSVKG | 12 |
| CD3 HCDR3 | HGNFGNSYVSWFAY | 13 |
| FolR1 HCDR1 | NAWMS | 14 |
| FolR1 HCDR2 | RIKSKTDGGTTDYAAPVKG | 15 |
| FolR1 HCDR3 | PWEWSWYDY | 16 |
| CLC LCDR1 | GSSTGAVTTSNYAN | 17 |
| CLC LCDR2 | GTNKRAP | 18 |
| CLC LCDR3 | ALWYSNLWV | 19 |
| Anti ID 4.32.63 CDR H1 Kabat | SYGVS | 20 |
| Anti ID 4.32.63 CDR H2 Kabat | IIWGDGSTNYHSALIS | 21 |
| Anti ID 4.32.63 CDR H3 Kabat | GITTVVDDYYAMDY | 22 |
| Anti ID 4.32.63 CDR L1 Kabat | RASENIDSYLA | 23 |
| Anti ID 4.32.63 CDR L2 Kabat | AATFLAD | 24 |
| Anti ID 4.32,63 CDR L3 Kabat | QHYYSTPYT | 25 |

-continued

| Exemplary sequences | | |
|---|---|---|
| Anti-CD3 variable heavy chain (VH) | EVQLLESGGGLVQPGGSLRLSCAASGFTFSTYAMNWVRQAPGKGLE WVSRIRSKYNNYATYYADSVKGRFTISRDDSKNTLYLQMNSLRAEDT AVYYCVRHGNFGNSYVSWFAYWGQGTLVTVSS | 26 |
| Anti-FolR1 16D5 variable heavy chain (VH) | EVQLVESGGGLVKPGGSLRLSCAASGFTFSNAWMSWVRQAPGKGLE WVGRIKSKTDGGTTDYAAPVKGRFTISRDDSKNTLYLQMNSLKTEDT AVYYCTTPWEWSWYDYWGQGTLVTVSS | 27 |
| LC Common variable light chain (VL) | QAVVTQEPSLTVSPGGTVTLTCGSSTGAVTTSNYANWVQEKPGQAFR GLIGGTNKRAPGTPARFSGSLLGKAALTLSGAQPEDEAEYYCALWY SNLWVFGGGTKLTVL | 28 |
| 4.32.63 Anti-idiotypic scFv | QVQLKESGPGLVAPSQSLSITCTVSGFSLTSYGVSWVRQPPGKCLEWL GIIWGDGSTNYHSALISRLSISKDNSKSQVFLKLNSLQTDDTATYYCAK GITTVVDDYYNMDYWGQGTSVTVSSGGGGSGGGGSGGGGSGGGGS DIQMTQSPASLSASVGETVTITCRASENIDSYLAWYQQKQGKSPQLLV YAATFLADDVPSRFSGSGSGTQYSLKINSLQSEDVARYYCQHYYSTPY TFGCGTKLEIK | 29 |
| Linker 1 | GGGGSGGGGSRQARVVNGGGGGSGGGGSGGGGS | 30 |
| Linker 2 | GGGGSVHMPLGFLGPGRSRGSFPGGGGS | 31 |
| Linker 3 | GGGGSGGGGSRQARVVNGGGGGSVPLSLYSGGGGGSGGGGS | 32 |
| Linker 4 | GGGGSGGGGSRQARVVNGVPLSLYSGGGGGSGGGGS | 33 |
| Linker 5 | GGGGSVHMPLGFLGPRQARVVNGGGGGSGGGGS | 34 |
| Linker 6 | GGGGSVHMPLGFLGPRQARVVNGGGGGSGGGGSGG | 35 |
| Linker 7 | GGGGSGGGGSGGGGSFVGGTGGGGSGGGGSGGS | 36 |
| Linker 8 | GGGGSGGGGSKKAAPVNGGGGGSGGGGSGGGGS | 37 |
| Linker 9 | GGGGSGGGGSPMAKKVNGGGGGSGGGGSGGGGS | 38 |
| Linker 10 | GGGGSGGGGSQARAKVNGGGGGSGGGGSGGGGS | 39 |
| Linker 11 | GGGGSEGGGSVHMPLGFLGPGGGGSGGGGSGGS | 40 |
| Linker 12 | GGGGSGGGGSQARAKGGGGSGGGGSGGGGSGGS | 41 |
| Linker 13 | GGGGSVHMPLGFLGPPMAKKGGGGSGGGGSGGS | 42 |
| Linker 14 | GGGGSGGGGSKKAAPGGGGSGGGGSGGGGSGGS | 43 |
| Linker 15 | GGGGSGGGGSPMAKKGGGGSGGGGSGGGGSGGS | 44 |
| Recognition site 1 | RQARVVNG | 45 |
| Recognition site 2 | VHMPLGFLGPGRSRGSFP | 46 |
| Recognition site 3 | RQARVVNGXXXXXVPLSLYSG | 47 |
| Recognition site 4 | RQARVVNGVPLSLYSG | 48 |
| Recognition site 5 | PLGLWSQ | 49 |
| Recognition site 6 | VHMPLGFLGPRQARVVNG | 50 |
| Recognition site 7 | FVGGTG | 51 |
| Recognition site 8 | KKAAPVNG | 52 |
| Recognition site 9 | PMAKKVNG | 53 |
| Recognition site 10 | QARAKVNG | 54 |
| Recognition site 11 | VHMPLGFLGP | 55 |
| Recognition site 12 | QARAK | 56 |
| Recognition site 13 | VHMPLGFLGPPMAKK | 57 |
| Recognition site 14 | KKAAP | 58 |

-continued

| | Exemplary sequences | |
|---|---|---|
| Recognition site 15 | PMAKK | 59 |
| hu CD3e | MQSGTHWRVLGLCLLSVGVWGQDGNEEMGGITQTPYKVSISGTTVIL TCPQYPGSEILWQHNDKNIGGDEDDKNIGSDEDHLSLKEFSELEQSGY YVCYPRGSKPEDANFYLYLRARVCENCMEMDVMSVATIVIVDICITG GLLLLVYYWSKNRKAKAKPVTRGAGAGGRQRGQNKERPPPVPNPDY EPIRKGQRDLYSGLNQRRI | 60 |

| Construct | DNA sequence | SEQ ID NO: |
|---|---|---|
| anti FolR1 16D5 VH CH1 Fc hole HRYF, pCON983 | GAGGTGCAATTGGTTGAATCTGGTGGTGGTCTGGTAAAACCGGGC GGTTCCCTGCGTCTGAGCTGCGCGGCTTCCGGATTCACCTTCTCCA ACGCGTGGATGAGCTGGGTTCGCCAGGCCCCGGGCAAAGGCCTCG AGTGGGTTGGTCGTATCAAGTCTAAAACTGACGGTGGCACCACGG ATTACGCGGCTCCAGTTAAAGGTCGTTTTACCATTTCCCGCGACGA TAGCAAAAACACTCTGTATCTGCAGATGAACTCTCTGAAAACTGAA GACACCGCAGTCTACTACTGTACTACCCCGTGGGAATGGTCTTGGT ACGATTATTGGGGCCAGGGCACGCTGGTTACGGTGTCTTCCGCTAG CACCAAGGGCCCCTCCGTGTTCCCCCTGGCCCCCAGGAGCAAGAGC ACCAGCGGCGGCACAGCCGCTCTGGGCTGCCTGGTCAAGGACTAC TTCCCCGAGCCCGTGACCGTGTCCTGGAACAGCGGAGCCCTGACCT CCGGCGTGCACACCTTCCCCGCCGTGCTGCAGAGTTCTGGCCTGTA TAGCCTGAGCAGCGTGGTCACCGTGCCTTCTAGCAGCCTGGGCACC CAGACCTACATCTGCAACGTGAACCACAAGCCCAGCAACACCAAG GTGGACAAGAAGGTGGAGCCCAAGAGCTGCGACAAAACTCACACA TGCCCACCGTGCCCAGCACCTGAAGCTGCAGGGGGACCGTCAGTCT TCCTCTTCCCCCCAAAACCCAAGGACACCCTCATGATCTCCCGGAC CCCTGAGGTCACATGCGTGGTGGTGGACGTGAGCCACGAAGACCC TGAGGTCAAGTTCAACTGGTACGTGGACGGCGTGGAGGTGCATAA TGCCAAGACAAAGCCGCGGGAGGAGCAGTACAACAGCACGTACCG TGTGGTCAGCGTCCTCACCGTCCTGCACCAGGACTGGCTGAATGGC AAGGAGTACAAGTGCAAGGTCTCCAACAAAGCCCTCGGCGCCCCC ATCGAGAAAACCATCTCCAAAGCCAAAGGGCAGCCCCGAGAACCA CAGGTGTGCACCCTGCCCCCATCCCGGGATGAGCTGACCAAGAAC CAGGTCAGCCTCTCGTGCGCAGTCAAAGGCTTCTATCCCAGCGACA TCGCCGTGGAGTGGGAGAGCAATGGGCAGCCGGAGAACAACTACA AGACCACGCCTCCCGTGCTGGACTCCGACGGCTCCTTCTTCCTCGT GAGCAAGCTCACCGTGGACAAGAGCAGGTGGCAGCAGGGGAACGT CTTCTCATGCTCCGTGATGCATGAGGCTCTGCACAACCGCTTCACG CAGAAGAGCCTCTCCCTGTCTCCGGGTAAATGA | 61 |
| CD3 CH2527-CH3_23-12 CH1 (G4S)2 FolR1 16D5 VH CH1 Fc knob P329G LALA, pETR13932 | GAGGTGCAGCTGCTGGAATCTGGCGGCGGACTGGTGCAGCCTGGC GGATCTCTGAGACTGAGCTGTGCCGCCAGCGGCTTCACCTTCAGCA CCTACGCCATGAACTGGGTGCGCCAGGCCCCTGGCAAAGGCCTGG AATGGGTGTCCCGGATCAGAAGCAAGTACAACAACTACGCCACCT ACTACGCCGACAGCGTGAAGGGCCGGTTCACCATCAGCCGGGACG ACAGCAAGAACACCCTGTACCTGCAGATGAACAGCCTGCGGGCCG AGGACACCGCCGTGTACTATTGTGTGCGGCACGGCAACTTCGGCAA CAGCTATGTGTCTTGGTTTGCCTACTGGGGCCAGGGCACCCTCGTG ACCGTGTCATCTGCTAGCACAAAGGGCCCCTAGCGTGTTCCCTCTGG CCCCCAGCAGCAAGAGCACAAGCGGCGGAACAGCCGCCCTGGGCT GCCTCGTGAAGGACTACTTCCCCGAGCCCGTGACAGTGTCTTGGAA CAGCGGAGCCCTGACAAGCGGCGTGCACACCTTCCCTGCCGTGCTG CAGAGCAGCGGCCTGTACTCCCTGAGCAGCGTGGTCACCGTGCCTA GCAGCAGCCTGGGCACCCAGACCTACATCTGCAACGTGAACCACA AGCCCAGCAACACCAAAGTGGACAAGAAGGTGGAGCCCAAGAGCT GTGATGGCGGAGGAGGGTCCGGAGGCGGAGGATCCGAGGTGCAAT TGGTTGAATCTGGTGGTGGTCTGGTAAAACCGGGCGGTTCCCTGCG TCTGAGCTGCGCGGCTTCCGGATTCACCTTCTCCAACGCGTGGATG AGCTGGGTTCGCCAGGCCCCGGGCAAAGGCCTCGAGTGGGTTGGT CGTATCAAGTCTAAAACTGACGGTGGCACCACGGATTACGCGGCTC CAGTTAAAGGTCGTTTTACCATTTCCCGCGACGATAGCAAAAACAC TCTGTATCTGCAGATGAACTCTCTGAAAACTGAAGACACCGCAGTC TACTACTGTACTACCCCGTGGGAATGGTCTTGGTACGATTATTGGG GCCAGGGCACGCTGGTTACGGTGTCTAGCGCTAGTACCAAGGGCC CCAGCGTGTTCCCCCTGGCACCCAGCAGCAAGAGCACATCTGGCG GAACAGCCGCTTCTGGGCTGTCTGGTGAAAGACTACTTCCCCGAGCC CGTGACCGTGTCTTGGAACTCTGGCGCCCTGACCAGCGGCGTGCAC ACCTTTCCAGCGTGCTGCAGAGCAGCGGCCTGTACTCCCTGTCCT CCGTGGTCACCGTGCCCTCTAGCTCCCTGGGAACACAGACATATAT CTGTAATGTCAATCACAAGCCTTCCAACACCAAAGTCGATAAGAA AGTCGAGCCCAAGAGCTGCGACAAAACTCACACATGCCCACCGTG CCCAGCACCTGAAGCTGCAGGGGGACCGTCAGTCTTCCTCTTCCCC CCAAAACCCAAGGACACCCTCATGATCTCCCGGACCCCTGAGGTCA CATGCGTGGTGGTGGACGTGAGCCACGAAGACCCTGAGGTCAAGT | 62 |

| Exemplary sequences | | |
|---|---|---|
| | TCAACTGGTACGTGGACGGCGTGGAGGTGCATAATGCCAAGACAA<br>AGCCGCGGGAGGAGCAGTACAACAGCACGTACCGTGTGGTCAGCG<br>TCCTCACCGTCCTGCACCAGGACTGGCTGAATGGCAAGGAGTACA<br>AGTGCAAGGTCTCCAACAAAGCCCTCGGCGCCCCCATCGAGAAAA<br>CCATCTCCAAAGCCAAAGGGCAGCCCCGAGAACCACAGGTGTACA<br>CCCTGCCCCCATGCCGGGATGAGCTTGACCAAGAACCAGGTCAGCC<br>TGTGGTGCCTGGTCAAAGGCTTCTATCCCAGCGACATCGCCGTGGA<br>GTGGGAGAGCAATGGGCAGCCGGAGAACAACTACAAGACCACGCC<br>TCCCGTGCTGGACTCCGACGGCTCCTTCTTCCTCTACAGCAAGCTC<br>ACCGTGGACAAGAGCAGGTGGCAGCAGGGGAACGTCTTCTCATGC<br>TCCGTGATGCATGAGGCTCTGCACAACCACTACACGCAGAAGAGC<br>CTCTCCCTGTCTCCGGGTAAATGA | |
| LC Common light chain pETR13197 | CAGGCCGTCGTGACCCAGGAACCCAGCCTGACAGTGTCTCCTGGCG<br>GCACCGTGACCCTGACATGTGGCAGTTCTACAGGCGCCGTGACCAC<br>CAGCAACTACGCCAACTGGGTGCAGGAAAAGCCCGGCCAGGCCTT<br>CAGAGGACTGATCGGCGGCACCAACAAGAGAGCCCCTGGCACCCC<br>TGCCAGATTCAGCGGATCTCTGCTGGGAGGAAAGGCCGCCCTGAC<br>ACTGTCTGGCGCCCAGCCAGAAGATGAGGCCGAGTACTACTGCGC<br>CCTGTGGTACAGCAACCTGTGGGTGTTCGGCGAGGCACCAAGCT<br>GACAGTCCTAGGTCAACCCAAGGCTGCCCCCAGCGTGACCCTGTTC<br>CCCCCCAGCAGCGAGGAACTGCAGGCCAACAAGGCCACCCTGGTC<br>TGCCTGATCAGCGACTTCTACCCAGGCGCCGTGACCGTGGCCTGGA<br>AGGCCGACAGCAGCCCCGTGAAGGCCGGCGTGGAGACCACCACCC<br>CCAGCAAGCAGAGCAACAACAAGTACGCCGCCAGCAGCTACCTGA<br>GCCTGACCCCCGAGCAGTGGAAGAGCCACAGGTCCTACAGCTGCC<br>AGGTGACCCACGAGGGCAGCACCGTGGAGAAAACCGTGGCCCCCA<br>CCGAGTGCAGCTGA | 63 |
| anti CD3 (CH2527 VH_3-23(12) VL7-46(13)) scFv 4.32.63 MNP9 Matriptase MK062 CH2527 VH3_23-VH12 CH1 FolRI 16D5 VH CH1 hum Fc knob PG LALA pETR16546 | CAAGTGCAGCTGAAAGAGTCCGGCCCTGGACTGGTGGCCCCTAGC<br>CAGAGCCTGAGCATCACCTGTACCGTGTCCGGCTTCAGCCTGACCA<br>GCTACGGCGTGTCATGGGTGCGCCAGCCTCCAGGCAAGTGTCTGGA<br>ATGGCTGGGCATCATCTGGGGCGACGGCAGCACCAATTACCACAG<br>CGCCCTGATCAGCAGACTGAGCATCTCCAAGGACAACAGCAAGAG<br>CCAGGTGTTCCTGAAGCTGAACAGCCTGCAGACCGACGACACCGC<br>CACCTACTACTGCGCCAAGGGCATCACCACCGTGGTGGACGACTAC<br>TACGCTATGGACTACTGGGGCCAGGGCACCCAGCGTGACAGTGTCT<br>AGCGGAGGCGGAGGATCTGGCGGCGGAGGAAGTGGCGGAGGGGG<br>ATCTGGGGGAGGCGGAAGCGATATCCAGATGACCCAGAGCCCTGC<br>CAGCCTGTCTGCCTCTGTGGGCGAGACAGTGACCATCACATGCCGG<br>GCCAGCGAGAACATCGACAGCTACCTGGCCTGGTATCAGCAGAAG<br>CAGGGCAAGAGCCCCCAGCTGCTGGTGTACGCCGCCACCTTTCTGG<br>CCGACGATGTGCCCAGCAGATTCAGCGGCAGCGGAAGCGGCACAC<br>AGTACAGCCTGAAGATCAACTCCCTGCAGAGCGAGGACGTGGCCC<br>GGTACTACTGCCAGCACTACTACAGCACCCCCTACACCTTCGGCTG<br>CGGCACCAAGCTGGAAATCAAAGGAGGCGGCGGAAGTGTGCACAT<br>GCCCCTGGGCTTCCTGGGCCCCAGACAGGCCAGAGTCGTGAACGG<br>GGGGGGCGGAGGCAGTGGGGGGGAGGATCCGAGGTGCAGCTGC<br>TGGAATCTGGCGGCGGACTGGTGCAGCCTGGCGGATCTCTGAGACT<br>GAGCTGTGCCGCCAGCGGCTTCACCTTCAGCACCTACGCCATGAAC<br>TGGGTGCGCCAGGCCCCTGGCAAAGGCCTGGAATGGGTGTCCGG<br>ATCAGAAGCAAGTACAACAACTACGCCACCTACTACGCCGACAGC<br>GTGAAGGGCCGGTTCACCATCAGCCGGGACGACAGCAAGAACACC<br>CTGTACCTGCAGATGAACAGCCTGCGGGCCGAGGACACCGCCGTG<br>TACTATTGTGTGCGGCACGGCAACTTCGGCAACAGCTATGTGTCTT<br>GGTTTGCCTACTGGGGCCAGGGCACCCTCGTGACCGTGTCAAGCGC<br>TAGCACAAAGGGCCGTAGCGTGTTCCCTCTGGCCCCCAGCAGCAAG<br>AGCACAAGCGGCGGAACAGCCGCCCTGGGCTGCCTCGTGAAGGAC<br>TACTTCCCCGAGCCCGTGACAGTGTCTTGGAACAGCGGAGCCCTGA<br>CAAGCGGCGTGCACACCTTCCCTGCCGTGCTGCAGAGCAGCGGCCT<br>GTACTCCCTGAGCAGCGTGGTCACCGTGCCTAGCAGCAGCCTGGGC<br>ACCCAGACCTACATCTGCAACGTGAACCACAAGCCCAGCAACACC<br>AAAGTGGACAAGAAGGTGGAGCCCAAGAGCTGTGATGGCGGAGG<br>AGGGTCCGGGGGCGGAGGATCCGAGGTGCAATTGGTTGAATCTGG<br>TGGTGGTCTGGTAAAACCGGGCGGTTCCCTGCGTCTGAGCTGCGCG<br>GCTTCCGGGTTCACCTTCTCCAACGCGTGGATGAGCTGGGTTCGCC<br>AGGCCCCGGGCAAAGGCCTCGAGTGGGTTGGTCGTATCAAGTCTA<br>AAACTGACGGTGGCACCACGGATTACGCGGCTCCAGTTAAAGGTC<br>GTTTTACCATTTCCCGCGACGATAGCAAAAACACTCTGTATCTGCA<br>GATGAACTCTCTGAAAACTGAAGACACCGCAGTCTACTACTGTACT<br>ACCCCGTGGGAATGGTCTTGGTACGATTATTGGGGCCAGGGCACGC<br>TGGTTACGGTGTCTAGCGCTAGTACCAAGGGCCCCAGCGTGTTCCC<br>CCTGGCACCCAGCAGCAAGAGCACATCTGGCGGAACAGCCGCTCT<br>GGGCTGTCTGGTGAAAGACTACTTCCCCGAGCCCGTGACCGTGTCT<br>TGGAACTCTGGCGCCCTGACCAGCGGCGTGCACACCTTTCCAGCCG<br>TGCTGCAGAGCAGCGGCCTGTACTCCCTGTCCTCCGTGGTCACCGT<br>GCCCTCTAGCTCCCTGGGAACACAGACATATATCTGTAATGTCAAT | 64 |

| Exemplary sequences | | |
|---|---|---|
| | CACAAGCCTTCCAACACCAAAGTCGATAAGAAAGTCGAGCCCAAG<br>AGCTGCGACAAAACTCACACATGCCCACCGTGCCCAGCACCTGAA<br>GCTGCAGGGGGACCGTCAGTCTTCCTCTTCCCCCCAAAACCCAAGG<br>ACACCCTCATGATCTCCCGGACCCCTGAGGTCACATGCGTGGTGGT<br>GGACGTGAGCCACGAAGACCCTGAGGTCAAGTTCAACTGGTACGT<br>GGACGGCGTGGAGGTGCATAATGCCAAGACAAAGCCGCGGGAGG<br>AGCAGTACAACAGCACGTACCGTGTGGTCAGCGTCCTCACCGTCCT<br>GCACCAGGACTGGCTGAATGGCAAGGAGTACAAGTGCAAGGTCTC<br>CAACAAAGCCCTCGGCGCCCCCATCGAGAAAACCATCTCCAAAGC<br>CAAAGGGCAGCCCCGAGAACCACAGGTGTACACCCTGCCCCCATG<br>CCCGGGATGAGCTGACCAAGAACCAGGTCAGCCTGTGGTGCCTGGT<br>CAAAGGCTTCTATCCCAGCGACATCGCCGTGGAGTGGGAGAGCAA<br>TGGGCAGCCGGAGAACAACTACAAGACCACGCCTCCCGTGCTGGA<br>CTCCGACGGCTCCTTCTTCCTCTACAGCAAGCTCACCGTGGACAAG<br>AGCAGGTGGCAGCAGGGGAACGTCTTCTCATGCTCCGTGATGCATG<br>AGGCTCTGCACAACCACTACACGCAGAAGAGCCTCTCCCTGTCTCC<br>GGGTAAATGA | |
| anti CD (CH2527<br>VH_3-23(12) VL7-<br>46(13)) scFv<br>4.32.63 Cathepsin<br>S/B site CH2527<br>VH3_23-VH12<br>CH1 FolR1 16D5<br>VH CH1 hum Fc<br>knob PG LALA,<br>pETR16550 | CAAGTGCAGCTGAAAGAGTCCGGCCCTGGACTGGTGGCCCCTAGC<br>CAGAGCCTGAGCATCACCTGTACCGTGTCCGGCTTCAGCCTGACCA<br>GCTACGGCGTGTCATGGGTGCGCCAGCCTCCAGGCAAGTGTCTGGA<br>ATGGCTGGGCATCATCTGGGCGACGGCAGCACCAATTACCACAG<br>CGCCCTGATCAGGAGACTGAGCATCTCCAAGGACAACAGCAAGAG<br>CCAGGTGTTCCTGAAGCTGAACAGCCTGCAGACCGACGACACCGC<br>CACCTACTACTGCGCCAAGGGCATCACCACCGTGGTGGACGACTAC<br>TACGCTATGGACTACTGGGGCCAGGGCACCAGCGTGACAGTGTCT<br>AGCGGAGGCGGAGGATCTGGCGGCGGAGGAAGTGGCGGAGGGGG<br>ATCTGGGGGAGGCGGAAGCGATATCCAGATGACCCAGAGCCCTGC<br>CAGCCTGTCTGCCTCTGTGGGCGAGACAGTGACCATCACATGCCGG<br>GCCAGCGAGAACATCGACAGCTACCTGGCCTGGTATCAGCAGAAG<br>CAGGGCAAGAGCCCCCAGCTGCTGGTGTACGCCGCCACCTTTCTGG<br>CCGACGATGTGCCCAGCAGATTCAGCGGCAGCGGAAGCGGCACAC<br>AGTACAGCCTGAAGATCAACTCCCTGCAGAGCGAGGACGTGGCCC<br>GGFACTACTGCCAGCACTACTACAGCACCCCCTACACCTTCGGCTG<br>CGGCACCAAGCTGGAAATCAAAGGCGGGGGAGGCTCCGGAGGCG<br>GCGGAAGTGGAGGCGGCGGAAGTTTCGTGGGGGGGACCGGGGGC<br>GGAGGCAGTGGGGGGGGAGGATCCGGGGGATCCGAGGTGCAGCT<br>GCTGGAATCTGGCGGCGACTGGTGCAGCCTGGCGGATCTCTGAG<br>ACTGAGCTGTGCCGCCAGCGGCTTCACCTTCAGCACCTACGCCATG<br>AACTGGGTGCGCCAGGCCCCTGGCAAAGGCCTGGAATGGGTGTCC<br>CGGATCAGAAGCAAGTACAACAACTACGCCACCTACTACGCCGAC<br>AGCGTGAAGGGCCGGTTCACCATCAGCCGGGACGACAGCAAGAAC<br>ACCCTGTACCTGCAGATGAACAGCCTGCGGGCCGAGGACACCGCC<br>GTGTACTATTGTGTGCGGCACGGCAACTTCGGCAACAGCTATGTGT<br>CTTGGTTTGCCTACTGGGGCCAGGGCACCCTCGTGACCGTGTCAAG<br>CGCTAGCACAAAGGGCCCTAGCGTGTTCCCTCTGGCCCCCAGCAGC<br>AAGAGCACAAGCGGCGGAACAGCCGCCCTGGGCTGCCTCGTGAAG<br>GACTACTTCCCCGAGCCCGTGACAGTGTCTTGGAACAGCGGAGCCC<br>TGACAAGCGGCGTGCACACCTTCCCTGCCGTGCTGCAGAGCAGCG<br>GCCTGTACTCCCTGAGCAGCGTGGTCACCGTGCCTAGCAGCAGCCT<br>GGGCACCCAGACCTACATCTGCAACGTGAACCACAAGCCCAGCAA<br>CACCAAAGTGGACAAGAAGGTGGAGCCCAAGAGCTGTGATGGCGG<br>AGGAGGGTCCGGGGGCGGAGGATCCGAGGTGCAATTGGTTGAATC<br>TGGTGGTGGTCTGGTAAAACCGGGCGGTTCCCTGCGTCTGAGCTGC<br>GCGGCTTCCGGGTTCACCTTCTCCAACGCGTGGATGAGCTGGGTTC<br>GCCAGGCCCCGGGCAAAGGCCTGAGTGGGTTGGTCGTATCAAGT<br>CTAAAACTGACGGTGGCACCACGGATTACGCGGCTCCAGTTAAAG<br>GTCGTTTTACCATTTCCCGCGACGATAGCAAAAACACTCTGTATCT<br>GCAGATGAACTCTCTGAAAACTGAAGCACCGCAGTCTACTACTGT<br>ACTACCCCGTGGGAATGGTCTTGGTACGATTATTGGGGCCAGGGCA<br>CGCTGGTTACGGTGTCTAGCGCTAGTACCAAGGGCCCCAGCGTGTT<br>CCCCCTGGCACCCAGCAGCAAGAGCACATCTGGCGGAACAGCCGC<br>TCTGGGCTGTCTGGTGAAAGACTACTTCCCCGAGCCCGTGACCGTG<br>TCTTGGAACTCTGGCGCCCTGACCAGCGGCGTGCACACCTTTCCAG<br>CCGTGCTGCAGAGCAGCGGCCTGTACTCCCTGTCCTCCGTGGTCAC<br>CGTGCCCTCTAGCTCCCTGGGAACACAGACATATATCTGTAATGTC<br>AATCACAAGCCTTCCAACACCAAAGTCGATAAGAAAGTCGAGCCC<br>AAGAGCTGCGACAAAACTCACACATGCCCACCGTGCCCAGCACCT<br>GAAGCTGCAGGGGGACCGTCAGTCTTCCTCTTCCCCCCAAAACCCA<br>AGGACACCCTCATGATCTCCCGGACCCCTGAGGTCACATGCGTGGT<br>GGTGGACGTGAGCCACGAAGACCCTGAGGTCAAGTTCAACTGGTA<br>CGTGGACGGCGTGGAGGTGCATAATGCCAAGACAAAGCCGCGGGA<br>GGAGCAGTACAACAGCACGTACCGTGTGGTCAGCGTCCTCACCGTC<br>CTGCACCAGGACTGGCTGAATGGCAAGGAGTACAAGTGCAAGGTC<br>TCCAACAAAGCCCTCGGCGCCCCCATCGAGAAAACCATCTCCAAA<br>GCCAAAGGGCAGCCCCGAGAACCACAGGTGTACACCCTGCCCCCA<br>TGCCCGGGATGAGCTGACCAAGAACCAGGTCAGCCTGTGGTGCCTG | 65 |

| Exemplary sequences | | |
|---|---|---|
| | GTCAAAGGCTTCTATCCCAGCGACATCGCCGTGGAGTGGGAGAGC<br>AATGGGCAGCCGGAGAACAACTACAAGACCACGCCTCCCGTGCTG<br>GACTCCGACGGCTCCTTCTTCCTCTACAGCAAGCTCACCGTGGACA<br>AGAGCAGGTGGCAGCAGGGGAACGTCTTCTCATGCTCCGTGATGC<br>ATGAGGCTCTGCACAACCACTACACGCAGAAGAGCCTCTCCCTGTC<br>TCCGGGTAAATGA | |
| anti CD3 (CH2527<br>VH_3-23(12) VL7-<br>46(13)) scFv<br>4.32.63 Matriptase<br>MK062 CH2527<br>VH3_23-VH12<br>CH1 FolR1 16D5<br>VH CH1 hum Fc<br>knob PG LALA,<br>pETR15599 | CAAGTGCAGCTGAAAGAGTCCGGCCCTGGACTGGTGGCCCCTAGC<br>CAGAGACCTGAGCATCACCTGTACCGTGTCCGGCTTCAGCCTGACCA<br>GCTACGGCGTGTCATGGGTGCGCCAGCCTCCAGGCAAGTGTCTGGA<br>ATGGCTGGGCATCATCTGGGGCGACGGCAGCACCAATTACCACAG<br>CGCCCTGATCAGCAGACTGAGCATCTCCAAGGACAACAGCAAGAG<br>CCAGGTGTTCCTGAAGCTGAACAGCCTGCAGACCGACGACACCGC<br>CACCTACTACTGCGCCAAGGGCATCACCACCGTGGTGGACGACTAC<br>TACGCTATGGACTACTGGGGCCAGGGCACCAGCGTGACAGTGTCT<br>AGCGGAGGCGGAGGATCTGGCGGCGGAGGAAGTGGCGGAGGGGG<br>ATCTGGGGGAGGCGGAAGCGATATCCAGATGACCCAGAGCCCTGC<br>CAGCCTGTCTGCCTCTGTGGGCGAGACAGTGACCATCACATGCCGG<br>GCCAGCGAGAACATCGACAGCTACCTGGCCTGGTATCAGCAGAAG<br>CAGGGCAAGAGCCCCCAGCTGCTGGTGTACGCCGCCACCTTTCTGG<br>CCGACGATGTGCCCAGCAGATTCAGCGGCAGCGGAAGCGGCACAC<br>AGTACAGCCTGAAGATCAACTCCCTGCAGAGCGAGGACGTGGCCC<br>GGTACTACTGCCAGCACTACTACAGCACCCCCTACACCTTCGGCTG<br>CGGCACCAAGCTGGAAATCAAAGGCGGGGGAGGCTCCGGAGGCG<br>GCGGAAGTAGACAGGCCAGAGTCGTGAACGGGGAGGGGGGGGA<br>AGTGGGGGCGGAGGCAGTGGGGGCGGAGGATCCGAGGTGCAGCT<br>GCTGGAATCTGGCGGCGGACTGGTGCAGCCTGGCGGATCTCTGAG<br>ACTGAGCTGTGCCGCCAGCGGCTTCACCTTCAGCACCTACGCCATG<br>AACTGGGTGCGCCAGGCCCCTGGCAAAGGCCTGGAATGGGTGTCC<br>CGGATCAGAAGCAAGTACAACAACTACGCCACCTACTACGCCGAC<br>AGCGTGAAGGGCCGGTTCACCATCAGCCGGGACGACAGCAAGAAC<br>ACCCTGTACCTGCAGATGAACAGCCTGCGGGCCGAGGACACCGCC<br>GTGTACTATTGTGTGCGGCACGGCAACTCCGCAACAGCTATGTGT<br>CTTGGTTTGCCTACTGGGGCCAGGGCACCCTCGTGACCGTGTCAAG<br>CGCTAGCACAAAGGGCCCTAGCGTGTTCCCTCTGGCCCCCAGCAGC<br>AAGAGCACAAGCGGCGGAACAGCCGCCCTGGGCTGCCTCGTGAAG<br>GACTACTTCCCCGAGCCCGTGACAGTGTCTTGGAACAGCGGAGCCC<br>TGACAAGCGGCGTGCACACCTTCCCTGCCGTGCTGCAGAGCAGCG<br>GCCTGTACTCCCTGAGCAGCGTGGTCACCGTGCCTAGCAGCAGCCT<br>GGGCACCCAGACCTACATCTGCAACGTGAACCACAAGCCCAGCAA<br>CACCAAAGTGGACAAGAAGGTGGAGCCCAAGAGCTGTGATGGCAC<br>AGGAGGGTCCGGGGGCGGAGGATCCGAGGTGCAATTGGTTGAATC<br>TGGTGGTGGTCTGGTAAAACCGGGCGGTTCCCTGCGTCTGAGCTGC<br>GCGGCTTCCGGGTTCACCTTCTCCAACGCGTGGATGAGCTGGGTTC<br>GCCAGGCCCCGGGCAAAGGCCTGAGTGGGTTGGTCGTATCAAGT<br>CTAAAACTGACGGTGGCACCACGGATTACGCGGCTCCAGTTAAAG<br>GTCGTTTTACCATTTCCCGCGACGATAGCAAAAACACTCTGTATCT<br>GCAGATGAACTCTCTGAAAACTGAAGACACCGCAGTCTACTACTGT<br>ACTACCCCGTGGGAATGGTCTTGGTACGATTATTGGGGCCAGGGCA<br>CGCTGGTTACGGTGTCTAGCGCTAGTACCAAGGGCCCCAGCGTGTT<br>CCCCCTGGCACCCAGCAGCAAGAGCACATCTGGCGGAACAGCCGC<br>TCTGGGCTGTCTGGTGAAAGACTACTTCCCCGAGCCCGTGACCGTG<br>TCTTGGAACTCTGGCGCCCTGACCAGCGGCGTGCACACCTTTCCAG<br>CCGTGCTGCAGAGCAGCGGCCTGTACTCCCTGTCCTCCGTGGTCAC<br>CGTGCCCTCTAGCTCCCTGGGAACACAGACATATATCTGTAATGTC<br>AATCACAAGCCTTCCAACACCAAAGTCGATAAGAAAGTCGAGCCC<br>AAGAGCTGCGACAAAACTCACACATGCCCACCGTGCCCAGCACCT<br>GAAGCTGCAGGGGACCGTCAGTCTTCCTCTTCCCCCCAAAACCCA<br>AGGACACCCTCATGATCTCCCGGACCCCTGAGGTCACATGCGTGGT<br>GGTGGACGTGAGCCACGAAGACCCTGAGGTCAAGTTCAACTGGTA<br>CGTGGACGGCGTGGAGGTGCATAATGCCAAGACAAAGCCGCGGGA<br>GGAGCAGTACAACAGCACGTACCGTGTGGTCAGCGTCCTCACCGTC<br>CTGCACCAGGACTGGCTGAATGGCAAGGAGTACAAGTGCAAGGTC<br>TCCAACAAAGCCCTCGGCGCCCCCATCGAGAAAACCATCTCCAAA<br>GCCAAAGGGCAGCCCCGAGAACCACAGGTGTACACCCTGCCCCCA<br>TGCCGGGATGAGCTGACCAAGAACCAGGTCAGCCTGTGGTGCCTG<br>GTCAAAGGCGGCTATCCCAGCGACATCGCCGTGGAGTGGGAGAGC<br>AATGCCGCAGCCGGAGAACAACTACAAGACCACGCCTCCCGTGCTG<br>GACTCCGACGGCTCCTTCTTCCTCTACAGCAAGCTCACCGTGGACA<br>AGAGCAGGTGGCAGCAGGGGAACGTCTTCTCATGCTCCGTGATGC<br>ATGAGGCTCTGCACAACCACTACACGCAGAAGAGCCTCTCCCTGTC<br>TCCGGGTAAATGA | 66 |
| anti CD3 (CH2527<br>VH3_3-23(12) VL7-<br>46(13)) scFv<br>432.63 non | CAAGTGCAGCTGAAAGAGTCCGGCCCTGGACTGGTGGCCCCTAGC<br>CAGAGACCTGAGGATCACCTGTACCGTGTCCGGCTTCAGCCTGACCA<br>GCTACGGCGTGTCATGGGTGCGCCAGCCTCCAGGCAAGTGTCTGGA<br>ATGGCTGGGCATCATCTGGGGCGACGGCAGCACCAATTACCACAG | 67 |

| | Exemplary sequences | |
|---|---|---|
| cleavable linker CH2527 VH3_23-VH12 CH1 FolR1 16D5 VH CH1 hum Fc knob PG LALA, pETR15603 | CGCCCTGATCAGCAGACTGAGCATCTCCAAGGACAACAGCAAGAG CCAGGTGTTCCTGAAGCTGAACAGCCTGCAGACCGACGACACCGC CACCTACTACTGCGCCAAGGGCATCACCACCGTGGTGGACGACTAC TACGCTATGGACTACTGGGGCCAGGGCACCAGCGTGACAGTGTCT AGCGGAGGCGGAGGATCTGGCGGCGGAGGAAGTGGCGGAGGGGG ATCTGGGGGAGGCGGAAGCGATATCCAGATGACCCAGAGCCCTGC CAGCCTGTCTGCCTCTGTGGGCGAGACAGTGACCATCACATGCCGG GCCAGCGAGAACATCGACAGCTACCTGGCCTGGTATCAGCAGAAG CAGGGCAAGAGCCCCCAGCTGCTGGTGTACGCCGCCACCTTTCTGG CCGACGATGTGCCCAGCAGATTCAGCGGCAGCGGAAGCGGCACAC AGTACAGCCTGAAGATCAACTCCCTGCAGAGCGAGGACGTGGCCC GGTACTACTGCCAGCACTACTACAGCACCCCCTACACCTTCGGCTG CGGCACCAAGCTGGAAATCAAAGGCGGGGGAGGCTCCGGAGGCG GCGGAAGTGGAGGCGGCGGAAGTGGCGGAGGCGGAGGGGGGGA AGTGGGGGCGGAGGCAGTGGGGGGGAGGATCCGAGGTGCAGCT GCTGGAATCTGGCGGCGGACTGGTGCAGCCTGGCGGATCTCTGAG ACTGAGCTGTGCCGCCAGCGGCTTCACCTTCAGCACCTACGCCATG AACTGGGTGCGCCAGGCCCCTGGCAAAGGCCTGGAATGGGTGTCC CGGATCAGAAGCAAGTACAACAACTACGCCACCTACTACGCCGAC AGCGTGAAGGGCCGGTTCACCATCAGCCGGGACGACAGCAAGAAC ACCCTGTACCTGCAGATGAACAGCCTGCGGGCCGAGGACACCGCC GTGTACTATTGTGTGCGGCACGGCAACTTCGGCAACAGCTATGTGT CTTGGTTTGCCTACTGGGGCCAGGGCACCCTCGTGACCGTGTCAAG CGCTAGCACAAAGGGCCCTAGCGTGTTCCCTCTGGCCCCCAGCAGC AAGAGCACAAGCGGCGGAACAGCCGCCCTGGGCTGCCTCGTGAAG GACTACTTCCCCGAGCCCGTGACAGTGTCTTGGAACAGCGGAGCCC TGACAAGCGGCGTGCACACCTTCCCTGCCGTGCTGCAGAGCAGCG GCCTGTACTCCCTGAGCAGCGTGGTCACCGTGCCTAGCAGCAGCCT GGGCACCCAGACCTACATCTGCAACGTGAACCACAAGCCCAGCAA CACCAAAGTGGACAAGAAGGTGGAGCCCAAGAGCTGTGATGGCGG AGGAGGGTCCGGAGGCGGAGGGTCCGAGGTGCAATTGGTTGAATC TGGTGGTGGTCTGGTAAAACCGGGCGGTTCCCTGCGTCTGAGCTGC GCGGCTTCCGGATTCACCTTCTCCAACGCGTGGATGAGCTGGGTTC GCCAGGCCCCGGGCAAAGGCCTCGAGTGGGTTGGTCGTATCAAGT CTAAAACTGACGGTGGCACCACCGGATTACGCGGCTCCAGTTAAAG GTCGTTTTACCATTTCCCGCGACGATAGCAAAAACACTCTGTATCT GCAGATGAACTCTCTGAAAACTGAAGACACCGCAGTCTACTACTGT ACTACCCCGTGGGAATGGTCTTGGTACGATTATTGGGGCCAGGGCA CGCTGGTTACGGTGTCTAGCGCTAGTACCAAGGGCCCCAGCGTGTT CCCCCTGGCACCCAGCAGCAAGAGCACATCTGGCGGAACAGCCGC TCTGGGCTGTCTGGTGAAAGACTACTTCCCCGAGCCCGTGACCGTG TCTTGGAACTCTGGCGCCCTGACCAGCGGCGTGCACACCTTTCCAG CCGTGCTGCAGAGCAGCGGCCTGTACTCCCTGTCCTCCGTGGTCAC CGTGCCCTCTAGCTCCCTGGGAACACAGACATATATCTGTAATGTC AATCACAAGCCTTCCAACACCAAAGTCGATAAGAAAGTCGAGCCC AAGAGCTGCGACAAAACTCACACATGCCCACCGTGCCCAGCACCT GAAGCTGCAGGGGGACCGTCAGTCTTCCTCTTCCCCCCAAAACCCA AGGACACCCTCATGATCTCCCGGACCCCTGAGGTCACATGCGTGGT GGTGGACGTGAGCCACGAAGACCCTGAGGTCAAGTTCAACTGGTA CGTGGACGGCGTGGAGGTGCATAATGCCAAGACAAAGCCGCGGGA GGAGCAGTACAACAGCACGTACCGTGTGGTCAGCGTCCTCACCGTC CTGCACCAGGACTGGCTGAATGGCAAGGAGTACAAGTGCAAGGTC TCCAACAAAGCCCTCGGCGCCCCCATCGAGAAAACcATCTCCAAA GCCAAAGGGCAGCCCCGAGAACCACAGGTGTACACCCTGCCCCCA TGCCGGGATGAGCTGACCAAGAACCAGGTCAGCCTCTTGCTTGCCTG GTCAAAGGCTTCTATCCCAGCGACATCGCCGTGGAGTGGGAGAGC AATGGGCAGCCGGAGAACAACTACAAGACCACGCCTCCCGTGCTG GACTCCGACGGCTCCTTCTTCCTCTACAGCAAGCTCACCGTGGACA AGAGCAGGTGGCAGCAGGGGAACGTCTTGTCATGCTCCGTGATGC ATGAGGCTCTGCACAACCACTACACGCAGAAGAGCCTCTCCCTGTC TCCGGGTAAATGA | |
| Repeat 1 | GGGAATTTCC | 68 |
| Repeat 2 | GGGGACTTTCC | 69 |
| Repeat 3 | GGGACTTTCC | 70 |
| Repeat 4 | GGGACTTCC | 71 |
| Repeat 5 | ATTGTAGCGTA | 72 |
| Response element 1 | GGGAATTT CCGGGGACTT TCCGGGAATTTCCGGGGACT TTCCGGGAATTTCC | 73 |
| Response element 2 | GGGAATTCCGGGAATTTCCGGGAATTTCCGGGAATTTCCGGGAAT TTCCGGGAATTTCC | 74 |

| Exemplary sequences | | |
|---|---|---|
| Response element 3 | GGGACTTCCGGGACTTTCCGGGACTTTCCGGGACTTTCCGGGACTT TCCGGGACTTTCC | 75 |
| Response element 4 | GGGACTTTCCATTGTAGCGTAGGGACTTTCCATTGTAGCGTAGGGC TTTCCATTGTAGCGTAGGGCTTTCC | 76 |
| p95HER2 VH-CH1(EE)-Fc (hole, P329G LALA) | EVQLVESGGGIVQPGGSLKLSCAASGFTFNDFGMSWIRQTPDKRLELV ATINTINGGTTHYPDNVKGRFSISRDNAKKFVYLQMSSLKSDDTAIYYC PREGLDYWGQGTTLTVSSASTKGPSVFPLAPSSKSTSGGTAALGCLVE DYFPEPVTVSWNSGALTSGVHTFPAVLQSSGLYSLSSVVTVPSSSLGT QTYICNVNHKPSNTKVDEKVEPKSCDKTHTCPPCPAPEAAGGPSVFLF PPKPKDTLMISRTPEVTCVVVDVSHEDPEVKFNWYVDGVEVHNAKTK PREEQYNSTYRVVSVLTVLHQDWLNGKEYKCKVSNKALGAPIEKTIS KAKGQPREPQVCTLPPSRDELTKNQVSLSCAVKGFYPSDIAVEWESNG QPENNYKTTPPVLDSDGSFFLVSKLTVDKSRWQQGNVFSCSVMHEAL HNHYTQKLSLSP | 77 |
| p95HER2 VH-CH1(EE)-CD3 VL-CH1-Fc (knob, P329G LALA) | EVQLVESGGGIVQPGGSLKLSCAASGFTFNDFGMSWIRQTPDKRLELV ATINTINGGTTHYPDNVKGRFSISRDNAKKFVYLQMSSLKSDDTAIYYC PREGLDYWGQGTTLTVSSASTKGPSVFPLAPSSKSTSGGTAALGCLVE DYFPEPVTVSWNSGALTSGVHTFPAVLQSSGLYSLSSVVTVPSSSLGT QTYICNVNHKPSNTKVDEKVEPKSCDGGGGSGGGGSQAVVTQEPSLT VSPGGTVTLTCGSSTGAVTTSNYANWVQKPGQAFRGLIGGTNKRAP GTPARFSGSLLGGKAALTLSGAQPEDEAEYYCALWYSNLWVFGGGT KLTVLSSASTKGPSVFPLAPSSKSTSGGTAALGCLVKDYFPEPVTSW SNGALTSGVHTFPAVLQSGLYSLSSVVTPSSSLGTQTYICNVNHKPS NTKVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQV YTLPPCRDELTKNQVSLWCLVKGFYPSDIAVEWESNGQPENNYKTTP PVLDSDGSFFLYSKLTVDKSRWQQGNVFSCSVMHEALHNHYTQKSLS LSP | 78 |
| CD3 VH-CL | EVQLLESGGGLVQPGGSLRLSCAASGFTFSTYAMNWVRQAPGKGLE WVSRIRSKYNNYATYYADSVKGRFTISRDDSKNTLYLQMNSLRAEDT AVYYCVRHGNFGNSYVSWRAYWGQGTLVTVSSASVAAPSVFIFPPSD EQLKSGTASVVCLLNNFYPREAKVQWKVDNALQSGNSQESVTEQDS KDSTYSLSSTLTLSKADYEKHKVYACEVTHQGLSSPVTKSFNRGEC | 79 |
| p95HER2 VL-CL(RK) | DIVLTQSQKFMSTSVGDRVSIICKASQSVGTAVAWYQLKAGQSPKLLI YSASNRFTGVPDRFTGSGSGTDFTLTISNVQSEDLADYFCQQYSTYPL AFGAGTKLELKRTVAAPSVFIFPPSDRKLKSGTASVVCLLNNFYPREA KVQWKVDNALQSGNSQESVTEQDSKDSTYSLSSTLTLSKADYEKHKV YACEVTHQGLSSPVTKSFNRGEC | 80 |

The invention claimed is:

1. An in vitro method for determining the presence of a target antigen in a tumor sample comprising the steps of:
    i) providing a tumor sample;
    ii) providing reporter cells comprising a reporter gene under the control of a signal transducing cell surface receptor, wherein said signal transducing cell surface receptor is human CD3ε;
    iii) adding to the tumor sample a bispecific antibody comprising:
        a) a first antigen binding moiety capable of specific binding to said target antigen; and
        b) a second antigen binding moiety capable of specific binding to the signal transducing cell surface receptor;
        c) a masking moiety covalently attached to the second antigen binding moiety through a protease-cleavable linker, wherein the masking moiety is capable of specific binding to the idiotype of the second antigen binding moiety thereby reversibly concealing the second antigen binding moiety,
    wherein the masking moiety is an anti-idiotypic scFv comprising an HCDR1 comprising the amino acid sequence of SEQ ID NO: 20, an HCDR2 comprising the amino acid sequence of SEQ ID NO: 21, an HCDR3 comprising the amino acid sequence of SEQ ID NO: 22, an LCDR1 comprising the amino acid sequence of SEQ ID NO: 23, an LCDR2 comprising the amino acid sequence of SEQ ID NO: 24, and an LCDR3 comprising the amino acid sequence of SEQ ID NO: 25;
    iv) adding the reporter cells to the tumor sample; and
    v) determining the presence of the target antigen by determining the expression of the reporter gene.

2. The method according to claim 1, wherein the expression of the reporter gene is indicative for binding of the first antigen binding moiety to the target antigen.

3. The method according to claim 1 wherein the expression of the reporter gene is indicative for protease expression in the tumor sample.

4. The method according to claim 3, wherein protease expression is indicative for a malignant tumor.

5. The method according to claim 1, wherein the tumor sample is a tumor tissue sample.

6. The method according to claim 5, wherein the tumor tissue sample comprises a patient biopsy.

7. The method according to claim 1, wherein the reporter cells comprise the DNA sequence coding for the reporter gene under the control of the response element, and the DNA sequence coding for the signal transducing cell surface receptor.

8. The method according to claim 1, wherein the target antigen is a cell surface receptor.

9. The method of claim 1, wherein said target antigen is CEA, Her2, TYRP, EGFR, MCSP, STEAP1, or WT1.

10. The method according to claim 1, wherein the target antigen is Folate Receptor 1 (FolR1).

11. The method of claim 10, wherein said first antigen binding moiety comprises an HCDR1 comprising the amino acid sequence of SEQ ID NO: 14, an HCDR2 comprising the amino acid sequence of SEQ ID NO: 15, an HCDR3 comprising the amino acid sequence of SEQ ID NO: 16, an LCDR1 comprising the amino acid sequence of SEQ ID NO: 17, an LCDR2 comprising the amino acid sequence of SEQ ID NO: 18, and an LCDR3 comprising the amino acid sequence of SEQ ID NO: 19.

12. The method according to claim 1, wherein the target antigen is a peptide bound to a molecule of the human major histocompatibility complex (MHC).

13. The method of claim 1, wherein said second antigen binding moiety comprises heavy chain complementarity determining region 1 (HCDR1) comprising the amino acid sequence of SEQ ID NO: 11, an HCDR2 comprising the amino acid sequence of SEQ ID NO: 12, an HCDR3 comprising the amino acid sequence of SEQ ID NO: 13, a light chain complementarity determining region 1 (LCDR1) comprising the amino acid sequence of SEQ ID NO: 17, an LCDR2 comprising the amino acid sequence of SEQ ID NO: 18, and an LCDR3 comprising the amino acid sequence of SEQ ID NO:19.

14. The method of claim 1, wherein said second antigen binding moiety comprises heavy chain variable region comprising the amino acid sequence of SEQ ID NO: 26 and a light chain variable region comprising the amino acid sequence of SEQ ID NO: 28.

15. The method of claim 1, wherein
 a. said first antigen binding moiety comprises an HCDR1 comprising the amino acid sequence of SEQ ID NO: 14, an HCDR2 comprising the amino acid sequence of SEQ ID NO: 15, an HCDR3 comprising the amino acid sequence of SEQ ID NO: 16, an LCDR1 comprising the amino acid sequence of SEQ ID NO: 17, an LCDR2 comprising the amino acid sequence of SEQ ID NO: 18, and an LCDR3 comprising the amino acid sequence of SEQ ID NO: 19;
 b. said second antigen binding moiety comprises heavy chain complementarity determining region 1 (HCDR1) comprising the amino acid sequence of SEQ ID NO: 11, an HCDR2 comprising the amino acid sequence of SEQ ID NO: 12, an HCDR3 comprising the amino acid sequence of SEQ ID NO: 13, a light chain complementarity determining region 1 (LCDR1) comprising the amino acid sequence of SEQ ID NO: 17, an LCDR2 comprising the amino acid sequence of SEQ ID NO: 18, and an LCDR3 comprising the amino acid sequence of SEQ ID NO: 19; and
 c. said anti-idiotypic scFv comprises an HCDR1 comprising the amino acid sequence of SEQ ID NO: 20, an HCDR2 comprising the amino acid sequence of SEQ ID NO: 21, an HCDR3 comprising the amino acid sequence of SEQ ID NO: 22, an LCDR1 comprising the amino acid sequence of SEQ ID NO: 23, an LCDR2 comprising the amino acid sequence of SEQ ID NO: 24, and an LCDR3 comprising the amino acid sequence of SEQ ID NO: 25.

16. The method according to claim 1, wherein the first and the second antigen binding moieties are conventional Fab molecules comprising a common light chain.

17. The method of claim 1, wherein
 a. said first antigen binding moiety is a Fab molecule capable of specific binding to FolR1 comprising heavy chain variable region comprising the amino acid sequence of SEQ ID NO: 27 and a light chain variable region comprising the amino acid sequence of SEQ ID NO: 28; and
 b. said second antigen binding moiety is a Fab molecule capable of specific binding to CD3 comprising a heavy chain variable region comprising the amino acid sequence of SEQ ID NO: 26 and a light chain variable region comprising the amino acid sequence of SEQ ID NO: 28; and
 c. said anti-idiotypic scFv comprises an HCDR1 comprising the amino acid sequence of SEQ ID NO: 20, an HCDR2 comprising the amino acid sequence of SEQ ID NO: 21, an HCDR3 comprising the amino acid sequence of SEQ ID NO: 22, an LCDR1 comprising the amino acid sequence of SEQ ID NO: 23, an LCDR2 comprising the amino acid sequence of SEQ ID NO: 24, and an LCDR3 comprising the amino acid sequence of SEQ ID NO: 25.

\* \* \* \* \*

SEQUENCE LISTING

```
<160> NUMBER OF SEQ ID NOS: 80

<210> SEQ ID NO 1
<211> LENGTH: 215
<212> TYPE: PRT
<213> ORGANISM: Artificial sequence
<220> FEATURE:
<223> OTHER INFORMATION: LC Common light chain pETR 13197

<400> SEQUENCE: 1

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80
```

```
Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 2
<211> LENGTH: 109
<212> TYPE: PRT
<213> ORGANISM: Artificial sequence
<220> FEATURE:
<223> OTHER INFORMATION: LC Common light chain pETR13197 V region

<400> SEQUENCE: 2

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 3
<211> LENGTH: 450
<212> TYPE: PRT
<213> ORGANISM: Artificial sequence
<220> FEATURE:
<223> OTHER INFORMATION: anti FolR1 16D5 VH CH1 Fc hole HRYF, pCON983

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45
```

```
Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
            435                 440                 445

Gly Lys
450
```

-continued

```
<210> SEQ ID NO 4
<211> LENGTH: 689
<212> TYPE: PRT
<213> ORGANISM: Artificial sequence
<220> FEATURE:
<223> OTHER INFORMATION: CD3 CH2527-VH3_23-12 CH1 (G4S)2 FolR1 16D5 VH
      CH1 Fc knob P329G LALA, pETR13932

<400> SEQUENCE: 4
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Gly Gly Gly Ser Gly Gly Gly Gly Ser Glu
225                 230                 235                 240

Val Gln Leu Val Glu Ser Gly Gly Gly Leu Val Lys Pro Gly Gly Ser
                245                 250                 255

Leu Arg Leu Ser Cys Ala Ala Ser Gly Phe Thr Phe Ser Asn Ala Trp
            260                 265                 270

Met Ser Trp Val Arg Gln Ala Pro Gly Lys Gly Leu Glu Trp Val Gly
        275                 280                 285

Arg Ile Lys Ser Lys Thr Asp Gly Gly Thr Thr Asp Tyr Ala Ala Pro
    290                 295                 300

Val Lys Gly Arg Phe Thr Ile Ser Arg Asp Asp Ser Lys Asn Thr Leu
305                 310                 315                 320

Tyr Leu Gln Met Asn Ser Leu Lys Thr Glu Asp Thr Ala Val Tyr Tyr
                325                 330                 335

Cys Thr Thr Pro Trp Glu Trp Ser Trp Tyr Asp Tyr Trp Gly Gln Gly
            340                 345                 350

Thr Leu Val Thr Val Ser Ser Ala Ser Thr Lys Gly Pro Ser Val Phe
        355                 360                 365

```
Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
            405                 410                 415

Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
        435                 440                 445

Ser Asn Thr Lys Val Asp Lys Lys Val Glu Pro Lys Ser Cys Asp Lys
    450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
            485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
            565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
        595                 600                 605

Cys Leu Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
            645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 5
<211> LENGTH: 215
<212> TYPE: PRT
<213> ORGANISM: Artificial sequence
<220> FEATURE:
<223> OTHER INFORMATION: LC Common light chain pETR13197

<400> SEQUENCE: 5

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30
```

-continued

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 6
<211> LENGTH: 971
<212> TYPE: PRT
<213> ORGANISM: Artificial sequence
<220> FEATURE:
<223> OTHER INFORMATION: anti CD3 (CH2527 VH_3-23(12) VL7-46(13)) scFv
      4.32.63 MMP9 Matriptase MK062 CH2527 CH3_23-VH12 CH1 FolR1 16D5 VH
      CH1 hum Fc knob PG LALA, pETR16546

<400> SEQUENCE: 6

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Gly Gly Gly Gly Ser Asp Ile
    130                 135                 140

Gln Met Thr Gln Ser Pro Ala Ser Leu Ser Ala Ser Val Gly Glu Thr
145                 150                 155                 160

-continued

Val Thr Ile Thr Cys Arg Ala Ser Glu Asn Ile Asp Ser Tyr Leu Ala
              165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Val His
                245                 250                 255

Met Pro Leu Gly Phe Leu Gly Pro Arg Gln Ala Arg Val Val Asn Gly
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
            325                 330                 335

Tyr Asn Asn Tyr Ala Thr Tyr Tyr Ala Asp Ser Val Lys Gly Arg Phe
            340                 345                 350

Thr Ile Ser Arg Asp Asp Ser Lys Asn Thr Leu Tyr Leu Gln Met Asn
        355                 360                 365

Ser Leu Arg Ala Glu Asp Thr Ala Val Tyr Tyr Cys Val Arg His Gly
    370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
            405                 410                 415

Pro Leu Ala Pro Ser Ser Lys Ser Thr Ser Gly Gly Thr Ala Ala Leu
            420                 425                 430

Gly Cys Leu Val Lys Asp Tyr Phe Pro Glu Pro Val Thr Val Ser Trp
        435                 440                 445

Asn Ser Gly Ala Leu Thr Ser Gly Val His Thr Phe Pro Ala Val Leu
    450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
            485                 490                 495

Ser Asn Thr Lys Val Asp Lys Lys Val Glu Pro Lys Ser Cys Asp Gly
            500                 505                 510

Gly Gly Gly Ser Gly Gly Gly Gly Ser Glu Val Gln Leu Val Glu Ser
        515                 520                 525

Gly Gly Gly Leu Val Lys Pro Gly Gly Ser Leu Arg Leu Ser Cys Ala
    530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
            565                 570                 575

Asp Gly Gly Thr Thr Asp Tyr Ala Ala Pro Val Lys Gly Arg Phe Thr
            580                 585                 590

Ile Ser Arg Asp Asp Ser Lys Asn Thr Leu Tyr Leu Gln Met Asn Ser
        595                 600                 605

Leu Lys Thr Glu Asp Thr Ala Val Tyr Tyr Cys Thr Thr Pro Trp Glu
    610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
                645                 650                 655

Lys Ser Thr Ser Gly Gly Thr Ala Ala Leu Gly Cys Leu Val Lys Asp
            660                 665                 670

Tyr Phe Pro Glu Pro Val Thr Val Ser Trp Asn Ser Gly Ala Leu Thr
        675                 680                 685

Ser Gly Val His Thr Phe Pro Ala Val Leu Gln Ser Ser Gly Leu Tyr
    690                 695                 700

Ser Leu Ser Ser Val Val Thr Val Pro Ser Ser Ser Leu Gly Thr Gln
705                 710                 715                 720

Thr Tyr Ile Cys Asn Val Asn His Lys Pro Ser Asn Thr Lys Val Asp
                725                 730                 735

Lys Lys Val Glu Pro Lys Ser Cys Asp Lys Thr His Thr Cys Pro Pro
            740                 745                 750

Cys Pro Ala Pro Glu Ala Ala Gly Gly Pro Ser Val Phe Leu Phe Pro
        755                 760                 765

Pro Lys Pro Lys Asp Thr Leu Met Ile Ser Arg Thr Pro Glu Val Thr
770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                805                 810                 815

Glu Glu Gln Tyr Asn Ser Thr Tyr Arg Val Val Ser Val Leu Thr Val
            820                 825                 830

Leu His Gln Asp Trp Leu Asn Gly Lys Glu Tyr Lys Cys Lys Val Ser
        835                 840                 845

Asn Lys Ala Leu Gly Ala Pro Ile Glu Lys Thr Ile Ser Lys Ala Lys
850                 855                 860

Gly Gln Pro Arg Glu Pro Gln Val Tyr Thr Leu Pro Pro Cys Arg Asp
865                 870                 875                 880

Glu Leu Thr Lys Asn Gln Val Ser Leu Trp Cys Leu Val Lys Gly Phe
                885                 890                 895

Tyr Pro Ser Asp Ile Ala Val Glu Trp Glu Ser Asn Gly Gln Pro Glu
            900                 905                 910

Asn Asn Tyr Lys Thr Thr Pro Pro Val Leu Asp Ser Asp Gly Ser Phe
        915                 920                 925

Phe Leu Tyr Ser Lys Leu Thr Val Asp Lys Ser Arg Trp Gln Gln Gly
930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
                965                 970

<210> SEQ ID NO 7
<211> LENGTH: 450
<212> TYPE: PRT

<213> ORGANISM: Artificial sequence
<220> FEATURE:
<223> OTHER INFORMATION: FolR1 16D5 VH CH1 Fc hole P329G LALA HRYF,
    pETR15214

<400> SEQUENCE: 7

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 8
<211> LENGTH: 971
<212> TYPE: PRT
<213> ORGANISM: Artificial sequence
<220> FEATURE:
<223> OTHER INFORMATION: anti CD3 (CH2527 VH_3-23(12) VL7-46(13)) scFv
      4.32.63 Matriptase MK062 CH2527 VH3_23-VH12 CH1 FolR1 16D5 VH CH1
      hum Fc knob PG LALA, pETR15599

<400> SEQUENCE: 8

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Gly Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Gly Ser Gly Gly
                245                 250                 255

Gly Gly Ser Arg Gln Ala Arg Val Val Asn Gly Gly Gly Gly Ser
            260                 265                 270
```

```
Gly Gly Gly Gly Ser Gly Gly Gly Ser Glu Val Gln Leu Leu Glu
            275                 280                 285

Ser Gly Gly Gly Leu Val Gln Pro Gly Gly Ser Leu Arg Leu Ser Cys
290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Ala Asp Ser Val Lys Gly Arg Phe
                340                 345                 350

Thr Ile Ser Arg Asp Asp Ser Lys Asn Thr Leu Tyr Leu Gln Met Asn
            355                 360                 365

Ser Leu Arg Ala Glu Asp Thr Ala Val Tyr Tyr Cys Val Arg His Gly
    370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
                405                 410                 415

Pro Leu Ala Pro Ser Ser Lys Ser Thr Ser Gly Gly Thr Ala Ala Leu
            420                 425                 430

Gly Cys Leu Val Lys Asp Tyr Phe Pro Glu Pro Val Thr Val Ser Trp
    435                 440                 445

Asn Ser Gly Ala Leu Thr Ser Gly Val His Thr Phe Pro Ala Val Leu
450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
                485                 490                 495

Ser Asn Thr Lys Val Asp Lys Lys Val Glu Pro Lys Ser Cys Asp Gly
            500                 505                 510

Gly Gly Gly Ser Gly Gly Gly Ser Glu Val Gln Leu Val Glu Ser
    515                 520                 525

Gly Gly Gly Leu Val Lys Pro Gly Gly Ser Leu Arg Leu Ser Cys Ala
    530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
                565                 570                 575

Asp Gly Gly Thr Thr Asp Tyr Ala Ala Pro Val Lys Gly Arg Phe Thr
                580                 585                 590

Ile Ser Arg Asp Asp Ser Lys Asn Thr Leu Tyr Leu Gln Met Asn Ser
            595                 600                 605

Leu Lys Thr Glu Asp Thr Ala Val Tyr Tyr Cys Thr Thr Pro Trp Glu
    610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
                645                 650                 655

Lys Ser Thr Ser Gly Gly Thr Ala Ala Leu Gly Cys Leu Val Lys Asp
            660                 665                 670

Tyr Phe Pro Glu Pro Val Thr Val Ser Trp Asn Ser Gly Ala Leu Thr
    675                 680                 685
```

-continued

```
Ser Gly Val His Thr Phe Pro Ala Val Leu Gln Ser Gly Leu Tyr
    690                 695                 700
Ser Leu Ser Ser Val Val Thr Val Pro Ser Ser Ser Leu Gly Thr Gln
705                 710                 715                 720
Thr Tyr Ile Cys Asn Val Asn His Lys Pro Ser Asn Thr Lys Val Asp
            725                 730                 735
Lys Lys Val Glu Pro Lys Ser Cys Asp Lys Thr His Thr Cys Pro Pro
        740                 745                 750
Cys Pro Ala Pro Glu Ala Ala Gly Gly Pro Ser Val Phe Leu Phe Pro
    755                 760                 765
Pro Lys Pro Lys Asp Thr Leu Met Ile Ser Arg Thr Pro Glu Val Thr
770                 775                 780
Cys Val Val Val Asp Val Ser His Glu Asp Pro Glu Val Lys Phe Asn
785                 790                 795                 800
Trp Tyr Val Asp Gly Val Glu Val His Asn Ala Lys Thr Lys Pro Arg
            805                 810                 815
Glu Glu Gln Tyr Asn Ser Thr Tyr Arg Val Val Ser Val Leu Thr Val
        820                 825                 830
Leu His Gln Asp Trp Leu Asn Gly Lys Glu Tyr Lys Cys Lys Val Ser
    835                 840                 845
Asn Lys Ala Leu Gly Ala Pro Ile Glu Lys Thr Ile Ser Lys Ala Lys
850                 855                 860
Gly Gln Pro Arg Glu Pro Gln Val Tyr Thr Leu Pro Pro Cys Arg Asp
865                 870                 875                 880
Glu Leu Thr Lys Asn Gln Val Ser Leu Trp Cys Leu Val Lys Gly Phe
            885                 890                 895
Tyr Pro Ser Asp Ile Ala Val Glu Trp Glu Ser Asn Gly Gln Pro Glu
        900                 905                 910
Asn Asn Tyr Lys Thr Thr Pro Pro Val Leu Asp Ser Asp Gly Ser Phe
    915                 920                 925
Phe Leu Tyr Ser Lys Leu Thr Val Asp Lys Ser Arg Trp Gln Gln Gly
930                 935                 940
Asn Val Phe Ser Cys Ser Val Met His Glu Ala Leu His Asn His Tyr
945                 950                 955                 960
Thr Gln Lys Ser Leu Ser Leu Ser Pro Gly Lys
            965                 970

<210> SEQ ID NO 9
<211> LENGTH: 971
<212> TYPE: PRT
<213> ORGANISM: Artificial sequence
<220> FEATURE:
<223> OTHER INFORMATION: anti CD3 (CH2527 VH_3-23(12) VL7-46(13)) scFv
      4.32.63 non cleavable linker CH2527 VH3_23-VH12 CH1 FolR1 16D5 VH
      CH1 hum Fc knob PG LALA, pETR15603

<400> SEQUENCE: 9

Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Thr Ser Tyr
            20                  25                  30
Gly Val Ser Trp Val Arg Gln Pro Pro Gly Lys Cys Leu Glu Trp Leu
        35                  40                  45
Gly Ile Ile Trp Gly Asp Gly Ser Thr Asn Tyr His Ser Ala Leu Ile
    50                  55                  60
```

```
Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
                180                 185                 190

Ala Thr Phe Leu Ala Asp Asp Val Pro Ser Arg Phe Ser Gly Ser Gly
            195                 200                 205

Ser Gly Thr Gln Tyr Ser Leu Lys Ile Asn Ser Leu Gln Ser Glu Asp
        210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Gly Ser Gly Gly
                245                 250                 255

Gly Gly Ser Gly Gly Gly Gly Ser Gly Gly Gly Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Tyr Ala Asp Ser Val Lys Gly Arg Phe
                340                 345                 350

Thr Ile Ser Arg Asp Asp Ser Lys Asn Thr Leu Tyr Leu Gln Met Asn
            355                 360                 365

Ser Leu Arg Ala Glu Asp Thr Ala Val Tyr Tyr Cys Val Arg His Gly
        370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
                405                 410                 415

Pro Leu Ala Pro Ser Ser Lys Ser Thr Ser Gly Gly Thr Ala Ala Leu
                420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
        450                 455                 460

Gln Ser Ser Gly Leu Tyr Ser Leu Ser Ser Val Val Thr Val Pro Ser
465                 470                 475                 480
```

-continued

Ser Ser Leu Gly Thr Gln Thr Tyr Ile Cys Asn Val Asn His Lys Pro
            485                 490                 495

Ser Asn Thr Lys Val Asp Lys Val Glu Pro Lys Ser Cys Asp Gly
        500                 505                 510

Gly Gly Gly Ser Gly Gly Gly Ser Glu Val Gln Leu Val Glu Ser
        515                 520                 525

Gly Gly Gly Leu Val Lys Pro Gly Gly Ser Leu Arg Leu Ser Cys Ala
        530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
                565                 570                 575

Asp Gly Gly Thr Thr Asp Tyr Ala Ala Pro Val Lys Gly Arg Phe Thr
                580                 585                 590

Ile Ser Arg Asp Asp Ser Lys Asn Thr Leu Tyr Leu Gln Met Asn Ser
                595                 600                 605

Leu Lys Thr Glu Asp Thr Ala Val Tyr Tyr Cys Thr Thr Pro Trp Glu
        610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
                645                 650                 655

Lys Ser Thr Ser Gly Gly Thr Ala Ala Leu Gly Cys Leu Val Lys Asp
                660                 665                 670

Tyr Phe Pro Glu Pro Val Thr Val Ser Trp Asn Ser Gly Ala Leu Thr
        675                 680                 685

Ser Gly Val His Thr Phe Pro Ala Val Leu Gln Ser Ser Gly Leu Tyr
        690                 695                 700

Ser Leu Ser Ser Val Val Thr Val Pro Ser Ser Ser Leu Gly Thr Gln
705                 710                 715                 720

Thr Tyr Ile Cys Asn Val Asn His Lys Pro Ser Asn Thr Lys Val Asp
                725                 730                 735

Lys Lys Val Glu Pro Lys Ser Cys Asp Lys Thr His Thr Cys Pro Pro
            740                 745                 750

Cys Pro Ala Pro Glu Ala Ala Gly Gly Pro Ser Val Phe Leu Phe Pro
        755                 760                 765

Pro Lys Pro Lys Asp Thr Leu Met Ile Ser Arg Thr Pro Glu Val Thr
        770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                805                 810                 815

Glu Glu Gln Tyr Asn Ser Thr Tyr Arg Val Val Ser Val Leu Thr Val
                820                 825                 830

Leu His Gln Asp Trp Leu Asn Gly Lys Glu Tyr Lys Cys Lys Val Ser
        835                 840                 845

Asn Lys Ala Leu Gly Ala Pro Ile Glu Lys Thr Ile Ser Lys Ala Lys
        850                 855                 860

Gly Gln Pro Arg Glu Pro Gln Val Tyr Thr Leu Pro Pro Cys Arg Asp
865                 870                 875                 880

Glu Leu Thr Lys Asn Gln Val Ser Leu Trp Cys Leu Val Lys Gly Phe
                885                 890                 895

Tyr Pro Ser Asp Ile Ala Val Glu Trp Glu Ser Asn Gly Gln Pro Glu
                900                 905                 910

Asn Asn Tyr Lys Thr Thr Pro Pro Val Leu Asp Ser Asp Gly Ser Phe
            915                 920                 925

Phe Leu Tyr Ser Lys Leu Thr Val Asp Lys Ser Arg Trp Gln Gln Gly
930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
            965                 970

<210> SEQ ID NO 10
<211> LENGTH: 971
<212> TYPE: PRT
<213> ORGANISM: Artificial sequence
<220> FEATURE:
<223> OTHER INFORMATION: anti CD3 (CH2527 VH_3-23(12) VL7-46(13)) scFv
      4.32.63 Cathepsin S/B site CH2527 VH3_23-VH12 CH1 FolR1 16D5 VH
      CH1 hum Fc knob PG LALA, pETR16550

<400> SEQUENCE: 10

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Gly Gly Gly Gly Ser Phe Val Gly Gly Thr Gly Gly
            260                 265                 270

-continued

Gly Ser Gly Gly Gly Ser Gly Gly Ser Glu Val Gln Leu Leu Glu
275 280 285

Ser Gly Gly Gly Leu Val Gln Pro Gly Gly Ser Leu Arg Leu Ser Cys
290 295 300

Ala Ala Ser Gly Phe Thr Phe Ser Thr Tyr Ala Met Asn Trp Val Arg
305 310 315 320

Gln Ala Pro Gly Lys Gly Leu Glu Trp Val Ser Arg Ile Arg Ser Lys
325 330 335

Tyr Asn Asn Tyr Ala Thr Tyr Tyr Ala Asp Ser Val Lys Gly Arg Phe
340 345 350

Thr Ile Ser Arg Asp Asp Ser Lys Asn Thr Leu Tyr Leu Gln Met Asn
355 360 365

Ser Leu Arg Ala Glu Asp Thr Ala Val Tyr Tyr Cys Val Arg His Gly
370 375 380

Asn Phe Gly Asn Ser Tyr Val Ser Trp Phe Ala Tyr Trp Gly Gln Gly
385 390 395 400

Thr Leu Val Thr Val Ser Ser Ala Ser Thr Lys Gly Pro Ser Val Phe
405 410 415

Pro Leu Ala Pro Ser Ser Lys Ser Thr Ser Gly Gly Thr Ala Ala Leu
420 425 430

Gly Cys Leu Val Lys Asp Tyr Phe Pro Glu Pro Val Thr Val Ser Trp
435 440 445

Asn Ser Gly Ala Leu Thr Ser Gly Val His Thr Phe Pro Ala Val Leu
450 455 460

Gln Ser Ser Gly Leu Tyr Ser Leu Ser Ser Val Val Thr Val Pro Ser
465 470 475 480

Ser Ser Leu Gly Thr Gln Thr Tyr Ile Cys Asn Val Asn His Lys Pro
485 490 495

Ser Asn Thr Lys Val Asp Lys Lys Val Glu Pro Lys Ser Cys Asp Gly
500 505 510

Gly Gly Gly Ser Gly Gly Gly Ser Glu Val Gln Leu Val Glu Ser
515 520 525

Gly Gly Gly Leu Val Lys Pro Gly Gly Ser Leu Arg Leu Ser Cys Ala
530 535 540

Ala Ser Gly Phe Thr Phe Ser Asn Ala Trp Met Ser Trp Val Arg Gln
545 550 555 560

Ala Pro Gly Lys Gly Leu Glu Trp Val Gly Arg Ile Lys Ser Lys Thr
565 570 575

Asp Gly Gly Thr Thr Asp Tyr Ala Ala Pro Val Lys Gly Arg Phe Thr
580 585 590

Ile Ser Arg Asp Asp Ser Lys Asn Thr Leu Tyr Leu Gln Met Asn Ser
595 600 605

Leu Lys Thr Glu Asp Thr Ala Val Tyr Tyr Cys Thr Thr Pro Trp Glu
610 615 620

Trp Ser Trp Tyr Asp Tyr Trp Gly Gln Gly Thr Leu Val Thr Val Ser
625 630 635 640

Ser Ala Ser Thr Lys Gly Pro Ser Val Phe Pro Leu Ala Pro Ser Ser
645 650 655

Lys Ser Thr Ser Gly Gly Thr Ala Ala Leu Gly Cys Leu Val Lys Asp
660 665 670

Tyr Phe Pro Glu Pro Val Thr Val Ser Trp Asn Ser Gly Ala Leu Thr
675 680 685

-continued

```
Ser Gly Val His Thr Phe Pro Ala Val Leu Gln Ser Gly Leu Tyr
        690                 695                 700

Ser Leu Ser Ser Val Val Thr Val Pro Ser Ser Ser Leu Gly Thr Gln
705                 710                 715                 720

Thr Tyr Ile Cys Asn Val Asn His Lys Pro Ser Asn Thr Lys Val Asp
            725                 730                 735

Lys Lys Val Glu Pro Lys Ser Cys Asp Lys Thr His Thr Cys Pro Pro
                740                 745                 750

Cys Pro Ala Pro Glu Ala Ala Gly Gly Pro Ser Val Phe Leu Phe Pro
            755                 760                 765

Pro Lys Pro Lys Asp Thr Leu Met Ile Ser Arg Thr Pro Glu Val Thr
        770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                805                 810                 815

Glu Glu Gln Tyr Asn Ser Thr Tyr Arg Val Val Ser Val Leu Thr Val
                820                 825                 830

Leu His Gln Asp Trp Leu Asn Gly Lys Glu Tyr Lys Cys Lys Val Ser
            835                 840                 845

Asn Lys Ala Leu Gly Ala Pro Ile Glu Lys Thr Ile Ser Lys Ala Lys
850                 855                 860

Gly Gln Pro Arg Glu Pro Gln Val Tyr Thr Leu Pro Pro Cys Arg Asp
865                 870                 875                 880

Glu Leu Thr Lys Asn Gln Val Ser Leu Trp Cys Leu Val Lys Gly Phe
                885                 890                 895

Tyr Pro Ser Asp Ile Ala Val Glu Trp Glu Ser Asn Gly Gln Pro Glu
            900                 905                 910

Asn Asn Tyr Lys Thr Thr Pro Pro Val Leu Asp Ser Asp Gly Ser Phe
        915                 920                 925

Phe Leu Tyr Ser Lys Leu Thr Val Asp Lys Ser Arg Trp Gln Gln Gly
    930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
                965                 970

<210> SEQ ID NO 11
<211> LENGTH: 5
<212> TYPE: PRT
<213> ORGANISM: Artificial sequence
<220> FEATURE:
<223> OTHER INFORMATION: CD3 HCDR1

<400> SEQUENCE: 11

Thr Tyr Ala Met Asn
1               5

<210> SEQ ID NO 12
<211> LENGTH: 19
<212> TYPE: PRT
<213> ORGANISM: Artificial sequence
<220> FEATURE:
<223> OTHER INFORMATION: CD3 HCDR2
```

-continued

```
<400> SEQUENCE: 12

Arg Ile Arg Ser Lys Tyr Asn Asn Tyr Ala Thr Tyr Tyr Ala Asp Ser
1               5                   10                  15

Val Lys Gly

<210> SEQ ID NO 13
<211> LENGTH: 14
<212> TYPE: PRT
<213> ORGANISM: Artificial sequence
<220> FEATURE:
<223> OTHER INFORMATION: CD3 HCDR3

<400> SEQUENCE: 13

His Gly Asn Phe Gly Asn Ser Tyr Val Ser Trp Phe Ala Tyr
1               5                   10

<210> SEQ ID NO 14
<211> LENGTH: 5
<212> TYPE: PRT
<213> ORGANISM: Artificial sequence
<220> FEATURE:
<223> OTHER INFORMATION: FolR1 HCDR1

<400> SEQUENCE: 14

Asn Ala Trp Met Ser
1               5

<210> SEQ ID NO 15
<211> LENGTH: 19
<212> TYPE: PRT
<213> ORGANISM: Artificial sequence
<220> FEATURE:
<223> OTHER INFORMATION: FolR1 HCDR2

<400> SEQUENCE: 15

Arg Ile Lys Ser Lys Thr Asp Gly Gly Thr Thr Asp Tyr Ala Ala Pro
1               5                   10                  15

Val Lys Gly

<210> SEQ ID NO 16
<211> LENGTH: 9
<212> TYPE: PRT
<213> ORGANISM: Artificial sequence
<220> FEATURE:
<223> OTHER INFORMATION: FolR1 HCDR3

<400> SEQUENCE: 16

Pro Trp Glu Trp Ser Trp Tyr Asp Tyr
1               5

<210> SEQ ID NO 17
<211> LENGTH: 14
<212> TYPE: PRT
<213> ORGANISM: Artificial sequence
<220> FEATURE:
<223> OTHER INFORMATION: CLC LCDR1

<400> SEQUENCE: 17

Gly Ser Ser Thr Gly Ala Val Thr Thr Ser Asn Tyr Ala Asn
1               5                   10

<210> SEQ ID NO 18
<211> LENGTH: 7
<212> TYPE: PRT
```

```
<213> ORGANISM: Artificial sequence
<220> FEATURE:
<223> OTHER INFORMATION: CLC LCDR2

<400> SEQUENCE: 18

Gly Thr Asn Lys Arg Ala Pro
1               5

<210> SEQ ID NO 19
<211> LENGTH: 9
<212> TYPE: PRT
<213> ORGANISM: Artificial sequence
<220> FEATURE:
<223> OTHER INFORMATION: CLC LCDR3

<400> SEQUENCE: 19

Ala Leu Trp Tyr Ser Asn Leu Trp Val
1               5

<210> SEQ ID NO 20
<211> LENGTH: 5
<212> TYPE: PRT
<213> ORGANISM: Artificial sequence
<220> FEATURE:
<223> OTHER INFORMATION: Anti ID 4.32.63 CDR H1 Kabat

<400> SEQUENCE: 20

Ser Tyr Gly Val Ser
1               5

<210> SEQ ID NO 21
<211> LENGTH: 16
<212> TYPE: PRT
<213> ORGANISM: Artificial sequence
<220> FEATURE:
<223> OTHER INFORMATION: Anti ID 4.32.63 CDR H2 Kabat

<400> SEQUENCE: 21

Ile Ile Trp Gly Asp Gly Ser Thr Asn Tyr His Ser Ala Leu Ile Ser
1               5                   10                  15

<210> SEQ ID NO 22
<211> LENGTH: 14
<212> TYPE: PRT
<213> ORGANISM: Artificial sequence
<220> FEATURE:
<223> OTHER INFORMATION: Anti ID 4.32.63 CDR H3 Kabat

<400> SEQUENCE: 22

Gly Ile Thr Thr Val Val Asp Asp Tyr Tyr Ala Met Asp Tyr
1               5                   10

<210> SEQ ID NO 23
<211> LENGTH: 11
<212> TYPE: PRT
<213> ORGANISM: Artificial sequence
<220> FEATURE:
<223> OTHER INFORMATION: Anti ID 4.32.63 CDR L1 Kabat

<400> SEQUENCE: 23

Arg Ala Ser Glu Asn Ile Asp Ser Tyr Leu Ala
1               5                   10

<210> SEQ ID NO 24
<211> LENGTH: 7
<212> TYPE: PRT
<213> ORGANISM: Artificial sequence
```

```
<220> FEATURE:
<223> OTHER INFORMATION: Anti ID 4.32.63 CDR L2 Kabat

<400> SEQUENCE: 24

Ala Ala Thr Phe Leu Ala Asp
1               5

<210> SEQ ID NO 25
<211> LENGTH: 9
<212> TYPE: PRT
<213> ORGANISM: Artificial sequence
<220> FEATURE:
<223> OTHER INFORMATION: Anti ID 4.32.63 CDR L3 Kabat

<400> SEQUENCE: 25

Gln His Tyr Tyr Ser Thr Pro Tyr Thr
1               5

<210> SEQ ID NO 26
<211> LENGTH: 125
<212> TYPE: PRT
<213> ORGANISM: Artificial sequence
<220> FEATURE:
<223> OTHER INFORMATION: Anti-CD3 variable heavy chain (VH)

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 27
<211> LENGTH: 120
<212> TYPE: PRT
<213> ORGANISM: Artificial sequence
<220> FEATURE:
<223> OTHER INFORMATION: Anti-FolR1 16D5 variable heavy chain (VH)

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

```
Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
                100                 105                 110

Gly Thr Leu Val Thr Val Ser Ser
        115                 120

<210> SEQ ID NO 28
<211> LENGTH: 109
<212> TYPE: PRT
<213> ORGANISM: Artificial sequence
<220> FEATURE:
<223> OTHER INFORMATION: LC Common variable light chain (VL)

<400> SEQUENCE: 28

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105

<210> SEQ ID NO 29
<211> LENGTH: 249
<212> TYPE: PRT
<213> ORGANISM: Artificial sequence
<220> FEATURE:
<223> OTHER INFORMATION: 4.32.63 Anti-idiotypic scFv

<400> SEQUENCE: 29

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val Ser Trp Val Arg Gln Pro Pro Gly Lys Cys Leu Glu Trp Leu
            35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
                100                 105                 110

Gly Gln Gly Thr Ser Val Thr Val Ser Ser Gly Gly Gly Gly Ser Gly
            115                 120                 125

Gly Gly Gly Ser Gly Gly Gly Gly Ser Gly Gly Gly Gly Ser Asp Ile
        130                 135                 140
```

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys
                245

<210> SEQ ID NO 30
<211> LENGTH: 33
<212> TYPE: PRT
<213> ORGANISM: Artificial sequence
<220> FEATURE:
<223> OTHER INFORMATION: Linker 1

<400> SEQUENCE: 30

Gly Gly Gly Gly Ser Gly Gly Gly Ser Arg Gln Ala Arg Val Val
1               5                   10                  15

Asn Gly Gly Gly Gly Ser Gly Gly Gly Ser Gly Gly Gly Gly
                20                  25                  30

Ser

<210> SEQ ID NO 31
<211> LENGTH: 28
<212> TYPE: PRT
<213> ORGANISM: Artificial sequence
<220> FEATURE:
<223> OTHER INFORMATION: Linker 2

<400> SEQUENCE: 31

Gly Gly Gly Gly Ser Val His Met Pro Leu Gly Phe Leu Gly Pro Gly
1               5                   10                  15

Arg Ser Arg Gly Ser Phe Pro Gly Gly Gly Gly Ser
                20                  25

<210> SEQ ID NO 32
<211> LENGTH: 41
<212> TYPE: PRT
<213> ORGANISM: Artificial sequence
<220> FEATURE:
<223> OTHER INFORMATION: Linker 3

<400> SEQUENCE: 32

Gly Gly Gly Gly Ser Gly Gly Gly Gly Ser Arg Gln Ala Arg Val Val
1               5                   10                  15

Asn Gly Gly Gly Gly Ser Val Pro Leu Ser Leu Tyr Ser Gly Gly
                20                  25                  30

Gly Gly Gly Ser Gly Gly Gly Gly Ser
            35                  40

<210> SEQ ID NO 33
<211> LENGTH: 36
<212> TYPE: PRT

```
<213> ORGANISM: Artificial sequence
<220> FEATURE:
<223> OTHER INFORMATION: Linker 4

<400> SEQUENCE: 33

Gly Gly Gly Gly Ser Gly Gly Gly Ser Arg Gln Ala Arg Val Val
1               5                   10                  15

Asn Gly Val Pro Leu Ser Leu Tyr Ser Gly Gly Gly Gly Ser Gly
                20                  25                  30

Gly Gly Gly Ser
            35

<210> SEQ ID NO 34
<211> LENGTH: 33
<212> TYPE: PRT
<213> ORGANISM: Artificial sequence
<220> FEATURE:
<223> OTHER INFORMATION: Linker 5

<400> SEQUENCE: 34

Gly Gly Gly Gly Ser Val His Met Pro Leu Gly Phe Leu Gly Pro Arg
1               5                   10                  15

Gln Ala Arg Val Val Asn Gly Gly Gly Gly Ser Gly Gly Gly Gly
                20                  25                  30

Ser

<210> SEQ ID NO 35
<211> LENGTH: 35
<212> TYPE: PRT
<213> ORGANISM: Artificial sequence
<220> FEATURE:
<223> OTHER INFORMATION: Linker 6

<400> SEQUENCE: 35

Gly Gly Gly Gly Ser Val His Met Pro Leu Gly Phe Leu Gly Pro Arg
1               5                   10                  15

Gln Ala Arg Val Val Asn Gly Gly Gly Gly Ser Gly Gly Gly Gly
                20                  25                  30

Ser Gly Gly
        35

<210> SEQ ID NO 36
<211> LENGTH: 33
<212> TYPE: PRT
<213> ORGANISM: Artificial sequence
<220> FEATURE:
<223> OTHER INFORMATION: Linker 7

<400> SEQUENCE: 36

Gly Gly Gly Gly Ser Gly Gly Gly Gly Ser Gly Gly Gly Ser Phe
1               5                   10                  15

Val Gly Gly Thr Gly Gly Gly Gly Ser Gly Gly Gly Ser Gly Gly
                20                  25                  30

Ser

<210> SEQ ID NO 37
<211> LENGTH: 33
<212> TYPE: PRT
<213> ORGANISM: Artificial sequence
<220> FEATURE:
<223> OTHER INFORMATION: Linker 8
```

<400> SEQUENCE: 37

Gly Gly Gly Gly Ser Gly Gly Gly Gly Ser Lys Lys Ala Ala Pro Val
1               5                   10                  15

Asn Gly Gly Gly Gly Ser Gly Gly Gly Gly Ser Gly Gly Gly Gly
            20                  25                  30

Ser

<210> SEQ ID NO 38
<211> LENGTH: 33
<212> TYPE: PRT
<213> ORGANISM: Artificial sequence
<220> FEATURE:
<223> OTHER INFORMATION: Linker 9

<400> SEQUENCE: 38

Gly Gly Gly Gly Ser Gly Gly Gly Gly Ser Pro Met Ala Lys Lys Val
1               5                   10                  15

Asn Gly Gly Gly Gly Ser Gly Gly Gly Gly Ser Gly Gly Gly Gly
            20                  25                  30

Ser

<210> SEQ ID NO 39
<211> LENGTH: 33
<212> TYPE: PRT
<213> ORGANISM: Artificial sequence
<220> FEATURE:
<223> OTHER INFORMATION: Linker 10

<400> SEQUENCE: 39

Gly Gly Gly Gly Ser Gly Gly Gly Gly Ser Gln Ala Arg Ala Lys Val
1               5                   10                  15

Asn Gly Gly Gly Gly Ser Gly Gly Gly Gly Ser Gly Gly Gly Gly
            20                  25                  30

Ser

<210> SEQ ID NO 40
<211> LENGTH: 33
<212> TYPE: PRT
<213> ORGANISM: Artificial sequence
<220> FEATURE:
<223> OTHER INFORMATION: Linker 11

<400> SEQUENCE: 40

Gly Gly Gly Gly Ser Gly Gly Gly Gly Ser Val His Met Pro Leu Gly
1               5                   10                  15

Phe Leu Gly Pro Gly Gly Gly Gly Ser Gly Gly Gly Gly Ser Gly Gly
            20                  25                  30

Ser

<210> SEQ ID NO 41
<211> LENGTH: 33
<212> TYPE: PRT
<213> ORGANISM: Artificial sequence
<220> FEATURE:
<223> OTHER INFORMATION: Linker 12

<400> SEQUENCE: 41

Gly Gly Gly Gly Ser Gly Gly Gly Gly Ser Gln Ala Arg Ala Lys Gly
1               5                   10                  15

Gly Gly Gly Ser Gly Gly Gly Ser Gly Gly Gly Ser Gly Gly
            20                  25                  30
Ser

<210> SEQ ID NO 42
<211> LENGTH: 33
<212> TYPE: PRT
<213> ORGANISM: Artificial sequence
<220> FEATURE:
<223> OTHER INFORMATION: Linker 13

<400> SEQUENCE: 42

Gly Gly Gly Gly Ser Val His Met Pro Leu Gly Phe Leu Gly Pro Pro
1               5                   10                  15

Met Ala Lys Lys Gly Gly Gly Ser Gly Gly Gly Ser Gly Gly
            20                  25                  30
Ser

<210> SEQ ID NO 43
<211> LENGTH: 33
<212> TYPE: PRT
<213> ORGANISM: Artificial sequence
<220> FEATURE:
<223> OTHER INFORMATION: Linker 14

<400> SEQUENCE: 43

Gly Gly Gly Gly Ser Gly Gly Gly Ser Lys Lys Ala Ala Pro Gly
1               5                   10                  15

Gly Gly Ser Gly Gly Gly Ser Gly Gly Gly Ser Gly Gly
            20                  25                  30
Ser

<210> SEQ ID NO 44
<211> LENGTH: 33
<212> TYPE: PRT
<213> ORGANISM: Artificial sequence
<220> FEATURE:
<223> OTHER INFORMATION: Linker 15

<400> SEQUENCE: 44

Gly Gly Gly Gly Ser Gly Gly Gly Gly Ser Pro Met Ala Lys Lys Gly
1               5                   10                  15

Gly Gly Ser Gly Gly Gly Ser Gly Gly Gly Ser Gly Gly
            20                  25                  30
Ser

<210> SEQ ID NO 45
<211> LENGTH: 8
<212> TYPE: PRT
<213> ORGANISM: Artificial sequence
<220> FEATURE:
<223> OTHER INFORMATION: Recognition site 1

<400> SEQUENCE: 45

Arg Gln Ala Arg Val Val Asn Gly
1               5

<210> SEQ ID NO 46
<211> LENGTH: 18
<212> TYPE: PRT
<213> ORGANISM: Artificial sequence
<220> FEATURE:

<223> OTHER INFORMATION: Recognition site 2

<400> SEQUENCE: 46

Val His Met Pro Leu Gly Phe Leu Gly Pro Gly Arg Ser Arg Gly Ser
1               5                   10                  15

Phe Pro

<210> SEQ ID NO 47
<211> LENGTH: 21
<212> TYPE: PRT
<213> ORGANISM: Artificial sequence
<220> FEATURE:
<223> OTHER INFORMATION: Recognition site 3
<220> FEATURE:
<221> NAME/KEY: MISC_FEATURE
<222> LOCATION: (9)..(13)
<223> OTHER INFORMATION: X can be any naturally occuring amino acid

<400> SEQUENCE: 47

Arg Gln Ala Arg Val Val Asn Gly Xaa Xaa Xaa Xaa Xaa Val Pro Leu
1               5                   10                  15

Ser Leu Tyr Ser Gly
            20

<210> SEQ ID NO 48
<211> LENGTH: 16
<212> TYPE: PRT
<213> ORGANISM: Artificial sequence
<220> FEATURE:
<223> OTHER INFORMATION: Recognition site 4

<400> SEQUENCE: 48

Arg Gln Ala Arg Val Val Asn Gly Val Pro Leu Ser Leu Tyr Ser Gly
1               5                   10                  15

<210> SEQ ID NO 49
<211> LENGTH: 7
<212> TYPE: PRT
<213> ORGANISM: Artificial sequence
<220> FEATURE:
<223> OTHER INFORMATION: Recognition site 5

<400> SEQUENCE: 49

Pro Leu Gly Leu Trp Ser Gln
1               5

<210> SEQ ID NO 50
<211> LENGTH: 18
<212> TYPE: PRT
<213> ORGANISM: Artificial sequence
<220> FEATURE:
<223> OTHER INFORMATION: Recognition site 6

<400> SEQUENCE: 50

Val His Met Pro Leu Gly Phe Leu Gly Pro Arg Gln Ala Arg Val Val
1               5                   10                  15

Asn Gly

<210> SEQ ID NO 51
<211> LENGTH: 6
<212> TYPE: PRT
<213> ORGANISM: Artificial sequence
<220> FEATURE:
<223> OTHER INFORMATION: Recognition site 7

```
<400> SEQUENCE: 51

Phe Val Gly Gly Thr Gly
1               5

<210> SEQ ID NO 52
<211> LENGTH: 8
<212> TYPE: PRT
<213> ORGANISM: Artificial sequence
<220> FEATURE:
<223> OTHER INFORMATION: Recognition site 8

<400> SEQUENCE: 52

Lys Lys Ala Ala Pro Val Asn Gly
1               5

<210> SEQ ID NO 53
<211> LENGTH: 8
<212> TYPE: PRT
<213> ORGANISM: Artificial sequence
<220> FEATURE:
<223> OTHER INFORMATION: Recognition site 9

<400> SEQUENCE: 53

Pro Met Ala Lys Lys Val Asn Gly
1               5

<210> SEQ ID NO 54
<211> LENGTH: 8
<212> TYPE: PRT
<213> ORGANISM: Artificial sequence
<220> FEATURE:
<223> OTHER INFORMATION: Recognition site 10

<400> SEQUENCE: 54

Gln Ala Arg Ala Lys Val Asn Gly
1               5

<210> SEQ ID NO 55
<211> LENGTH: 10
<212> TYPE: PRT
<213> ORGANISM: Artificial sequence
<220> FEATURE:
<223> OTHER INFORMATION: Recognition site 11

<400> SEQUENCE: 55

Val His Met Pro Leu Gly Phe Leu Gly Pro
1               5                   10

<210> SEQ ID NO 56
<211> LENGTH: 5
<212> TYPE: PRT
<213> ORGANISM: Artificial sequence
<220> FEATURE:
<223> OTHER INFORMATION: Recognition site 12

<400> SEQUENCE: 56

Gln Ala Arg Ala Lys
1               5

<210> SEQ ID NO 57
<211> LENGTH: 15
<212> TYPE: PRT
<213> ORGANISM: Artificial sequence
<220> FEATURE:
<223> OTHER INFORMATION: Recognition site 13
```

```
<400> SEQUENCE: 57

Val His Met Pro Leu Gly Phe Leu Gly Pro Pro Met Ala Lys Lys
1               5                   10                  15

<210> SEQ ID NO 58
<211> LENGTH: 5
<212> TYPE: PRT
<213> ORGANISM: Artificial sequence
<220> FEATURE:
<223> OTHER INFORMATION: Recognition site 14

<400> SEQUENCE: 58

Lys Lys Ala Ala Pro
1               5

<210> SEQ ID NO 59
<211> LENGTH: 5
<212> TYPE: PRT
<213> ORGANISM: Artificial sequence
<220> FEATURE:
<223> OTHER INFORMATION: Recognition site 15

<400> SEQUENCE: 59

Pro Met Ala Lys Lys
1               5

<210> SEQ ID NO 60
<211> LENGTH: 207
<212> TYPE: PRT
<213> ORGANISM: Artificial sequence
<220> FEATURE:
<223> OTHER INFORMATION: hu CD3e

<400> SEQUENCE: 60

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 61
<211> LENGTH: 1353
<212> TYPE: DNA
<213> ORGANISM: Artificial sequence
<220> FEATURE:
<223> OTHER INFORMATION: anti FolR1 16D5 VH CH1 Fc hole HRYF, pCON983

<400> SEQUENCE: 61

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacca agggcccctc cgtgttcccc ctggccccca gcagcaagag caccagcggc     420
ggcacagccg ctctgggctg cctggtcaag gactacttcc ccgagcccgt gaccgtgtcc     480
tggaacagcg gagccctgac ctccggcgtg cacaccttcc cgccgtgct gcagagttct      540
ggcctgtata gcctgagcag cgtggtcacc gtgccttcta gcagcctggg cacccagacc     600
tacatctgca acgtgaacca caagcccagc aacaccaagg tggacaagaa ggtggagccc     660
aagagctgcg acaaaactca cacatgccca ccgtgcccag cacctgaagc tgcaggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcggagga gcagtacaac      900
agcacgtacc gtgtggtcag cgtcctcacc gtcctgcacc aggactggct gaatggcaag     960
gagtacaagt gcaaggtctc caacaaagcc ctcggcgccc ccatcgagaa aaccatctcc    1020
aaagccaaag gcagccccg agaaccacag gtgtgcaccc tgcccccatc ccgggatgag     1080
ctgaccaaga accaggtcag cctctcgtgc gcagtcaaag gcttctatcc agcgacatc      1140
gccgtggagt gggagagcaa tgggcagccg gagaacaact acaagaccac gcctcccgtg    1200
ctggactccg acggctcctt cttcctcgtg agcaagctca ccgtggacaa gagcaggtgg    1260
cagcagggga acgtcttctc atgctccgtg atgcatgagg ctctgcacaa ccgcttcacg    1320
cagaagagcc tctccctgtc tccgggtaaa tga                                 1353
```

<210> SEQ ID NO 62
<211> LENGTH: 2070
<212> TYPE: DNA
<213> ORGANISM: Artificial sequence
<220> FEATURE:
<223> OTHER INFORMATION: CD3 CH2527-VH3_23-12 CH1 (G4S)2 FolR1 16D5 VH
       CH1 Fc knob P329G LALA, pETR13932

<400> SEQUENCE: 62

```
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg gtgtccggg atcagaagca agtacaacaa ctacgccacc      180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact tcggcaacag ctatgtgtct tggtttgcct actggggcca gggcacccgc     360
```

```
gtgaccgtgt catctgctag cacaaagggc cctagcgtgt tccctctggc ccccagcagc    420
aagagcacaa gcggcggaac agccgccctg ggctgcctcg tgaaggacta cttccccgag    480
cccgtgacag tgtcttggaa cagcggagcc ctgacaagcg gcgtgcacac cttccctgcc    540
gtgctgcaga gcagcggcct gtactccctg agcagcgtgg tcaccgtgcc tagcagcagc    600
ctgggcaccc agacctacat ctgcaacgtg aaccacaagc ccagcaacac caaagtggac    660
aagaaggtgg agcccaagag ctgtgatggc ggaggagggt ccgaggcgg aggatccgag    720 gtgcaattgg ttgaatctgg tggtggtctg gtaaaaccgg cggttccct gcgtctgagc    780 tgcgcggctt ccggattcac cttctccaac gcgtggatga gctgggttcg ccaggccccg    840
ggcaaaggcc tcgagtgggt tggtcgtatc aagtctaaaa ctgacggtgg caccacggat    900
tacgcggctc cagttaaagg tcgttttacc atttcccgcg acgatagcaa aaacactctg    960
tatctgcaga tgaactctct gaaaactgaa gacaccgcag tctactactg tactaccccg   1020
tgggaatggt cttggtacga ttattgggc cagggcacgc tggttacggt gtctagcgct   1080
agtaccaagg gcccagcgt gttccccctg gcacccagca gcaagagcac atctggcgga   1140
acagccgctc tgggctgtct ggtgaaagac tacttcccg agcccgtgac cgtgtcttgg   1200
aactctggcg ccctgaccag cggcgtgcac accttccag ccgtgctgca gagcagcggc   1260
ctgtactccc tgtcctccgt ggtcaccgtg ccctctagct ccctgggaac acagacatat   1320
atctgtaatg tcaatcacaa gccttccaac accaaagtcg ataagaaagt cgagcccaag   1380
agctgcgaca aaactcacac atgcccaccg tgcccagcac ctgaagctgc agggggaccg   1440
tcagtcttcc tcttcccccc aaaacccaag gacaccctca tgatctcccg gacccctgag   1500
gtcacatgcg tggtggtgga cgtgagccac gaagaccctg aggtcaagtt caactggtac   1560
gtggacggcg tggaggtgca taatgccaag acaaagccgc gggaggagca gtacaacagc   1620
acgtaccgtg tggtcagcgt cctcaccgtc ctgcaccagg actggctgaa tggcaaggag   1680
tacaagtgca aggtctccaa caaagccctc ggcgccccca tcgagaaaac catctccaaa   1740
gccaaagggc agccccgaga accacaggtg tacaccctgc ccccatgccg ggatgagctg   1800
accaagaacc aggtcagcct gtggtgcctg gtcaaaggct tctatcccag cgacatcgcc   1860
gtggagtggg agagcaatgg gcagccggag aacaactaca agaccacgcc tcccgtgctg   1920
gactccgacg gctccttctt cctctacagc aagctcaccg tggacaagag caggtggcag   1980
caggggaacg tcttctcatg ctccgtgatg catgaggctc tgcacaacca ctacacgcag   2040
aagagcctct ccctgtctcc gggtaaatga                                    2070

<210> SEQ ID NO 63
<211> LENGTH: 648
<212> TYPE: DNA
<213> ORGANISM: Artificial sequence
<220> FEATURE:
<223> OTHER INFORMATION: LC Common light chain pETR13197

<400> SEQUENCE: 63
caggccgtcg tgacccagga acccagcctg acagtgtctc ctggcggcac cgtgaccctg     60
acatgtggca gttctacagg cgccgtgacc accagcaact acgccaactg ggtgcaggaa    120
aagcccggcc aggccttcag aggactgatc ggcggcacca caagagagc cctggcacc     180 cctgccagat tcagcggatc tctgctggga ggaaaggccg ccctgacact gtctggcgcc    240
cagccagaag atgaggccga gtactactgc gccctgtggt acagcaacct gtgggtgttc    300
```

```
ggcggaggca ccaagctgac agtcctaggt caacccaagg ctgcccccag cgtgaccctg      360
ttccccccca gcagcgagga actgcaggcc aacaaggcca ccctggtctg cctgatcagc      420
gacttctacc caggcgccgt gaccgtggcc tggaaggccg acagcagccc cgtgaaggcc      480
ggcgtggaga ccaccacccc cagcaagcag agcaacaaca agtacgccgc cagcagctac      540
ctgagcctga cccccgagca gtggaagagc acaggtcct acagctgcca ggtgacccac       600
gagggcagca ccgtggagaa aaccgtggcc cccaccgagt gcagctga                   648
```

<210> SEQ ID NO 64
<211> LENGTH: 2916
<212> TYPE: DNA
<213> ORGANISM: Artificial sequence
<220> FEATURE:
<223> OTHER INFORMATION: anti CD3 (CH2527 VH_3-23(12) VL7-46(13)) scFv
      4.32.63 MMP9 Matriptase MK062 CH2527 VH3_23-VH12 CH1 FolR1 16D5 VH
      CH1 hum Fc knob PG LALA, pETR16546

<400> SEQUENCE: 64

```
caagtgcagc tgaaagagtc cggccctgga ctggtggccc ctagccagag cctgagcatc      60
acctgtaccg tgtccggctt cagcctgacc agctacggcg tgtcatgggt gcgccagcct     120
ccaggcaagt gtctggaatg gctgggcatc atctgggcg acggcagcac caattaccac      180
agcgccctga tcagcagact gagcatctcc aaggacaaca gcaagagcca ggtgttcctg     240
aagctgaaca gcctgcagac cgacgacacc gccacctact actgcgccaa gggcatcacc     300
accgtggtgg acgactacta cgctatggac tactggggcc agggcaccag cgtgacagtg     360
tctagcggag gcggaggatc tggcggcgga ggaagtggcg agggggatc tgggggaggc     420 ggaagcgata tccagatgac ccagagccct gccagcctgt ctgcctctgt gggcgagaca     480
gtgaccatca catgccgggc cagcgagaac atcgacagct acctggcctg gtatcagcag     540
aagcagggca agagccccca gctgctggtg tacgccgcca cctttctggc cgacgatgtg     600
cccagcagat tcagcggcag cggaagcggc acacagtaca gcctgaagat caactccctg     660
cagagcgagg acgtggcccg gtactactgc cagcactact acagcacccc ctacaccttc     720
ggctgcggca ccaagctgga aatcaaagga ggcggcggaa gtgtgcacat gcccctgggc     780
ttcctgggcc ccagacaggc cagagtcgtg aacgggggg gcggaggcag tgggggggga     840
ggatccgagt gcagctgct ggaatctggc ggcggactgg tgcagcctgg cggatctctg     900
agactgagct gtgccgccag cggcttcacc ttcagcacct acgccatgaa ctgggtgcgc     960
caggcccctg gcaaaggcct ggaatgggtg tccggatca gaagcaagta caacaactac    1020
gccacctact acgccgacag cgtgaagggc cggttcacca tcagccggga cgacagcaag    1080
aacaccctgt acctgcagat gaacagcctg cgggccgagg acaccgccgt gtactattgt    1140
gtgcggcacg gcaacttcgg caacagctat gtgtcttggt ttgcctactg gggccagggc    1200
accctcgtga ccgtgtcaag cgctagcaca aagggcccta gcgtgttccc tctggccccc    1260
agcagcaaga gcacaagcgg cggaacagcc gccctgggct gcctcgtgaa ggactacttc    1320
cccgagcccg tgacagtgtc ttggaacagc ggagccctga caagcggcgt gcacaccttc    1380
cctgccgtgc tgcagagcag cggcctgtac tccctgagca gcgtggtcac cgtgcctagc    1440
agcagcctgg gcacccagac ctacatctgc aacgtgaacc acaagcccag caacaccaaa    1500
gtggacaaga aggtggagcc caagagctgt gatggcggag agggtccgg ggcggagga    1560 tccgaggtgc aattggttga atctggtggt ggtctggtaa aaccgggcgg ttccctgcgt    1620
ctgagctgcg cggcttccgg gttcaccttc tccaacgcgt ggatgagctg ggttcgccag    1680
```

```
gccccgggca aaggcctcga gtgggttggt cgtatcaagt ctaaaactga cggtggcacc   1740
acggattacg cggctccagt taaaggtcgt tttaccattt cccgcgacga tagcaaaaac   1800
actctgtatc tgcagatgaa ctctctgaaa actgaagaca ccgcagtcta ctactgtact   1860
accccgtggg aatggtcttg gtacgattat tggggccagg gcacgctggt tacggtgtct   1920
agcgctagta ccaagggccc cagcgtgttc cccctggcac ccagcagcaa gagcacatct   1980
ggcggaacag ccgctctggg ctgtctggtg aaagactact cccccagcc cgtgaccgtg   2040 tcttggaact ctggcgccct gaccagcggc gtgcacacct tccagccgt gctgcagagc   2100 agcggcctgt actccctgtc ctccgtggtc accgtgccct ctagctccct gggaacacag   2160
acatatatct gtaatgtcaa tcacaagcct tccaacacca agtcgataa gaaagtcgag   2220 cccaagagct cgacaaaac tcacacatgc ccaccgtgcc cagcacctga gctgcaggg   2280 ggaccgtcag tcttcctctt ccccccaaaa cccaaggaca ccctcatgat ctcccggacc   2340
cctgaggtca catgcgtggt ggtggacgtg agccacgaag accctgaggt caagttcaac   2400
tggtacgtgg acggcgtgga ggtgcataat gccaagacaa agccgcggga ggagcagtac   2460
aacagcacgt accgtgtggt cagcgtcctc accgtcctgc accaggactg gctgaatggc   2520
aaggagtaca agtgcaaggt ctccaacaaa gccctcggcg cccccatcga gaaaaccatc   2580
tccaaagcca agggcagcc cgagaaccag caggtgtaca ccctgcccc atgccgggat   2640 gagctgacca gaaccaggt cagcctgtgg tgcctggtca aaggcttcta tcccagcgac   2700
atcgccgtgg agtgggagag caatgggcag ccggagaaca actacaagac cacgcctccc   2760
gtgctggact ccgacggctc cttcttcctc tacagcaagc tcaccgtgga caagagcagg   2820
tggcagcagg ggaacgtctt ctcatgctcc gtgatgcatg aggctctgca caaccactac   2880
acgcagaaga gcctctccct gtctccgggt aaatga                             2916
```

<210> SEQ ID NO 65
<211> LENGTH: 2916
<212> TYPE: DNA
<213> ORGANISM: Artificial sequence
<220> FEATURE:
<223> OTHER INFORMATION: anti CD3 (CH2527 VH_3-23(12) VL7-46(13)) scFv
      4.32.63 Cathepsin S/B site CH2527 VH3_23-VH12 CH1 FolR1 16D5 VH
      CH1 hum Fc knob PG LALA, pETR16550

<400> SEQUENCE: 65

```
caagtgcagc tgaaagagtc cggccctgga ctggtggccc ctagccagag cctgagcatc    60
acctgtaccg tgtccggctt cagcctgacc agctacggcg tgtcatgggt gcgccagcct   120
ccaggcaagt gtctggaatg gctgggcatc atctggggcg acggcagcac caattaccac   180
agcgccctga tcagcagact gagcatctcc aaggacaaca gcaagagcca ggtgttcctg   240
aagctgaaca gcctgcagac cgacgacacc gccacctact actgcgccaa gggcatcacc   300
accgtggtgg acgactacta cgctatggac tactggggcc agggcaccag cgtgacagtg   360
tctagcggag gcggaggatc tggcggcgga ggaagtggcg agggggatc tgggggaggc   420 ggaagcgata tccagatgac ccagagccct gccagcctgt ctgcctctgt gggcgagaca   480
gtgaccatca catgccgggc cagcgagaac atcgacagct acctggcctg gtatcagcag   540
aagcagggca agagccccca gctgctggtg tacgccgcca cctttctggc cgacgatgtg   600
cccagcagat cgcgggcag cggaagcggc acacagtaca gcctgaagat caactccctg   660
cagagcgagg acgtggcccg gtactactgc cagcactact acagcacccc ctacaccttc   720
```

```
ggctgcggca ccaagctgga aatcaaaggc gggggaggct ccggaggcgg cggaagtgga      780
ggcggcggaa gtttcgtggg ggggaccggg ggcggaggca gtgggggggg aggatccggg      840
ggatccgagg tgcagctgct ggaatctggc ggcggactgg tgcagcctgg cggatctctg      900
agactgagct gtgccgccag cggcttcacc ttcagcacct acgccatgaa ctgggtgcgc      960
caggcccctg gcaaaggcct ggaatgggtg tcccggatca gaagcaagta caacaactac     1020
gccacctact acgccgacag cgtgaagggc cggttcacca tcagccggga cgacagcaag     1080
aacaccctgt acctgcagat gaacagcctg cgggccgagg acaccgccgt gtactattgt     1140
gtgcggcacg gcaacttcgg caacagctat gtgtcttggt ttgcctactg gggcagggc      1200 accctcgtga ccgtgtcaag cgctagcaca aagggcccta gcgtgttccc tctggccccc     1260
agcagcaaga gcacaagcgg cggaacagcc gccctgggct gcctcgtgaa ggactacttc     1320
cccgagcccg tgacagtgtc ttggaacagc ggagccctga caagcggcgt gcacaccttc     1380
cctgccgtgc tgcagagcag cggcctgtac tccctgagca gcgtggtcac cgtgcctagc     1440
agcagcctgg gcacccagac ctacatctgc aacgtgaacc acaagcccag caacaccaaa     1500
gtggacaaga aggtggagcc caagagctgt gatggcggag agggtccgg gggcggagga      1560 tccgaggtgc aattggttga atctggtggt ggtctggtaa accgggcgg ttccctgcgt      1620 ctgagctgcg cggcttccgg gttcaccttc tccaacgcgt ggatgagctg ggttcgccag     1680
gccccgggca aaggcctcga gtgggttggt cgtatcaagt ctaaaactga cggtggcacc     1740
acggattacg cggctccagt taaaggtcgt tttaccattt cccgcgacga tagcaaaaac     1800
actctgtatc tgcagatgaa ctctctgaaa actgaagaca ccgcagtcta ctactgtact     1860
accccgtggg aatggtcttg gtacgattat tggggccagg gcacgctggt tacggtgtct     1920
agcgctagta ccaagggccc cagcgtgttc cccctggcac ccagcagcaa gagcacatct     1980
ggcggaacag ccgctctggg ctgtctggtg aaagactact ccccgagcc cgtgaccgtg     2040 tcttggaact ctggcgccct gaccagcggc gtgcacacct tccagccgt gctgcagagc     2100 agcggcctgt actccctgtc ctccgtggtc accgtgccct ctagctccct gggaacacag     2160
acatatatct gtaatgtcaa tcacaagcct tccaacacca aagtcgataa gaaagtcgag     2220
cccaagagct gcgacaaaac tcacacatgc ccaccgtgcc cagcacctga agctgcaggg     2280
ggaccgtcag tcttcctctt cccccccaaaa cccaaggaca ccctcatgat ctcccggacc     2340
cctgaggtca catgcgtggt ggtggacgtg agccacgaag accctgaggt caagttcaac     2400
tggtacgtgg acggcgtgga ggtgcataat gccaagacaa agccgcggga ggagcagtac     2460
aacagcacgt accgtgtggt cagcgtcctc accgtcctgc accaggactg gctgaatggc     2520
aaggagtaca agtgcaaggt ctccaacaaa gccctcggcg cccccatcga aaaaccatc     2580 tccaaagcca agggcagccc ccgagaacca caggtgtaca ccctgccccc atgccgggat     2640
gagctgacca agaaccaggt cagcctgtgg tgcctggtca aaggcttcta tcccagcgac     2700
atcgccgtgg agtgggagag caatgggcag ccggagaaca actacaagac cacgcctccc     2760
gtgctggact ccgacggctc cttcttcctc tacagcaagc tcaccgtgga caagagcagg     2820
tggcagcagg gaacgtcttt ctcatgctcc gtgatgcatg aggctctgca caaccactac     2880
acgcagaaga gcctctccct gtctccgggt aaatga                               2916
```

<210> SEQ ID NO 66
<211> LENGTH: 2916
<212> TYPE: DNA
<213> ORGANISM: Artificial sequence
<220> FEATURE:
<223> OTHER INFORMATION: anti CD3 (CH2527 VH_3-23(12) VL7-46(13)) scFv
4.32.63 Matriptase MK062 CH2527 VH3_23-VH12 CH1 FolR1 16D5 VH CH1
hum Fc knob PG LALA, pETR15599

<400> SEQUENCE: 66

| | | | | | |
|---|---|---|---|---|---|
| caagtgcagc | tgaaagagtc | cggccctgga | ctggtggccc | ctagccagag | cctgagcatc | 60 |
| acctgtaccg | tgtccggctt | cagcctgacc | agctacggcg | tgtcatgggt | gcgccagcct | 120 |
| ccaggcaagt | gtctggaatg | gctgggcatc | atctggggcg | acggcagcac | caattaccac | 180 |
| agcgccctga | tcagcagact | gagcatctcc | aaggacaaca | gcaagagcca | ggtgttcctg | 240 |
| aagctgaaca | gcctgcagac | cgacgacacc | gccacctact | actgcgccaa | gggcatcacc | 300 |
| accgtggtgg | acgactacta | cgctatggac | tactggggcc | agggcaccag | cgtgacagtg | 360 |
| tctagcggag | gcgaggatc | tggcggcgga | ggaagtggcg | gaggggatc | tggggaggc | 420 |
| ggaagcgata | tccagatgac | ccagagccct | gccagcctgt | ctgcctctgt | gggcgagaca | 480 |
| gtgaccatca | catgccgggc | cagcgagaac | atcgacagc | acctggcctg | gtatcagcag | 540 |
| aagcagggca | agagccccca | gctgctggtg | tacgccgcca | cctttctggc | cgacgatgtg | 600 |
| cccagcagat | tcagcggcag | cggaagcggc | acacagtaca | gcctgaagat | caactccctg | 660 |
| cagagcgagg | acgtggcccg | gtactactgc | cagcactact | acagcacccc | ctacaccttc | 720 |
| ggctgcggca | ccaagctgga | aatcaaaggc | ggggaggct | ccggaggcgg | cggaagtaga | 780 |
| caggccagag | tcgtgaacgg | gggagggggg | ggaagtgggg | gcggaggcag | tggggcgga | 840 |
| ggatccgagt | gcagctgct | ggaatctggc | ggcggactgg | tgcagcctgg | cggatctctg | 900 |
| agactgagct | gtgccgccag | cggcttcacc | ttcagcacct | acgccatgaa | ctgggtgcgc | 960 |
| caggcccctg | gcaaaggcct | ggaatgggtg | tccggatca | agcaagta | caacaactac | 1020 |
| gccacctact | acgccgacag | cgtgaagggc | cggttcacca | tcagccggga | cgacagcaag | 1080 |
| aacccctgt | acctgcagat | gaacagcctg | cgggccgagg | acaccgccgt | gtactattgt | 1140 |
| gtgcggcacg | gcaacttcgg | caacagctat | gtgtcttggt | ttgcctactg | gggccagggc | 1200 |
| accctcgtga | ccgtgtcaag | cgctagcaca | aagggcccta | gcgtgttccc | tctggccccc | 1260 |
| agcagcaaga | gcacaagcgg | cggaacagcc | gccctgggct | gcctcgtgaa | ggactacttc | 1320 |
| cccgagcccg | tgacagtgtc | ttggaacagc | ggagccctga | caagcggcgt | gcacaccttc | 1380 |
| cctgccgtgc | tgcagagcag | cggcctgtac | tccctgagca | gcgtggtcac | cgtgcctagc | 1440 |
| agcagcctgg | gcacccagac | ctacatctgc | aacgtgaacc | acaagcccag | caacaccaaa | 1500 |
| gtggacaaga | aggtggagcc | caagagctgt | gatggcggag | agggtccgg | gggcggagga | 1560 |
| tccgaggtgc | aattggttga | atctggtggt | ggtctggtaa | aaccgggcgg | ttccctgcgt | 1620 |
| ctgagctgcg | cggcttccgg | gttcaccttc | tccaacgcgt | ggatgagctg | ggttcgccag | 1680 |
| gccccgggca | aaggcctcga | gtgggttggt | cgtatcaagt | ctaaaactga | cggtggcacc | 1740 |
| acggattacg | cggctccagt | taaaggtcgt | tttaccattt | cccgcgacga | tagcaaaaac | 1800 |
| actctgtatc | tgcagatgaa | ctctctgaaa | actgaagaca | ccgcagtcta | ctactgtact | 1860 |
| accccgtggg | aatggtcttg | gtacgattat | tggggccagg | gcacgctggt | tacggtgtct | 1920 |
| agcgctagta | ccaagggccc | cagcgtgttc | cccctggcac | ccagcagcaa | gagcacatct | 1980 |
| ggcggaacag | ccgctctggg | ctgtctggtg | aaagactact | tccccgagcc | cgtgaccgtg | 2040 |
| tcttggaact | ctggcgccct | gaccagcggc | gtgcacacct | tccagcgt | gctgcagagc | 2100 |
| agcggcctgt | actccctgtc | ctcgtggtc | accgtgccct | ctagctccct | gggaacacag | 2160 |

```
acatatatct gtaatgtcaa tcacaagcct tccaacacca aagtcgataa gaaagtcgag    2220
cccaagagct gcgacaaaac tcacacatgc ccaccgtgcc cagcacctga agctgcaggg    2280
ggaccgtcag tcttcctctt ccccccaaaa cccaaggaca ccctcatgat ctcccggacc    2340
cctgaggtca catgcgtggt ggtggacgtg agccacgaag accctgaggt caagttcaac    2400
tggtacgtgg acggcgtgga ggtgcataat gccaagacaa agccgcggga ggagcagtac    2460
aacagcacgt accgtgtggt cagcgtcctc accgtcctgc accaggactg gctgaatggc    2520
aaggagtaca agtgcaaggt ctccaacaaa gccctcggcg cccccatcga gaaaaccatc    2580
tccaaagcca aagggcagcc ccgagaacca caggtgtaca ccctgccccc atgccgggat    2640
gagctgacca agaaccaggt cagcctgtgg tgcctggtca aaggcttcta tcccagcgac    2700
atcgccgtgg agtgggagag caatgggcag ccggagaaca actacaagac cacgcctccc    2760
gtgctggact ccgacggctc cttcttcctc tacagcaagc tcaccgtgga caagagcagg    2820
tggcagcagg ggaacgtctt ctcatgctcc gtgatgcatg aggctctgca caaccactac    2880
acgcagaaga gcctctccct gtctccgggt aaatga                             2916
```

<210> SEQ ID NO 67
<211> LENGTH: 2916
<212> TYPE: DNA
<213> ORGANISM: Artificial sequence
<220> FEATURE:
<223> OTHER INFORMATION: anti CD3 (CH2527 VH_3-23(12) VL7-46(13)) scFv
      4.32.63 non cleavable linker CH2527 VH3_23-VH12 CH1 FolR1 16D5 VH
      CH1 hum Fc knob PG LALA, pETR15603

<400> SEQUENCE: 67

```
caagtgcagc tgaaagagtc cggccctgga ctggtggccc ctagccagag cctgagcatc     60
acctgtaccg tgtccggctt cagcctgacc agctacggcg tgtcatgggt gcgccagcct    120
ccaggcaagt gtctggaatg gctgggcatc atctgggcg acggcagcac caattaccac     180
agcgccctga tcagcagact gagcatctcc aaggacaaca gcaagagcca ggtgttcctg    240
aagctgaaca gcctgcagac cgacgacacc gccacctact actgcgccaa gggcatcacc    300
accgtggtgg acgactacta cgctatggac tactgggggcc agggcaccag cgtgacagtg    360
tctagcggag gcggaggatc tggcggcgga ggaagtggcg gagggggatc tgggggaggc    420
ggaagcgata tccagatgac ccagagccct gccagcctgt ctgcctctgt gggcgagaca    480
gtgaccatca catgccgggc cagcgagaac atcgacagct acctggcctg gtatcagcag    540
aagcagggca gagcccccca gctgctggtg tacgccgcca cctttctggc cgacgatgtg    600
cccagcagat tcagcggcag cggaagcggc acacagtaca gcctgaagat caactccctg    660
cagagcgagg acgtggcccg gtactactgc cagcactact acagcacccc ctacaccttc    720
ggctgcggca ccaagctgga aatcaaaggc gggggaggct ccggaggcgg cggaagtgga    780
ggcggcggaa gtggcggagg cggagggggg ggaagtgggg gcggaggcag tgggggggga    840
ggatccgagg tgcagctgct ggaatctggg ggcggactgg tgcagcctgg cggatctctg    900
agactgagct gtgccgccag cggcttcacc ttcagcacct acgccatgaa ctgggtgcgc    960
caggcccctg gcaagggcct ggaatgggtg tccggatca gaagcaagta caacaactac    1020
gccacctact acgccgacag cgtgaagggc cggttcacca tcagccggga cgacagcaag    1080
aacaccctgt acctgcagat gaacagcctg cgggccgagg acaccgccgt gtactattgt    1140
gtgcggcacg gcaacttcgg caacagctat gtgtcttggt ttgcctactg gggccagggc    1200
accctcgtga ccgtgtcaag cgctagcaca aagggcccta gcgtgttccc tctggccccc    1260
```

-continued

```
agcagcaaga gcacaagcgg cggaacagcc gccctgggct gcctcgtgaa ggactacttc    1320
cccgagcccg tgacagtgtc ttggaacagc ggagccctga caagcggcgt gcacaccttc    1380
cctgccgtgc tgcagagcag cggcctgtac tccctgagca gcgtggtcac cgtgcctagc    1440
agcagcctgg gcacccagac ctacatctgc aacgtgaacc acaagccag caacaccaaa     1500 gtggacaaga aggtggagcc caagagctgt gatggcggag agggtccgg aggcggaggc      1560 tccgaggtgc aattggttga atctggtggt ggtctggtaa accgggcgg ttccctgcgt      1620 ctgagctgcg cggcttccgg attcaccttc tccaacgcgt ggatgagctg ggttcgccag    1680
gccccgggca aaggcctcga gtgggttggt cgtatcaagt ctaaaactga cggtggcacc     1740
acggattacg cggctccagt taaaggtcgt tttaccattt cccgcgacga tagcaaaaac    1800
actctgtatc tgcagatgaa ctctctgaaa actgaagaca ccgcagtcta ctactgtact    1860
accccgtggg aatggtcttg gtacgattat tggggccagg gcacgctggt tacggtgtct    1920
agcgctagta ccaagggccc cagcgtgttc cccctggcac ccagcagcaa gagcacatct    1980
ggcggaacag ccgctctggg ctgtctggtg aaagactact cccccgagcc cgtgaccgtg    2040
tcttggaact ctggcgccct gaccagcggc gtgcacacct ttccagccgt gctgcagagc    2100
agcggcctgt actccctgtc ctccgtggtc accgtgccct ctagctccct gggaacacag    2160
acatatatct gtaatgtcaa tcacaagcct tccaacacca agtcgataa gaaagtcgag     2220 cccaagagct gcgacaaaac tcacacatgc ccaccgtgcc cagcacctga gctgcaggg     2280 ggaccgtcag tcttcctctt ccccccaaaa cccaaggaca ccctcatgat ctcccggacc    2340
cctgaggtca catgcgtggt ggtggacgtg agccacgaag accctgaggt caagttcaac    2400
tggtacgtgg acggcgtgga ggtgcataat gccaagacaa agccgcggga ggagcagtac    2460
aacagcacgt accgtgtggt cagcgtcctc accgtcctgc accaggactg gctgaatggc    2520
aaggagtaca agtgcaaggt ctccaacaaa gccctcggcg cccccatcga gaaaaccatc    2580
tccaaagcca aagggcagcc ccgagaacca caggtgtaca ccctgccccc atgccgggat    2640
gagctgacca agaaccaggt cagcctgtgg tgcctggtca aaggcttcta tcccagcgac    2700
atcgccgtgg agtgggagag caatgggcag ccggagaaca actacaagac cacgcctccc    2760
gtgctggact ccgacggctc cttcttcctc tacagcaagc tcaccgtgga caagagcagg    2820
tggcagcagg ggaacgtctt ctcatgctcc gtgatgcatg aggctctgca caaccactac    2880
acgcagaaga gcctctccct gtctccgggt aaatga                              2916
```

```
<210> SEQ ID NO 68
<211> LENGTH: 10
<212> TYPE: DNA
<213> ORGANISM: Artificial sequence
<220> FEATURE:
<223> OTHER INFORMATION: Repeat 1 DNA

<400> SEQUENCE: 68
gggaatttcc                                                              10

<210> SEQ ID NO 69
<211> LENGTH: 11
<212> TYPE: DNA
<213> ORGANISM: Artificial sequence
<220> FEATURE:
<223> OTHER INFORMATION: Repeat 2 DNA
```

```
<400> SEQUENCE: 69
ggggactttc c                                                        11

<210> SEQ ID NO 70
<211> LENGTH: 10
<212> TYPE: DNA
<213> ORGANISM: Artificial sequence
<220> FEATURE:
<223> OTHER INFORMATION: Repeat 3 DNA

<400> SEQUENCE: 70
gggactttcc                                                          10

<210> SEQ ID NO 71
<211> LENGTH: 9
<212> TYPE: DNA
<213> ORGANISM: Artificial sequence
<220> FEATURE:
<223> OTHER INFORMATION: Repeat 4 DNA

<400> SEQUENCE: 71 gggacttcc                                                           9

<210> SEQ ID NO 72
<211> LENGTH: 11
<212> TYPE: DNA
<213> ORGANISM: Artificial sequence
<220> FEATURE:
<223> OTHER INFORMATION: Repeat 5 DNA

<400> SEQUENCE: 72
attgtagcgt a                                                        11

<210> SEQ ID NO 73
<211> LENGTH: 52
<212> TYPE: DNA
<213> ORGANISM: Artificial sequence
<220> FEATURE:
<223> OTHER INFORMATION: Response element 1 DNA

<400> SEQUENCE: 73
gggaatttcc gggactttc cgggaatttc cgggggacttt ccgggaattt cc           52

<210> SEQ ID NO 74
<211> LENGTH: 60
<212> TYPE: DNA
<213> ORGANISM: Artificial sequence
<220> FEATURE:
<223> OTHER INFORMATION: Response element 2 DNA

<400> SEQUENCE: 74
gggaatttcc gggaatttcc gggaatttcc gggaatttcc gggaatttcc gggaatttcc   60

<210> SEQ ID NO 75
<211> LENGTH: 59
<212> TYPE: DNA
<213> ORGANISM: Artificial sequence
<220> FEATURE:
<223> OTHER INFORMATION: Response element 3 DNA

<400> SEQUENCE: 75
gggacttccg ggactttccg ggactttccg ggactttccg ggactttccg ggactttcc    59

<210> SEQ ID NO 76
```

-continued

```
<211> LENGTH: 71
<212> TYPE: DNA
<213> ORGANISM: Artificial sequence
<220> FEATURE:
<223> OTHER INFORMATION: Response element 4 DNA

<400> SEQUENCE: 76
gggactttcc attgtagcgt agggactttc cattgtagcg tagggctttc cattgtagcg    60
tagggctttc c                                                        71

<210> SEQ ID NO 77
<211> LENGTH: 442
<212> TYPE: PRT
<213> ORGANISM: Artificial sequence
<220> FEATURE:
<223> OTHER INFORMATION: p95HER2 VH-CH1(EE)-Fc (hole, P329G LALA)

<400> SEQUENCE: 77
```

Glu Val Gln Leu Val Glu Ser Gly Gly Gly Ile Val Gln Pro Gly Gly
1               5                   10                  15

Ser Leu Lys Leu Ser Cys Ala Ala Ser Gly Phe Thr Phe Asn Asp Phe
            20                  25                  30

Gly Met Ser Trp Ile Arg Gln Thr Pro Asp Lys Arg Leu Glu Leu Val
        35                  40                  45

Ala Thr Ile Asn Thr Asn Gly Gly Thr Thr His Tyr Pro Asp Asn Val
    50                  55                  60

Lys Gly Arg Phe Ser Ile Ser Arg Asp Asn Ala Lys Lys Phe Val Tyr
65                  70                  75                  80

Leu Gln Met Ser Ser Leu Lys Ser Asp Asp Thr Ala Ile Tyr Tyr Cys
                85                  90                  95

Pro Arg Glu Gly Leu Asp Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

```
Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Cys Thr Leu Pro Pro Ser Arg
            340                 345                 350

Asp Glu Leu Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro
        435                 440

<210> SEQ ID NO 78
<211> LENGTH: 667
<212> TYPE: PRT
<213> ORGANISM: Artificial sequence
<220> FEATURE:
<223> OTHER INFORMATION: p95HER2 VH-CH1(EE)-CD3 VL-CH1-Fc (knob, P329G
      LALA)

<400> SEQUENCE: 78

Glu Val Gln Leu Val Glu Ser Gly Gly Gly Ile Val Gln Pro Gly Gly
1               5                   10                  15

Ser Leu Lys Leu Ser Cys Ala Ala Ser Gly Phe Thr Phe Asn Asp Phe
            20                  25                  30

Gly Met Ser Trp Ile Arg Gln Thr Pro Asp Lys Arg Leu Glu Leu Val
        35                  40                  45

Ala Thr Ile Asn Thr Asn Gly Gly Thr Thr His Tyr Pro Asp Asn Val
    50                  55                  60

Lys Gly Arg Phe Ser Ile Ser Arg Asp Asn Ala Lys Lys Phe Val Tyr
65                  70                  75                  80

Leu Gln Met Ser Ser Leu Lys Ser Asp Asp Thr Ala Ile Tyr Tyr Cys
                85                  90                  95

Pro Arg Glu Gly Leu Asp Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Glu Lys Val Glu Pro Lys Ser Cys Asp Gly Gly Gly Ser Gly
    210                 215                 220
```

```
Gly Gly Gly Ser Gln Ala Val Val Thr Gln Glu Pro Ser Leu Thr Val
225                 230                 235                 240

Ser Pro Gly Gly Thr Val Thr Leu Thr Cys Gly Ser Ser Thr Gly Ala
            245                 250                 255

Val Thr Thr Ser Asn Tyr Ala Asn Trp Val Gln Glu Lys Pro Gly Gln
                260                 265                 270

Ala Phe Arg Gly Leu Ile Gly Gly Thr Asn Lys Arg Ala Pro Gly Thr
        275                 280                 285

Pro Ala Arg Phe Ser Gly Ser Leu Leu Gly Gly Lys Ala Ala Leu Thr
    290                 295                 300

Leu Ser Gly Ala Gln Pro Glu Asp Glu Ala Glu Tyr Tyr Cys Ala Leu
305                 310                 315                 320

Trp Tyr Ser Asn Leu Trp Val Phe Gly Gly Gly Thr Lys Leu Thr Val
                325                 330                 335

Leu Ser Ser Ala Ser Thr Lys Gly Pro Ser Val Phe Pro Leu Ala Pro
                340                 345                 350

Ser Ser Lys Ser Thr Ser Gly Gly Thr Ala Ala Leu Gly Cys Leu Val
        355                 360                 365

Lys Asp Tyr Phe Pro Glu Pro Val Thr Val Ser Trp Asn Ser Gly Ala
370                 375                 380

Leu Thr Ser Gly Val His Thr Phe Pro Ala Val Leu Gln Ser Ser Gly
385                 390                 395                 400

Leu Tyr Ser Leu Ser Ser Val Val Thr Val Pro Ser Ser Ser Leu Gly
                405                 410                 415

Thr Gln Thr Tyr Ile Cys Asn Val Asn His Lys Pro Ser Asn Thr Lys
                420                 425                 430

Val Asp Lys Lys Val Glu Pro Lys Ser Cys Asp Lys Thr His Thr Cys
        435                 440                 445

Pro Pro Cys Pro Ala Pro Glu Ala Ala Gly Gly Pro Ser Val Phe Leu
    450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
                500                 505                 510

Pro Arg Glu Glu Gln Tyr Asn Ser Thr Tyr Arg Val Val Ser Val Leu
        515                 520                 525

Thr Val Leu His Gln Asp Trp Leu Asn Gly Lys Glu Tyr Lys Cys Lys
    530                 535                 540

Val Ser Asn Lys Ala Leu Gly Ala Pro Ile Glu Lys Thr Ile Ser Lys
545                 550                 555                 560

Ala Lys Gly Gln Pro Arg Glu Pro Gln Val Tyr Thr Leu Pro Pro Cys
                565                 570                 575

Arg Asp Glu Leu Thr Lys Asn Gln Val Ser Leu Trp Cys Leu Val Lys
                580                 585                 590

Gly Phe Tyr Pro Ser Asp Ile Ala Val Glu Trp Glu Ser Asn Gly Gln
        595                 600                 605

Pro Glu Asn Asn Tyr Lys Thr Thr Pro Pro Val Leu Asp Ser Asp Gly
    610                 615                 620

Ser Phe Phe Leu Tyr Ser Lys Leu Thr Val Asp Lys Ser Arg Trp Gln
625                 630                 635                 640
```

-continued

Gln Gly Asn Val Phe Ser Cys Ser Val Met His Glu Ala Leu His Asn
                645                 650                 655

His Tyr Thr Gln Lys Ser Leu Ser Leu Ser Pro
            660                 665

<210> SEQ ID NO 79
<211> LENGTH: 232
<212> TYPE: PRT
<213> ORGANISM: Artificial sequence
<220> FEATURE:
<223> OTHER INFORMATION: CD3 VH-CL

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 80
<211> LENGTH: 214
<212> TYPE: PRT
<213> ORGANISM: Artificial sequence
<220> FEATURE:
<223> OTHER INFORMATION: p95HER2 VL-CL(RK)

<400> SEQUENCE: 80

Asp Ile Val Leu Thr Gln Ser Gln Lys Phe Met Ser Thr Ser Val Gly
1               5                   10                  15

Asp Arg Val Ser Ile Ile Cys Lys Ala Ser Gln Ser Val Gly Thr Ala
            20                  25                  30

Val Ala Trp Tyr Gln Leu Lys Ala Gly Gln Ser Pro Lys Leu Leu Ile
        35                  40                  45

```
Tyr Ser Ala Ser Asn Arg Phe Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Thr Tyr Pro Leu
                85                  90                  95

Ala Phe Gly Ala Gly Thr Lys Leu Glu Leu Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```